US008772318B2

(12) United States Patent
Cravatt et al.

(10) Patent No.: US 8,772,318 B2
(45) Date of Patent: Jul. 8, 2014

(54) METHODS AND COMPOSITIONS RELATED TO TARGETING MONOACYLGLYCEROL LIPASE

(75) Inventors: Benjamin F. Cravatt, La Jolla, CA (US); Jonathan Z. Long, Solana Beach, CA (US); Weiwei Li, Sunnyvale, CA (US); Daniel K. Nomura, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 283 days.

(21) Appl. No.: 12/998,642

(22) PCT Filed: Nov. 10, 2009

(86) PCT No.: PCT/US2009/006045
§ 371 (c)(1),
(2), (4) Date: Jul. 26, 2011

(87) PCT Pub. No.: WO2010/056309
PCT Pub. Date: May 20, 2010

(65) Prior Publication Data
US 2011/0275650 A1    Nov. 10, 2011

Related U.S. Application Data

(60) Provisional application No. 61/199,286, filed on Nov. 14, 2008.

(51) Int. Cl.
*A61K 31/443* (2006.01)
*C07D 405/06* (2006.01)

(52) U.S. Cl.
USPC ........... 514/321; 546/184; 546/192; 546/197; 514/315

(58) Field of Classification Search
USPC ................... 546/184, 192, 197; 514/315, 321
See application file for complete search history.

(56) References Cited

U.S. PATENT DOCUMENTS 7,989,623 B2 * 8/2011 Zhu ............................. 544/389
2006/0089406 A1   4/2006 Nieland et al.

FOREIGN PATENT DOCUMENTS

WO   WO 2010/074588   7/2010

OTHER PUBLICATIONS

Blankman, et al., "A Comprehensive Profile of Brain Enzymes that Hydrolyze the Endocannabinoid 2-Arachidonoylglycerol", *Chemistry & Biology 14*: 1347-1356 (2007).
Dinh, et al., "RNA Interference Suggests a Primary Role for Monoacylglycerol Lipase in the Degradation of the Endocannabinoid 2-Arachidonoylglycerol", *Molecular Pharmacology* 66(5): 1260-1264 (2004).
Goparaju, et al., "Anandamide amidohydrolase reacting with 2-arachidonoylglycerol, another cannabinoid receptor ligand" *FEBS Letters 422*: 69-73 (1998).
Hohmann, et al., "An endocannabinoid mechanism for stress-induced analgesia", *Nature 435*: 1108-1112 (2005).
Kathuria, et al., "Modulation of anxiety through blockade of anandamide hydrolysis", *Nature Medicine* 9(1): 76-81 (2003).
Li, et al., "A Functional Proteomic Strategy to Discover Inhibitors for Uncharacterized Hydrolases", *J. Am. Chem. Soc.* 129(31): 9594-9595 (2007).
Viso, et al., "The Medicinal Chemistry of Agents Targeting Monoacylglycerol Lipase". *Current Topics in Medicinal Chemistry* 8(3): 231-246 (2008).

* cited by examiner

*Primary Examiner* — Golam M M Shameem
(74) *Attorney, Agent, or Firm* — Hugh Wang; Thomas Fitting

(57) ABSTRACT

This invention provides compounds that selectively inhibit monoacylglycerol lipase (MAGL). The invention also provides methods of using the MAGL selective inhibitors to stimulate 2-Arachidonoylglycerol (2-AG) mediated endocannabinoid signaling in vivo, and to treat conditions that are associated with or linked to endocannabinoid signaling. The invention additionally provides methods of treating cancer or inhibiting tumor growth by targeting MAGL with MAGL specific inhibitors. The invention further provides methods of screening for MAGL inhibitors with improved biochemical and pharmaceutical properties.

4 Claims, 25 Drawing Sheets

```
                          SEQUENCE LISTING

<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: Synthetic sequence

<400> SEQUENCE: 1
caactttcaa ggtccttgc                                                    19

<210> SEQ ID NO 2
<211> LENGTH: 19
<212> TYPE: DNA
<213> ORGANISM: Artificial Sequence
<220> FEATURE:
<223> OTHER INFORMATION: Synthetic sequence

<400> SEQUENCE: 2
agactaccct gggcttcct                                                    19

<210> SEQ ID NO 3
<211> LENGTH: 19
<212> TYPE: DNA
<213> ORGANISM: Artificial Sequence
<220> FEATURE:
<223> OTHER INFORMATION: Synthetic sequence

<400> SEQUENCE: 3
gattcttctg ggactgctg                                                    19

<210> SEQ ID NO 4
<211> LENGTH: 33
<212> TYPE: DNA
<213> ORGANISM: Artificial Sequence
<220> FEATURE:
<223> OTHER INFORMATION: Synthetic sequence

<400> SEQUENCE: 4
gctctcgagg ccgccatgcc agaggaaagt tcc                                    33

<210> SEQ ID NO 5
<211> LENGTH: 33
<212> TYPE: DNA
<213> ORGANISM: Artificial Sequence
<220> FEATURE:
<223> OTHER INFORMATION: Synthetic sequence

<400> SEQUENCE: 5
agctgaattc tcagggtggg gacgcagttc ctg                                    33
```

METHODS AND COMPOSITIONS RELATED TO TARGETING MONOACYLGLYCEROL LIPASE

CROSS-REFERENCE TO RELATED APPLICATIONS

The subject patent application claims the benefit of priority to U.S. Provisional Patent Application No. 61/199,286 (filed Nov. 14, 2008). The full disclosures of the priority application are incorporated herein by reference in their entirety and for all purposes.

STATEMENT CONCERNING GOVERNMENT SUPPORT

This invention was made with government support under Grant Nos. DA017259, DA025285 and CA132630 awarded by the National Institutes of Health. The Government has certain rights in this invention.

COPYRIGHT NOTIFICATION

Pursuant to 37 C.F.R. §1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention generally relates to methods and compositions for selectively inhibiting monoacylglycerol lipase (MAGL) over other brain serine hydrolases, and for stimulating 2-Arachidonoylglycerol (2-AG) mediated endocannabinoid signaling in a subject. The invention also related to methods for inhibiting growth of tumor cells and methods for treating cancer.

BACKGROUND OF THE INVENTION

The cannabinoid receptors CB1 and CB2 are molecular targets for $\Delta^9$-tetrahydrocannabinol, the psychoactive component of marijuana. CB1 which is expressed mainly in the brain, but also in the lungs, liver and kidneys. CB2 which is mainly expressed in the immune system and in hematopoietic cells. Two endogenous ligands, or "endocannabinoids," have also been identified, the arachidonate-based lipids anandamide (N-arachidonoyl ethanolamine, AEA) and 2-arachidonoylglycerol (2-AG). The endocannabinoid system regulates a range of physiological processes, including appetite, pain sensation, inflammation, and memory, and is the current focus of considerable pharmaceutical interest to treat disorders such as obesity, chronic pain, anxiety, and depression.

Endocannabinoid signaling is tightly controlled by enzymatic hydrolysis. Hydrolysis of 2-AG or AEA leads to production of arachidonic acid (AA). The principal AEA-hydrolyzing enzyme is fatty acid amide hydrolase (FAAH). Genetic or pharmacological disruption of FAAH causes significant elevations in AEA levels throughout the nervous system and periphery, resulting in multiple CB1- and/or CB2-dependent behavioral effects, including reduction in pain sensation, inflammation, anxiety, and depression. Interestingly, several of the other well-known behavioral effects of direct CB1 agonists, such as hypothermia and movement disorders, are not observed in FAAH-disrupted animals (Goparaju et al., FEBS Lett. 422:69-73, 1998; and Kathuria et al., Nat Med 9:76-81, 2003). These animals also possess wild-type levels of 2-AG17, which suggests that additional CB1-regulated behavioral processes may be mediated by 2-AG in vivo. Several lines of evidence suggest that monoacylglycerol lipase (MAGL) is a primary enzyme responsible for hydrolyzing 2-AG in the nervous system. See, e.g., Dinh et al., Proc. Natl. Acad. Sci. USA 99:10819-24, 2002; Dinh et al., Mol. Pharmacol. 66:1260-4, 2004; Blankman et al., Chem. Biol. 14:1347-56, 2007; and Nomura et al., Nat. Chem. Biol. 4:373-8, 2008. However, none of these previous studies have specifically examined the role that MAGL plays in hydrolyzing 2-AG in vivo. While several MAGL inhibitors have been described in the art (Hohmann et al., Nature 435:1108-12, 2005; Varvel et al., J. Pharmacol. Exp. Ther. 301:915-24, 2002; and Saario et al., Chem. Biol. 12:649-56, 2005), none of them show the level of potency and specificity required for general use as in vivo pharmacological tools.

Tumors and cancers are common diseases or conditions that threaten many people's life and health. Uninhibited growth of aggressive tumor cells often results in the formation of malignant tumors (cancer). There are still no effective medicines or treatments which can radically cure cancers. At present, main methods used in the treatment of tumor are operation, radiotherapy, chemotherapy, biologic therapy, and others such as endocrine treatment, Chinese traditional therapy, thermotherapy, radiofrequency ablation therapy and so on. However, most available treatments can only relieve the patients' symptom and physical sign but can not cure the disease, and each of the treatments usually has its disadvantages including side effects.

There is a need in the art for compounds that can potently and selectively inhibit MAGL in vivo, and for novel means for treating conditions or disorders that are associated with or linked to endocannabinoid signaling activities. There us also a need for alternative and more effective means for inhibiting tumor growth and for treating cancers. The present invention addresses these and other unfulfilled needs in the art.

SUMMARY OF THE INVENTION

In one aspect, the present invention provides methods for stimulating 2-Arachidonoylglycerol (2-AG) mediated endocannabinoid signaling in a subject. The methods entail administering (e.g., via intraperitoneal injection or oral administration) to the subject a therapeutic effective amount of a compound that selectively inhibits monoacylglycerol lipase (MAGL). In some of these methods, the compound is selective for inhibition of MAGL over fatty acid amide hydrolase (FAAH). For example, the compound can have at least 100-fold selectivity for inhibition of MAGL over FAAH. The MAGL selective inhibitor employed in some of these methods have the structure shown in formula I disclosed herein. In some other methods, the MAGL specific inhibitor is selective for MAGL over both FAAH and α/β hydrolase 6 (ABHD6). In some preferred embodiments, the MAGL selective inhibitor is compound JZL184. Preferably, the subjects to be treated with the methods of the invention are humans. In some of these methods, the subjects to be treated suffer from conditions or disorders that are mediated by or associated with endocannabinoid signaling, e.g., pain, inflammation, depression or anxiety.

In a related aspect, the invention provides methods for treating or ameliorating in a subject a condition that is associated with or linked to endocannabinoid signaling, or a disease for which therapeutic effects can be derived from elevated levels of cannabinoids (e.g., 2-AG). These methods involve administering to the subject a pharmaceutical composition that comprises a therapeutically effective amount of a compound that selectively inhibits monoacylglycerol lipase (MAGL). Some of these methods are directed to treating conditions or disorder in which 2-AG signaling plays a role, e.g., pain. Some of these methods employ a MAGL-selective inhibitor that has the structure shown in formula I. In some of the methods, the MAGL-selective inhibitor selectively inhibits monoacylglycerol lipase (MAGL) over FAAH. In some other methods, the employed compound is selective for inhibition of MAGL over both FAAH and ABHD6. In some preferred embodiments, the MAGL-selective inhibitor employed is compound JZL184.

In another aspect, the invention provides MAGL-selective inhibitor compounds. These compounds have a structure shown in formula I below:

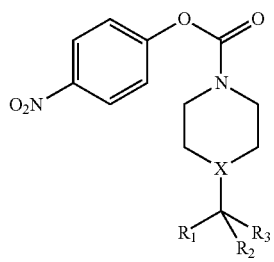

wherein X is N or CH, $R_1$ is H or OH, and $R_2$ and $R_3$ each have one of the following structures.

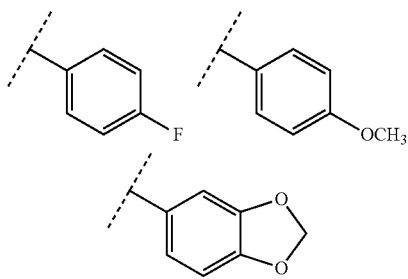

A preferred MAGL-selective inhibitor compound of the invention is compound JZL184. It structure is shown in formula I, wherein X is CH, $R_1$ is OH, and $R_2$ and $R_3$ each have the structure shown below.

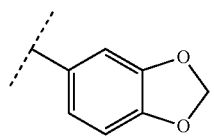

In still another aspect, the invention provides methods for identifying MAGL inhibitor compounds with improved properties. The methods entail (a) synthesizing one or more structural analogs of a MAGL selective inhibitor disclosed herein (e.g., JZL184); (b) performing a functional assay on the analogs to identify an analog that has an improved biological or pharmaceutical property relative to that of the MAGL selective inhibitor. Any of the compounds encompassed by formula I can serve as the lead compound for synthesis of structural analogs. In some preferred embodiments, compound JZL184 is used. In these screening methods, the improved biological or pharmaceutical property to be identified in the analogs can be, e.g., an enhanced inhibitory activity for MAGL or an increased selectivity for MAGL over other brain serine hydrolases.

In another aspect, the invention provides methods for inhibiting growth of tumor cells, especially aggressive tumor cells. The methods entail contacting the tumor cells with a therapeutically effective amount of a compound that specifically inhibits monoacylglycerol lipase (MAGL). In some embodiments, the methods are directed to inhibiting growth of a tumor that is present in a subject. The subject can be one who is diagnosed to have a cancer. The subject can also be one who is predisposed to or at risk of developing a cancer. The methods can be employed to inhibit growth of any tumor cells including cells of solid tumor and leukemia. In some embodiments, the methods are used to inhibit growth of a breast tumor cell, an ovarian tumor cell, a melanoma cell, a lung tumor cell or a brain tumor cell.

In some methods of the invention, the employed MAGL-inhibiting compound (or "MAGL-antagonizing compound" or "MAGL-antagonist compound") is selective for inhibition of MAGL over fatty acid amide hydrolase (FAAH). For example, the compound can be any of the MAGL-selective inhibitors disclosed herein. In some other embodiments, the employed MAGL-inhibiting compound is an inhibitory polynucleotide specific for MAGL. Examples of such inhibitory polynucleotides include short interfering RNAs (siRNAs), microRNAs (miRNAs), short hairpin RNAs (shRNAs), antisense nucleic acids and complementary DNAs (cDNAs).

In a related aspect, the invention provides methods for treating or ameliorating symptoms of a tumor in a subject. These methods involve administering to the subject a pharmaceutical composition comprising a therapeutically effective amount of a compound that specifically inhibits monoacylglycerol lipase (MAGL). Subjects afflicted with any tumor or cancer are amendable for treatment with these methods. For example, the methods can be employed to treat a subject suffering from a breast tumor, an ovarian tumor, a melanoma, a lung tumor or a brain tumor. In some methods, the employed MAGL-inhibiting agent is a compound that is selective for inhibiting MAGL over fatty acid amide hydrolase (FAAH). In some other methods, an inhibitory polynucleotide which specifically down-regulates MAGL expression or cellular level is used.

A further understanding of the nature and advantages of the present invention may be realized by reference to the remaining portions of the specification and claims.

DETAILED DESCRIPTION

I. Overview

Figure 1:
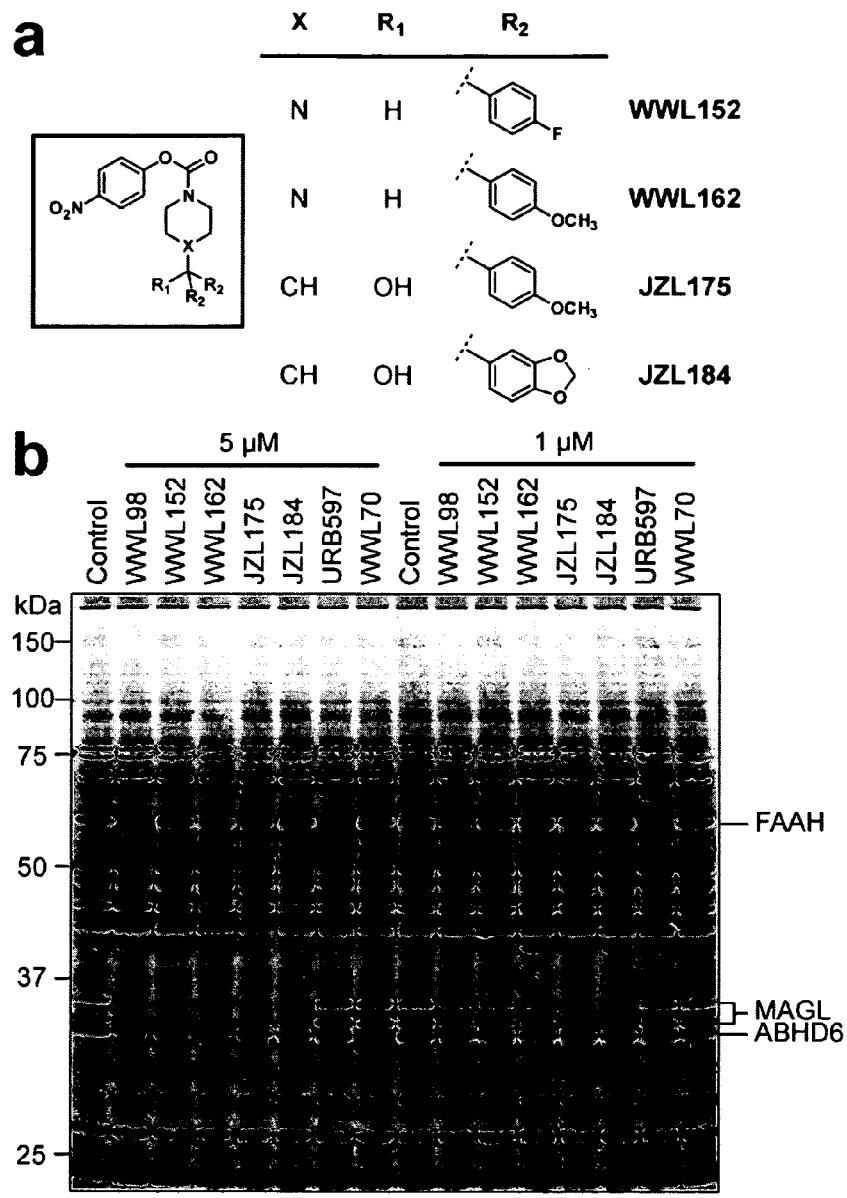
FIGS. 1A-1B show structures and competitive ABPP profiles of MAGL inhibitors. A: Structures of MAGL inhibitors; B: Competitive ABPP showing the effect of MAGL inhibitors on serine hydrolase activities in the mouse brain membrane proteome. Shown for comparison are the profiles of the selective FAAH and ABHD6 inhibitors, URB597 (Kathuria et al., Nat Med 9:76-81, 2003) and WWL70 (Li et al., J. Amer. Chem. Soc. 129:9594-5, 2007), respectively. Inhibitors were incubated with brain membranes for 30 min, followed by treatment with the serine hydrolase-directed ABPP probe FP-rhodamine (2 µM, 30 min), and the proteomes were then analyzed by SDS-PAGE and in-gel fluorescence scanning to detect inhibited enzymes. Control proteomes were treated with DMSO alone. Fluorescent gel is shown in grayscale. Note that brain MAGL migrates as a 35 kDa doublet by SDS-PAGE, as reported in the literature (e.g., Blankman et al., Chem. Biol. 14:1347-56, 2007).

2-Arachidonoylglycerol (2-AG) and anandamide are lipid transmitters that activate cannabinoid receptors CB1 and CB2. Endocannabinoid signaling is terminated by enzymatic hydrolysis, a process that, for anandamide, is mediated by fatty acid amide hydrolase (FAAH) and, for 2-AG, is thought to be principally regulated by monoacylglycerol lipase (MAGL). The present invention is predicated in part on the synthesis and characterization by the present inventors of selective inhibitors of MAGL. It was found that the MAGL selective inhibitors potently inhibit hydrolase activity of MAGL while having little or no inhibitory activity on other brain serine hydrolases such as FAAH. In addition, upon intraperitoneal injection or oral administration to mice, the selective MAGL inhibitors were able to significantly raise brain 2-AG levels and do not alter levels of other known lipid signaling molecules such as anandamide or the other N-acylethanolamines. Mice treated with the inhibitors also display an array of CB1-dependent behavioral effects, including analgesia.

The inventors further discovered that MAGL and its free fatty acid (FFA) products are upregulated in aggressive human cancer cells and primary tumors, where it regulates a fatty acid network enriched in oncogenic signaling lipids that promotes migration, invasion, survival, and in vivo tumor growth. It was found that overexpression of MAGL in non-aggressive cancer cells recapitulates this fatty acid network and increases their pathogenicity - phenotypes that are reversed by an MAGL inhibitor. The inventors observed that blockade of MAGL impaired not only in vitro migration but also in vivo tumor growth. In addition, the phenotypes derived from MAGL blockade were rescued by exogenous sources of FFAs. These data indicate that MAGL is both necessary and sufficient to elevate FFAs and confer high migratory and tumorigenic activity in cancer cells.

In accordance with these discoveries, the invention provides therapeutic compositions that contain a MAGL selective antagonist compound or a pharmaceutically acceptable salt thereof. These compositions can be used to treat, or ameliorate symptoms of, disorders or conditions in a subject that are linked to or mediated by aberrant or insufficient cannabinoid signaling, especially 2-AG-mediated endocannabinoid signaling, or to treat diseases which can derive beneficial effects from increased levels of cannabinoids. Such disorders or conditions include, e.g., pain, inflammation, depression, anxiety, multiple sclerosis, glaucoma, and Alzheimer. In addition to therapeutic applications in subjects suffering from any of these specific conditions or disorders, the compositions of the invention can also be employed in general to induce cannabinoid dependent behavioral effects (e.g., analgesia) or to stimulate or augment 2-AG-mediated endocannabinoid signaling activities in other subjects. Using the MAGL selective inhibitory compounds exemplified herein as lead compounds, the invention further provides methods of screening for novel MAGL inhibitors with improved biological activities and pharmaceutical characteristics. Such novel MAGL inhibitors can provide therapeutic agents with enhanced properties in the treatment of disorders or conditions caused by or associated with abnormal or decreased cannabinoid signaling activities. The following sections provide guidance for making and using the compositions of the invention, and for carrying out the methods of the invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). In addition, the following definitions are provided to assist the reader in the practice of the invention.

The term "agent" or "test agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" is used herein to refer to a molecule that structurally resembles a reference molecule (e.g., a MAGL selective inhibitor disclosed herein) but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

"Antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

Chemotherapeutic agents can be used in combination with polyclonal anti-glycan antibodies in methods for treatment of neoplastic disease. An antibody-cytotoxin conjugate comprising anti-glycan antibodies can also be used to boost immunity induced through standard cancer treatments. In these instances, it can be possible to reduce the dose of chemotherapeutic reagent administered (Mokyr et al., *Cancer Research* 58: 5301-5304, 1998). The scientific rationale behind the combined use of anti-glycan antibodies is that cell death, that is a consequence of the cytotoxic action of most chemotherapeutic compounds, should result in increased levels of tumor antigen in the antigen presentation pathway. Thus, anti-glycan antibodies can boost an immune response primed to chemotherapy release of tumor cells.

As used herein, "contacting" has its normal meaning and refers to combining two or more molecules or combining molecules and cells (e.g., a compound and a cell). Contacting can occur in vitro, e.g., combining two or more agents or combining an agent and a cell or a cell lysate in a test tube or other container. Contacting can also occur in vivo, e.g., by administering to a subject an agent that specifically target a protein or polypeptide inside the body of the subject.

Conditions or disorders associated with cannabinoid signaling refer to disorders that are linked to, mediated by or associated with aberrant or suppressed endocannabinoid signaling. Thus, they encompass conditions that are caused by decreased levels of endocannabinoids (e.g., 2-AG) or excessive enzymatic activities that degrade the endocannabinoids. Conditions or disorders associated with cannabinoid signaling also include conditions for which beneficial, effects can be derived by augmenting endocannabinoid signaling (e.g., pain). The term also broadly encompasses diseases for which therapeutic effects can be obtained from an elevated level of cannabinoids or a decreased level of arachidonic acid (e.g., Alzheimer or multiple sclerosis). In some preferred embodiments of the invention, the conditions or disorders are those which are related to or associated with 2-AG signaling (e.g., aberrant or suppressed 2-AG signaling), or which can derive beneficial effect by stimulating 2-AG signaling activities. Examples of such conditions or disorders include pain, depression, anxiety, cardiovascular disorders, metabolic disorders, inflammatory syndromes and stroke.

As used in the present invention, the term cardiovascular disorder refers to a class of diseases that involve the heart or blood vessels (arteries and veins). It includes any disease that affects the cardiovascular system, but in particular refers to those conditions related to atherosclerosis (arterial disease). These conditions have similar causes, mechanisms, and treatments. Examples of common cardiovascular disorders include arteriosclerosis (hardening of the arteries), atherosclerosis (plaque, such as cholesterol build-up on the walls of blood vessels), rheumatic heart disease, systemic hypertension and stroke. As used herein, inflammatory disorders are diseases or conditions associated with abnormal, excessive or deregulated inflammation. They comprise a large, unrelated group of disorders underlying a variety of human diseases, e.g., allergic reactions and some myopathies. Metabolic disorders refer to medical conditions that develop when some metabolic reaction essential for normal growth and development does not occur. These include disorders of amino acid metabolism (e.g., maple syrup urine disease and homcystinuria), disorders of organic acid metabolism (e.g., methylmalonic aciduria), disorders of fatty acid beta-oxidation (e.g., MCAD deficiency), disorders of lipid metabolism (lipid storage disorders) such as Tay-Sachs disease and Gaucher disease, mitochondrial disorders (e.g., mitochondrial cardiomyopathies), and peroxisomal disorders (e.g., Zellweger syndrome).

Cannabinoid behavioral effects (or CB1-dependent and/or CB2-dependent behavioral effects) refer to physiological and behavioral responses displayed by a subject as a result of cannabinoid signaling activities. Some of the cannabinoid behavioral effects involve 2-AG signaling, and are termed herein 2-AG mediated behavioral effects (or 2-AG dependent behavioral effects). As detailed in the Examples below, examples of 2-AG mediated behavioral effects include analgesia (reduced pain sensation). Unless otherwise indicated, cannabinoid behavioral effects also encompass a reduction or amelioration of symptoms associated with inflammation, anxiety or depression present in or experienced by a subject.

The endocannabinoid system refers to a group of neuromodulators and their receptors that are involved in a variety of physiological processes including appetite, pain-sensation, mood, and memory. It is named for endocannabinoids, the endogenous lipids that bind cannabinoid receptors (the same receptors that mediate the psychoactive effects of cannibis). Broadly speaking, the endocannabinoid system includes (1) the cannabinoid receptors CB1 and CB2, 2 G-protein coupled receptors primarily located in the central nervous system and periphery, respectively; (2) the endogenous arachidonate-based lipids, anandamide (N-arachidonoyl ethanolamine or AEA) and 2-arachidonoylglycerol (2-AG), collectively termed the "endocannabinoids," that are ligands for the cannabinoid receptors; and (3) the enzymes that synthesize and degrade the endocannabinoids anandamide and 2-AG. The endocannabinoid system has been studied using genetic and pharmacological methods. These studies have revealed a broad role for endocannabinoid signaling in a variety of physiological processes, including neuromodulator release, motor learning, synaptic plasticity, appetite, and pain sensation.

Hyperalgesia is a condition in which a subject (e.g., a warm-blooded animal) displays an increased sensitivity to pain. It is known to accompany certain physical injuries to the body, for example the injury inevitably caused by surgery. Pain is also known to accompany certain inflammatory conditions in man such as arthritic and rheumatic disease. Hyperalgesia includes mild to moderate pain to severe pain such as the pain associated with, but not limited to, inflammatory conditions (e.g., such as rheumatoid arthritis and osteoarthritis), postoperative pain, post-partum pain, the pain associated with dental conditions (e.g., dental caries and gingivitis), the pain associated with burns, including but not limited to sunburns, abrasions, contusions and the like, the pain associated with sports injuries and sprains, inflammatory skin conditions, including but not limited to poison ivy, and allergic rashes and dermatitis, and other pains that increase sensitivity to mild stimuli, such as noxious cold.

The term "modulate" with respect to an activity of a reference molecule (e.g., a MAGL polypeptide) or a cell (e.g., a tumor cell) refers to up-regulation (i.e., activation or stimulation) or down-regulation (i.e. inhibition or suppression) of the activity. Modulation of a reference molecule such as a polypeptide also encompasses a change in the expression or cellular level of the molecule. The term "inhibit" or "inhibition" with respect to a biological activity (e.g., MAGL expression or lipase activity, or growth of a tumor cell) refers to suppression or down-regulation of the activity. The mode of inhibition can be direct, e.g., through binding to the reference molecule or cell. The inhibition can also be indirect, e.g., through binding to and/or modifying another molecule which otherwise binds to and modulates the reference molecule or cell.

"Polynucleotide" or "nucleic acid sequence" refers to a polymeric form of nucleotides (polyribonucleotide or polydeoxyribonucleotide). In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. Polynucleotides can be ribonucleotides, deoxyribonucleotides, or modified forms of either nucleotide.

A polypeptide or protein refers to a polymer in which the monomers are amino acid residues that are joined together through amide bonds. When the amino acids are alpha-amino acids, either the L-optical isomer or the D-optical isomer can be used, the L-isomers being typical. A polypeptide or protein fragment can have the same or substantially identical amino acid sequence as the naturally occurring protein. A polypeptide or peptide having substantially identical sequence means that an amino acid sequence is largely, but not entirely, the same, but retains a functional activity of the sequence to which it is related.

The term "subject" includes mammals, especially humans, as well as other non-human animals, e.g., horse, dogs, cats, mice and rats.

A "variant" of a reference molecule (e.g., a MAGL selective inhibitor) is meant to refer to a molecule substantially similar in structure and biological activity to either the entire reference molecule, or to a fragment thereof. Thus, provided that two molecules possess a similar activity, they are considered variants as that term is used herein even if the composition or structure of one of the molecules is not identical to that found in the other, or if the sequence of amino acid residues is not identical.

Aggressive cancer or aggressive tumor refers to a cancer or tumor that grows and spreads quickly. Cancer or tumor of any origin can become aggressive under suitable conditions. Thus, aggressive tumors can include, e.g., aggressive breast cancer, aggressive prostate cancer, aggressive brain tumors, aggressive cervical cancer, aggressive colon cancer, aggressive lung cancer, aggressive stomach cancer, aggressive liver cancer, aggressive kidney cancer, aggressive melanoma and aggressive ovarian cancer. For a tumor to become aggressive, it needs to be able to nourish the cells at the center of its mass that are too far away from blood vessels. This is achieved by angiogenesis. Through mutation, a few cancer cells may gain the ability to produce angiogenic growth factors. These growth factors are proteins that are released by the tumor into nearby tissues, where they stimulate new blood vessels to grow into the tumor. This allows the tumor to rapidly expand in mass and invade surrounding tissue. It also provides a route for the cancer cells to escape into the new blood vessels and circulate throughout the body, where they can lodge in other organs forming metastases.

III. MAGL Selective Inhibitors

The invention provides novel MAGL inhibitors. MAGL inhibitors include compounds that interfere with the expression, modification, regulation or activation of MAGL, or compounds that down-regulate one or more of the normal biological activities of MAGL (e.g., its serine hydrolase activity). In particular, MAGL inhibitors of the invention block or inhibit the enzymatic activities of MAGL. As noted above, MAGL is the primary enzyme responsible for hydrolyzing 2-AG, the cannabinoid receptor ligand, in the nervous system. MAGL inhibitors or antagonist compounds are useful in inducing cannabinoid dependent behavioral effects such as analgesia. Compounds that specifically inhibit or suppress MAGL enzymatic activities can have various therapeutic or prophylactic applications in treating disorders or conditions caused by or linked to abnormal (e.g., suppressed or decreased) cannabinoid signaling activities (e.g., pain). Any molecule that inhibits the MAGL enzymatic activity might be able to induce cannabinoid dependent behavioral effects or to treat conditions linked to suppressed cannabinoid signaling activities. However, MAGL antagonist compounds which also inhibit other brain serine hydrolases (e.g., FAAH) can interfere with the various biological functions mediated by those other enzymes. Such nonselective inhibitors of MAGL, although being able to treat disorders linked to suppressed cannabinoid signaling activities (e.g., diminish pain), are likely to have many unwanted side effects. Thus, molecules that selectively inhibit the MAGL enzyme are preferred in such therapeutic applications. By specifically inhibiting MAGL enzymatic activity while causing no significant effect on the other brain serine hydrolases (e.g., FAAH), symptoms of a subject suffering from a condition associated with or linked to insufficient or suppressed 2-AG signaling activities can be treated or ameliorated.

Accordingly, the invention provides novel MAGL-selective inhibitors (or "MAGL-specific inhibitors") that substantially block or inhibit the enzymatic activity of MAGL at a concentration at which enzymatic activity of one or more of the other brain serine hydrolase (e.g., FAAH or ABHD6) is not significantly affected. In some preferred embodiments, the MAGL inhibitors block hydrolysis of 2-AG by MAGL. In particular, MAGL selective inhibitors or MAGL selective antagonists of the invention are compounds that exhibit selectivity for inhibition of MAGL relative to inhibition of FAAH. Selectivity of a compound for MAGL over another brain serine hydrolase (e.g., FAAH) can be determined by assaying enzymatic activity of each enzyme on its cognate substrate in the presence of the compound. As detailed in the Examples herein, selectivity can be determined by measuring the $IC_{50}$ value of inhibition of hydrolysis of the substrate (e.g., 2-AG for MAGL and oleamide for FAAH) by the compound in brain membrane proteomes. In addition to measuring $IC_{50}$ values, selectivity of an inhibitor for MAGL over FAAH can also be determined by measuring pseudo-first-order rate constants ($k_{obs}/[I]$) of the enzyme catalyzed hydrolysis reactions in the presence of the compound. This can also be performed in vitro with enzyme present in brain membrane proteome as described in the Examples below. Other than using the hydrolase enzymes present in brain membrane proteomes, the enzyme activity assays can also performed with recombinant enzymes. For example, MAGL, FAAH as well as other brain serine hydrolases can be readily obtained recombinantly in accordance with the methods described herein or that reported in the art (e.g., Blank et al., Chem. Biol. 14:1347-56, 2007). Typically, a MAGL selective inhibitor should have an $IC_{50}$ value for MAGL that is at least 20-fold, preferably at least 50-, 100-, 250- or 500-fold lower than its $IC_{50}$ value for FAAH. If measured by $k_{obs}/[I]$, the MAGL selective inhibitor will usually have a rate constant for MAGL that at least 10-fold, preferably, at least 25-, 50-, 75-, 100-, or 300-fold higher than that for FAAH.

In addition to FAAH, some of the MAGL selective inhibitors of the invention are also selective for MAGL over one or more of the other brain serine hydrolases. For example, the compound can be selective for MAGL over ABHD6 and/or ABHD12. ABHD6 and ABHD12 are the other two brain enzymes that have been shown to exhibit 2-AG hydrolase activity in mouse brain and display distinct subcellular distributions (see, e.g., Blank et al., Chem. Biol. 14:1347-56, 2007). MAGL selective antagonists that do not inhibit these enzymes are useful to study and identify presently unknown functions associated with endocannabindid signaling.

Various MAGL-selective antagonists can be used in the instant invention. Some of these MAGL-selective inhibitors synthesized by the present inventors are described in the Examples below. These compounds have a structure of formula I shown below. These compounds can be readily prepared according to the synthesis scheme disclosed in the Examples herein.

Formula I:

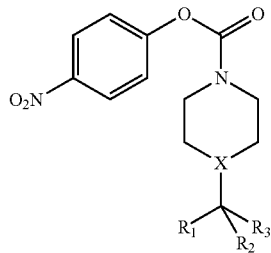

wherein X is N or CH, $R_1$ is H or OH, and $R_2$ and $R_3$ each can have one of the following structures.

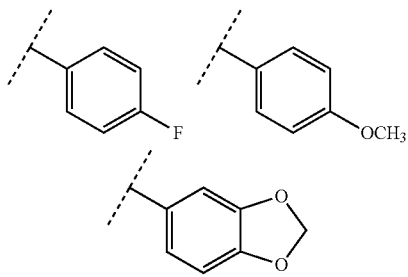

Some of the exemplified MAGL-specific inhibitors are selective for inhibition of MAGL over FAAH. As detailed in the Examples, compounds WWL152, WWL162, JZL175 and JZL184 shown in FIG. 1A all exhibit selectivity for MAGL over FAAH. Some of the compounds are also selective for MAGL over other brain serine hydrolases in addition to FAAH. These include compounds JZL184 and JZL175 encompassed by Formula I. These two compounds specifically inhibit MAGL and have no or greatly reduced inhibitory activity on FAAH as well as ABHD6.

Any of these MAGL-selective inhibitors can be produced in accordance with the synthesis schemes detailed in the Examples below. Other than the exemplified MAGL-selective antagonists, additional MAGL-selective inhibitors (e.g., functional derivatives or analogs of JZL184 or JZL175) can be readily identified using methods described herein or methods that have been described in the art. As described herein, a library of analog compounds of an exemplified MAGL-selective inhibitor can be synthesized. The analog compounds can then be screened for specific activity in inhibiting MAGL and selectivity over the other brain serine hydrolases.

IV. Enhancing Endocannabinoid Signaling and Treating Conditions Associated therewith The invention provides methods of stimulating or augmenting endocannabinoid signaling (especially 2-AG signaling activities) or inhibiting cannabinoid hydrolysis (e.g., 2-AG hydrolysis) in a subject that is in need of such treatment. As demonstrated in the Examples below, selective inhibition of MAGL with the MAGL specific inhibitors of the invention is sufficient to augment 2-AG-mediated endocannabinoid signaling in vivo, while limiting any unintended consequences that might otherwise occur with non-selective inhibition of brain serine hydrolases. The present inventors also identified that some cannabinoid dependent behavioral effects can be derived from selective inhibition of MAGL. These behavioral effects (2-AG mediated behavioral effects) include, e.g., analgesia, hypomotility, hypothermia, and hyperreflexia. Under various circumstances, it might be desirable to induce certain 2-AG mediated behavioral effects (e.g., analgesia) in some subjects. For example, a subject suffering from pain can derive therapeutic benefits from analgesia induced with MAGL selective inhibition. To stimulate or augment 2-AG signaling activities in the subject, the methods involve administering to the subject a therapeutic effective amount of a MAGL selective inhibitor disclosed herein. Some related methods are directed to inducing in a subject CB1- and/or CB2-dependent behavioral effects via administering to the subject a MAGL selective inhibitor of the invention. In some of these methods, the subject is administered with the compound so that a behavioral effect mediated by 2-AG mediated can be induced, e.g., analgesia.

The MAGL selective inhibitors disclosed herein are also in general suitable for treating disorders caused by or associated with abnormal cannabinoid signaling (especially 2-AG signaling activities), or conditions for which beneficial effects can be obtained by augmenting or stimulating 2-AG signaling activities. Accordingly, employing the MAGL selective inhibitors, the invention further provides methods for treating subjects suffering from disorders or conditions linked to or associated with cannanonoid signaling. The methods entail administering to the subjects in need of treatment a therapeutically effective amount of a MAGL selective inhibitor disclosed herein. The subjects to be treated include those suffering from disorders or conditions that are mediated by or associated with aberrant (insufficient or suppressed) cannabinoid signaling. The subjects to be treated can also be one with a condition for which beneficial effects can be derived from augmented cannabinoid signaling activities. In some preferred embodiments, the methods are directed to stimulating 2-AG mediated signaling activities in subjects suffering from conditions associated with 2-AG signaling. Examples of these disorders and conditions include pain, inflammation, anxiety, depression, cardiovascular disorders, metabolic disorders, and stroke. There are many inflammatory disorders that are suitable for the methods of the present invention. These disorders are all well known in the art, e.g., asthma, autoimmune diseases, chronic inflammation, chronic prostatitis, glomerulonephritis, hypersensitivities, inflammatory bowel diseases, pelvic inflammatory diseases, reperfusion injury, rheumatoid arthritis, transplant rejection and vasculitis. In addition to stroke, cardiovascular disorders suitable for the therapeutic methods of the present invention also include aneurysm, angina, atherosclerosis, cerebrovascular diseases, congestive heart failure, coronary artery diseases, and myocardial infarction (heart attack). Similarly, metabolic disorders that can be benefited from augmenting endocannabinoid signaling (e.g., 2-AG mediated signaling activities) are well known in the art. Examples of such disorders include phenylketonuria, alkaptonuria, thalassemia, porphyria, Tay-Sachs disease, Hurler's syndrome, Gaucher's disease, galactosemia, Cushing's syndrome, diabetes mellitus, hyperthyroidism, and hypothyroidism.

The MAGL selective inhibitors of the invention can also be utilized to treat other conditions for which therapeutic effects of cannabinoids have been reported. Examples of such conditions or disorders include glaucoma, multiple sclerosis and wasting diseases caused by suppressed appetite. Wasting refers to the process by which a debilitating disease (e.g., bacterial or viral infection) or condition that causes muscle and fat tissue to "waste" away. It has been reported that cannabinoids can provide certain therapeutic effects to these diseases or disorders. See, e.g., Newell et al., Trans. Ophthalmol. Soc. UK 99:269-71, 1979; Bushwald et al., Pharmazie. 57:108-14, 2002; Croxford et al., Drugs Today 40:663-76, 2004; Whelan, Drug Discov. Today 7:745-6, 2002; and Costiniuk et al., Can. J. Gastroenterol. 22:376-80, 2008. The MAGL selective inhibitors can promote the therapeutic effects by inhibiting hydrolysis of 2-AG. The MAGL selective inhibitors of the invention can further be employed to provide therapeutic benefits to subjects suffering from Alzheimer. It has been reported that elevated arachidonic acid is present in the brains of Alzheimer subjects, suggesting a role for arachidonic acid in the development and progression of the Alzheimer disease. See, e.g., Ross et al., J. Neurochem. 70:786-93, 1998; Charlimoniuk et al., Neurochem. Int. 48:1-8, 2006; and Rapoport, Prostaglandins Leukot Essent Fatty Acids, Oct. 28, 2008. By inhibiting MAGL enzymatic activities with the MAGL inhibitors of the present invention, the hydrolysis of 2-AG and resulting production of arachidonic acid can be suppressed or reduced.

Typically, the therapeutic methods of the invention involve administering to a subject in need of treatment a pharmaceutical composition that contains a MAGL-specific inhibitor of the present invention. The MAGL-specific inhibitor can be used alone or in conjunction with other known therapeutic agents suitable for the disorder. For example, subjects with pain can be additionally administered with other analgesic agents to alleviate pain. Examples of such known analgesic agents include morphine and moxonidine (see, e.g., U.S. Pat. No. 6,117,879). In some other methods, a MAGL-specific inhibitor of the present invention can be used in combination of a FAAH selective inhibitor to enhance endocannabinoid signaling activities in subjects. Compared to MAGL inhibition alone or FAAH inhibition alone, administration of both a MAGL-selective inhibitor and a FAAH-selective inhibitor could potentially better induce in subjects the desired cannabinoid dependent behavioral effects, e.g., a reduction in pain sensation or amelioration of symptoms associated with inflammation, anxiety, and depression. FAAH selective inhibitors are known in the art (e.g., Fegley et al., J. Pharmacol. Exp. Ther. 313: 352-8, 2005. For example, FAAH selective inhibitor URB597 can be readily obtained commercially, e.g., from Cayman Chemicals (Ann Arbor, Mich.).

By way of example, the MAGL-selective inhibitors of the present invention can be used to treat or alleviate symptoms of subjects suffering from pain. Pain is present in many medical disorders. For example, inflammation can induce pain. Examples of inflammatory conditions include osteoarthritis, colitis, carditis, dermatitis, myositis, neuritis, collagen vascular diseases such as rheumatoid arthritis and lupus. Subjects with any of these conditions often experience enhanced sensations of pain. Other medical conditions or procedures that may cause excessive pain include trauma, surgery, amputation, abscess, causalgia, demyelinating diseases, trigeminal neuralgia, chronic alcoholism, stroke, thalamic pain syndrome, diabetes, cancer viral infections, and chemotherapy.

In general, the treatment should allow a subject to obtain a desired pharmacologic and/or physiologic effect. The effect may be prophylactic in terms of completely or partially preventing a subject from developing a condition or disorder associated with cannabinoid signaling or sign or symptom thereof. It can also be therapeutic in terms of a partial or complete cure for condition or disorder associated with cannabinoid signaling and/or adverse effect (e.g., pain) that is attributable to the disorders. Where the subject is a human, the level of pain the person perceives can be assessed by asking him or her to describe the pain or compare it to other painful experiences. Alternatively, pain levels can be calibrated by measuring the subject's physical responses to the pain, such as the release of stress-related factors or the activity of pain-transducing nerves in the peripheral nervous system or the CNS. One can also calibrate pain levels by measuring the amount of a well characterized analgesic required for a person to report that no pain is present or for a subject to stop exhibiting symptoms of pain.

The subjects suitable for the therapeutic methods of the invention can be human subjects, non-human mammals and other animals that express MAGL. The subjects may have an ongoing condition that is currently causing pain and is likely to continue to cause pain. They may also have been or will be enduring a procedure or event that usually has painful consequences. For example, the subject may have chronic painful conditions such as diabetic neuropathic pain or collagen vascular diseases. The subject may also have inflammation, nerve damage, or toxin exposure (including exposure to chemotherapeutic agents). The treatment or intervention is intended to reducing or lessening pain in the subject so that the level of pain the subject perceives is reduced relative to the level of pain the subject would have perceived were it not for the treatment.

In some embodiments, treatment of subjects having neuropathic pain is intended. These subjects can have a neuropathy classified as a radiculopathy, mononeuropathy, mononeuropathy multiplex, polyneuropathy or plexopathy. Diseases in these classes can be caused by a variety of nerve-damaging conditions or procedures, including, without limitation, trauma, stroke, demyelinating diseases, abscess, surgery, amputation, inflammatory diseases of the nerves, causalgia, diabetes, collagen vascular diseases, trigeminal neuralgia, rheumatoid arthritis, toxins, cancer (which can cause direct or remote (e.g. paraneoplastic) nerve damage), chronic alcoholism, herpes infection, AIDS, and chemotherapy. Nerve damage causing pain can be in peripheral or CNS nerves.

In some embodiments of the invention, subjects in need of treatment or alleviation of hyperalgelsia are administered with a composition combining an inhibitor of MAGL with one or more additional pain-reducing agents. This is because an individual pain medication often provides only partially effective pain alleviation because it interferes with just one pain-transducing pathway out of many. However, pain associated with diseases or medical conditions often involves multiple norciceptors and different signaling pathways. Thus, more than one pain-reducing agent may be needed to alleviate norciception in these situations. In some other applications, MAGL inhibitors can be administered in combination with an analgesic agent that acts at a different point in the pain perception process. For example, one class of analgesics, such as NSAIDs (e.g., acetaminophen, ibuprofen and indomethacin), down-regulates the chemical messengers of the stimuli that are detected by the nociceptors. Another class of drugs, such as opioids, alters the processing of nociceptive information in the CNS. Other analgesics such as local anesthetics including anticonvulsants and antidepressants can also be included. Administering one or more classes of drug in addition to MAGL inhibitors can provide more effective amelioration of pain.

V. Screening for Novel MAGL Inhibitors

In addition to the specific MAGL-inhibitors described herein, the invention also provides methods of screening for novel MAGL inhibitors which have improved properties. An important step in the drug discovery process is the selection of a suitable lead chemical template upon which to base a chemistry analog program. The process of identifying a lead chemical template for a given molecular target typically involves screening a large number of compounds (often more than 100,000) in a functional assay, selecting a subset based on some arbitrary activity threshold for testing in a secondary assay to confirm activity, and then assessing the remaining active compounds for suitability of chemical elaboration. The novel MAGL inhibitors described herein, e.g., compounds of formula I, provide lead compounds to search for related compounds that have improved biological or pharmaceutical properties. For example, analogs or derivatives of these MAGL inhibitors can be screened for to identify compounds that have a higher affinity for MAGL or are more penetrant of the skin. Compounds with such improved properties can be more suitable for various pharmaceutical applications.

The screening methods of the invention typically first involve synthesizing analogs, derivatives or variants of a MAGL-selective inhibitor exemplified herein (e.g., JZL184 or JZL175). Once a library of structural analogs of a given MAGL inhibitor is prepared for the screening, a functional assay is then performed to identify one or of the analogs or derivatives that have an improved biological property relative to that of the MAGL inhibitor from which the analogs or variants are derived. For example, the analog compounds of an existing MAGL selective inhibitor can be screened for enhanced inhibitory activity (e.g., reduced $IC_{50}$) for MAGL while preserving its selectivity. Alternatively, the analogs can be screened for enhanced selectivity for MAGL over FAAH and/or ABHD6. They can also be screened for selectivity for MAGL over additional brain serine hydrolases (e.g., ABHD12). In some other embodiments, the analogs can be screened for enhanced binding affinity for a MAGL polypeptide. Moreover, the library of analog compounds can be assayed to identify compounds with better pharmaceutical properties, e.g., skin penetration or pharmacokinetic characters.

In still some other embodiments, the screening methods of the invention are directed to identifying therapeutic agents which can selectively inhibit both FAAH and MAGL. It is possible that behavioral processes (e.g., pain sensation) that are regulated by both AEA and 2-AG could be even more strongly affected by dual MAGL-FAAH inhibitors. As demonstrated in the Examples, at high concentrations, the MAGL selective inhibitors (e.g., JZL184) can also inhibit FAAH without significantly affecting other brain serine hydrolases. Therefore, these compounds can serve as lead chemical scaffolds for the development of dual inhibitors for MAGL and FAAH.

To synthesize analogs or derivatives based from the chemical backbones of the MAGL selective inhibitors exemplified herein, only routinely practiced methods of organic chemistry that are well in the art are required. For example, combinatorial libraries of chemical analogs of a known compound can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Other methods for synthesizing analogs of various compounds are described in, e.g., by Overman, Organic Reactions, Volumes 1-62, Wiley-Interscience (2003); Broom et al., Fed Proc. 45: 2779-83, 1986; Ben-Menahem et al., Recent Prog. Horm. Res. 54:271-88, 1999; Schramm et al., Annu. Rev. Biochem. 67: 693-720, 1998; Bolin et al., Biopolymers 37: 57-66, 1995; Karten et al., Endocr Rev. 7: 44-66, 1986; Ho et al., Tactics of Organic Synthesis, Wiley-Interscience; (1994); and Scheit et al., Nucleotide Analogs: Synthesis and Biological Function, John Wiley & Sons (1980).

Enhanced biological activities or pharmaceutical properties of the library of analog compounds of a given MAGL selective inhibitor can be readily screened with any of the functional assays well known in the art. For example, inhibition of MAGL and other brain serine hydrolases by the compounds can be examined with the enzyme activity assays disclosed herein or those well known in the art, e.g., assaying hydrolysis of cognate substrates by the enzymes present in brain membrane proteomes. MAGL, FAAH as well as other brain serine hydrolases from human and other species are well known in the art. Cloning of their sequences and characterization of their enzymatic and other biological activities have all been reported in the art. See, e.g., Blankman et al., Chem. Biol. 14:1347-56, 2007; Somma-Delpéro et al., Biochem J. 312:519-25, 1995; Dinh et al., Proc. Natl. Acad. Sci. USA 99:10819-24, 2002; Dinh et al., Mol. Pharmacol. 66:1260-4, 2004; Muccioli et al., J. Neurosci. 27:2883-9, 2007; Giang et al., Proc. Natl. Acad. Sci. U.S.A. 94:2238-2242, 1997; Wan et al., Genomics 54:408-414, 1998; Patricelli et al., Bioorg. Med. Chem. Lett. 8:613-618, 1998; and Goparaju et al., Biochim. Biophys. Acta 1441:77-84, 1999.

An improvement in other biological or biochemical activities of the compounds (e.g., enhanced binding affinity for MAGL) can be examined with methods routinely practiced in the art. For a general overview, see, e.g., Sambrook et al., *Molecular Cloning: A Laboratory Manual*, Cold Spring Harbor Press, N.Y., $3^{rd}$ Ed. (2000); Ausubel et al., *Current Protocols in Molecular Biology*, John Wiley & Sons, Inc., New York (1999); and Berger and Kimmel, Methods In Enzymology, San Diego, Academic Press, Inc. (1987). Additional biochemical or pharmaceutical assays that can be employed in the screening methods of the invention are also well known and routinely practiced in the art. For example, skin penetration properties of an analog compound of a MAGL selective inhibitor can be assayed using methods such as those described in, e.g., *Remington: The Science and Practice of Pharmacy*, Gennaro (ed.), Lippincott Williams & Wilkins ($20^{th}$ ed., 2003).

VI. Treating Cancer and Inhibiting Tumor Growth by Targeting MAGL

The present invention provides methods and compositions for inhibiting growth of tumor cells. Typically, these therapeutic applications of the present invention employ a compound that specifically antagonizes or inhibits monoacylglycerol lipase (MAGL). Growth of the tumor cell is inhibited, suppressed or slowed upon contacting the tumor cell with a therapeutically effective amount of the MAGL-antagonizing compound. In some embodiments, the tumor cell is present in a subject, e.g., a subject having or being at risk of developing a cancer. Some preferred embodiments of these therapeutic applications are directed to inhibiting growth of an aggressive tumor or tumor cell.

In some related embodiments, the invention provides methods to treat cancer in a subject by inhibiting growth of tumor cells. The methods are also useful to prevent tumorigenesis in a subject. Typically, the methods involve administering to the subject in need of treatment a pharmaceutical composition that contains a MAGL-antagonizing compound disclosed herein. The MAGL-antagonizing compound can be used alone or in conjunction with other known anti-cancer agents to provide synergistic effects in the subject.

MAGL-antagonizing compounds employed in the invention include any agent that down-regulates cellular level or inhibits a biological activity (e.g., lipase activity) of MAGL. Suitable MAGL-antagonizing compounds also include novel agents that can be identified in accordance with the screening methods described below, e.g., additional small molecule compounds or antibodies (e.g., antagonist antibodies). In some embodiments, the employed MAGL-antagonizing compound for inhibiting tumor growth or treating cancer is an agent (e.g., an inhibitory polynucleotide) that specifically inhibits MAGL expression or down-regulates its cellular level. For example, inhibitory polynucleotides targeting MAGL include short interfering RNA (siRNA), microRNA (miRNA), short hairpin RNA (shRNA), anti-sense nucleic acid, or complementary DNA (cDNA). Using these nucleic acid agents to specifically silence expression of a target gene has been well known and routinely practiced in the art. Such nucleic acid agents that specifically target MAGL can be prepared using methods well known in the art. By way of example, shRNAs and siRNAs targeting a MAGL gene can be utilized to down-regulate MAGL expression level, as demonstrated in the Examples below.

Interference with the function and expression of endogenous genes by double-stranded RNA has been shown in various organisms such as *C. elegans* as described, e.g., in Fire et al., Nature 391:806-811, 1998; drosophilia as described, e.g., in Kennerdell et al., Cell 95:1017-1026, 1998; and mouse embryos as described, e.g., in Wianni et al., Nat. Cell Biol. 2:70-75, 2000. Such double-stranded RNA can be synthesized by in vitro transcription of single-stranded RNA read from both directions of a template and in vitro annealing of sense and antisense RNA strands. Double-stranded RNA can also be synthesized from a cDNA vector construct in which a MAGL gene is cloned in opposing orientations separated by an inverted repeat. Following cell transfection, the RNA is transcribed and the complementary strands reanneal. Double-stranded RNA targeting a MAGL gene can be introduced into a cell (e.g., a tumor cell) by transfection of an appropriate construct. By way of example, sequences of the antisense and sense strands of specific siRNAs and shRNAs which down-regulates MAGL expression are disclosed herein. Additional siRNA or shRNA molecules as well as other types of inhibitory polynucleotides targeting MAGL (e.g., antisense oligonucleotides) can be readily generated in accordance with standard techniques well known in the art.

In some other embodiments, the therapeutic applications of the invention employ MAGL-antagonizing compounds that inhibit a biological activity of MAGL. These include a MAGL selective inhibitor disclosed herein which antagonizes the enzymatic activity of MAGL. Suitable MAGL-antagonizing compounds also include antagonist antibodies which specifically bind to an MAGL polypeptide and antagonize its lipase activity. Monoclonal antibody-based reagents are among those most highly preferred in this regard. Anti-MAGL antagonist antibodies can be generated using methods well known and routinely practiced in the art, e.g., *Monoclonal Antibodies-Production, Engineering And Clinical Applications*, Ritter et al., Eds., Cambridge University Press, Cambridge, UK, 1995; and Harlow and Lane, *Antibodies, A Laboratory Manual*, Cold Spring Harbor Press, $3^{rd}$ ed., 2000. Radiolabeled monoclonal antibodies for cancer therapy, in particular, are well known and are described in, for instance, *Cancer Therapy With Radiolabelled Antibodies*, D. M. Goldenberg, Ed., CRC Press, Boca Raton, Fla., 1995.

Compounds which inhibit or down-regulate MAGL expression or its enzymatic activity can be used in conjunction with other therapies. For example, subjects receiving surgery and radiation therapies can also be administered with a pharmaceutical composition of the present invention. In addition, chemotherapy, hormonal therapy and cryotherapy may also be combined with the therapeutic applications of the present invention to treat subjects suffering from cancers. The MAGL-antagonizing compounds can also be used in a subject to prevent tumor growth or treat cancer together with the administration of other therapeutic compounds for the treatment or prevention of these disorders. When an MAGL-antagonizing compound is administered together with another anti-cancer agent, the two can be administered in either order or simultaneously. These therapeutic compounds may be chemotherapeutic agents, ablation or other therapeutic hormones, antineoplastic agents, monoclonal antibodies useful against cancers and angiogenesis inhibitors.

There are many anti-cancer drugs known in the art, e.g., as described in, e.g., *Cancer Therapeutics: Experimental and Clinical Agents*, Teicher (Ed.), Humana Press ($1^{st}$ ed., 1997); and *Goodman and Gilman's The Pharmacological Basis of Therapeutics*, Hardman et al. (Eds.), McGraw-Hill Professional ($10^{th}$ ed., 2001). Examples of suitable anti-cancer drugs include 5-fluorouracil, vinblastine sulfate, estramustine phosphate, suramin and strontium-89. Examples of suitable chemotherapeutic agents include Asparaginase, Bleomycin Sulfate, Cisplatin, Cytarabine, Fludarabine Phosphate, Mitomycin and Streptozocin. Hormones which may be used in combination with the present invention diethylstilbestrol (DES), leuprolide, flutamide, cyproterone acetate, ketoconazole and amino glutethimide.

Subjects that are suitable for treatment with the methods of the invention are those who are suffering from various types of cancer or those who are at risk or have a predisposition of developing a cancer. Methods of the invention can be employed to inhibit growth of a great number of tumor cells. Examples of tumors or cancers amenable to treatment include tumors originated from lung, skin, breast, brain, gastrointestinal, genitourinary tract (e.g., kidney, bladder and urethra, prostate, testis), blood, the nervous system, bone and liver. They encompass solid tumors, leukemia and metastatic tumors. Solid tumors suitable for the invention include, e.g., sarcoma, melanoma, carcinoma, or other solid tumor cancer.

Sarcoma encompasses tumors made up of a substance like the embryonic connective tissue and is generally composed of closely packed cells embedded in a fibrillar or homogeneous substance. Sarcomas include, but are not limited to, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Melanoma refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

Carcinoma refers to a malignant new growth made up of epithelial cells tending to infiltrate the surrounding tissues and give rise to metastases. Exemplary carcinomas further include, for example, epithelial cancer, colorectal carcinoma, gastric carcinoma, oral carcinoma, pancreatic carcinoma, ovarian carcinoma, or renal cell carcinoma. Exemplary carcinomas further include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma viflosum.

Leukemia encompasses progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.[0001]

Other cancer or tumors that can be treated with methods of the invention include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

VII. Pharmaceutical Compositions and Administration

The invention provides the use of a MAGL antagonist compound (e.g., a MAGL selective inhibitor) in the manufacture of a medicament for treating a condition or disorder that is mediated by or associated with endocannabinoid signaling. In some related applications, MAGL-antagonizing compounds are used for inhibiting growth of tumor cells and for treating cancers. In these therapeutic applications, subjects in need of treatment can be administered with a MAGL antagonist compound alone. However, the administration of a pharmaceutical composition that contains the MAGL-antagonist compound or a pharmaceutically acceptable salt thereof is more preferred. Examples of MAGL-antagonist compounds that can be employed in the pharmaceutical compositions include small organic compounds JZL184, JZL175, WWL152 and WWL162, as well as inhibitory polynucleotides described in the Examples below. Novel MAGL inhibitors that can be identified in accordance with the screening methods of the invention can also be used. The invention also provides for a pharmaceutical combination, e.g. a kit. Such pharmaceutical combination can contain an active agent which is a MAGL antagonist compound disclosed herein, in free form or in a composition, at least one co-agent, as well as instructions for administration of the agents.

The pharmaceutical compositions that comprise a MAGL selective inhibitor can be prepared in various forms. Suitable solid or liquid pharmaceutical preparation forms are, e.g., granules, powders, tablets, coated tablets, (micro)capsules, suppositories, syrups, emulsions, suspensions, creams, aerosols, drops or injectable solution in ampule form and also preparations with protracted release of active compounds. They can be prepared in accordance with the standard protocols well known in the art, e.g., *Remington: The Science and Practice of Pharmacy*, Gennaro (ed.), Lippincott Williams & Wilkins ($20^{th}$ ed., 2003). The pharmaceutical compositions typically contain an effective amount of the MAGL antagonist compound that is sufficient to inhibit tumor growth or to lessen or ameliorate symptoms of a disorder or condition that is associated with or mediated by 2-AG signaling. In addition to the MAGL antagonist compound, the pharmaceutical compositions can also contain certain pharmaceutically acceptable carriers which enhance or stabilize the composition, or facilitate preparation of the composition. For example, the MAGL antagonist compound can be complexed with carrier proteins such as ovalbumin or serum albumin prior to their administration in order to enhance stability or pharmacological properties. The various forms of pharmaceutical compositions can also contain excipients and additives and/or auxiliaries such as disintegrants, binders, coating agents, swelling agents, lubricants, flavorings, sweeteners and elixirs containing inert diluents commonly used in the art, such as purified water.

Pharmaceutically acceptable carriers are determined in part by the particular composition being administered as well as by the particular method used to administer the composition. They should also be both pharmaceutically and physiologically acceptable in the sense of being compatible with the other ingredients and not injurious to the subject. The carrier may take a wide variety of forms depending on the form of preparation desired for administration, e.g., oral, sublingual, rectal, nasal, intravenous, or parenteral. For example, examples of non-aqueous solvents are propylene glycol, polyethylene glycol, vegetable oils such as olive oil, and injectable organic esters such as ethyl oleate. Carriers for occlusive dressings can be used to increase skin permeability and enhance absorption. Liquid dosage forms for oral administration may generally comprise a liposome solution containing the liquid dosage form.

Pharmaceutical composition containing a MAGL inhibiting compound can be administered locally or systemically in a therapeutically effective amount or dose. They can be administered parenterally, enterically, by injection, rapid infusion, nasopharyngeal absorption, dermal absorption, rectally and orally. A therapeutically effective amount means an amount that that is sufficient to reduce or inhibit a symptom (e.g., nociceptive pain) of the disorder or condition to be treated in a subject. Such effective amount will vary from subject to subject depending on the subject's normal sensitivity to pain, its height, weight, age, and health, the source of the pain, the mode of administering the MAGL antagonist compound, the particular inhibitor administered, and other factors. As a result, it is advisable to empirically determine an effective amount for a particular subject under a particular set of circumstances.

For a given MAGL antagonist compound, one skilled in the art can easily identify by using routinely practiced pharmaceutical methods the effective amount of the compound that inhibits tumor growth and treat cancer, or the effective amount of the compound that treats a condition associated with cannabinoid signaling. Typically, dosages used in vitro may provide useful guidance in the amounts useful for in situ administration of the pharmaceutical composition, and animal models may be used to determine effective dosages for treatment of particular disorders in human subjects. More often, a suitable therapeutic dose can be determined by clinical studies on mammalian species to determine maximum tolerable dose and on normal human subjects to determine safe dosage. Except under certain circumstances when higher dosages may be required, the preferred dosage of a MAGL-antagonist compound usually lies within the range of from about 0.001 to about 1000 mg, more usually from about 0.01 to about 500 mg per day. As a general rule, the quantity of a MAGL-antagonist compound administered is the smallest dosage which effectively and reliably prevents or minimizes the conditions of the subjects. Therefore, the above dosage ranges are intended to provide general guidance and support for the teachings herein, but are not intended to limit the scope of the invention. Additional guidance for preparation and administration of the pharmaceutical compositions of the invention has also been described in the art. See, e.g., *Goodman & Gilman's The Pharmacological Bases of Therapeutics*, Hardman et al., eds., McGraw-Hill Professional ($10^{th}$ ed., 2001); *Remington: The Science and Practice of Pharmacy*, Gennaro, ed., Lippincott Williams & Wilkins ($20^{th}$ ed., 2003); and *Pharmaceutical Dosage Forms and Drug Delivery Systems*, Ansel et al. (eds.), Lippincott Williams & Wilkins ($7^{th}$ ed., 1999).

EXAMPLES

The following examples are offered to illustrate, but not to limit the present invention.

Example 1

Development of Selective Inhibitors of MAGL

The pursuit of selective inhibitors for serine hydrolases has the potential to benefit from multiple features special to this enzyme class. First, serine hydrolases are susceptible to covalent inactivation by specific chemical groups that show little or no cross-reactivity with other enzyme classes. Principal among these reactive chemotypes is the carbamate, which has been identified as a privileged scaffold for the design of selective, irreversible inhibitors of serine hydrolases owing to its tempered electrophilicity and hydrolytic stability following covalent reaction (carbamylation) with the conserved serine nucleophile of these enzymes. Second, the functional state of serine hydrolases can be collectively profiled in native biological systems using activity-based protein profiling (ABPP) methods (Cravat et al., *Annu Rev Biochem* 77:383-414, 2008). ABPP of serine hydrolases uses reporter-tagged fluorophosphonates (FPs), which serve as general activity-based probes for this large and diverse enzyme class (Liu et al., *Proc. Natl. Acad. Sci. U.S.A.* 96:14694-9, 1999). When performed in a competitive mode, ABPP can serve as a powerful screen to evaluate the potency and selectivity of small-molecule enzyme inhibitors directly in complex proteomes. The screen can be performed as described in the art, e.g., Liu et al., *Proc. Natl. Acad. Sci. U.S.A.* 96:14694-9, 1999; Li et al., *J. Am. Chem. Soc.* 129:9594-5, 2007; Leung et al., *Nat. Biotech.* 21:687-91, 2003; and Greenbaum et al., *Mol. Cell. Proteomics* 1:60-68, 2002.

Figure 6:
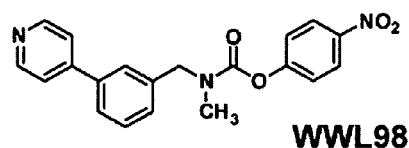
FIGS. 6A-6B show structure of compound WWL98 (A) and synthetic route for compound JZL184 (B). Other carbamate inhibitors were synthesized by a similar route.
Figure 6:
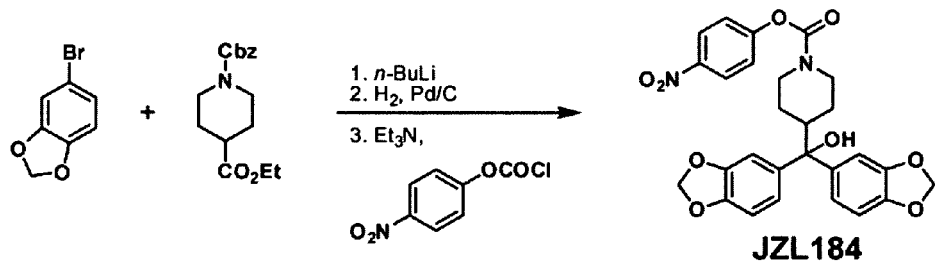

In the course of performing competitive ABPP screens with a structurally diverse library of carbamates, we identified the compound WWL98 (FIG. 6), which inhibited a specific subset of brain serine hydrolases that included FAAH, MAGL and, ABHD6 (FIG. 1B). We next focused on modifying WWL98 to improve potency and selectivity for MAGL. The incorporation of a piperazine spacer and a distal bisaryl motif, as represented in WWL152 and WWL162 (FIG. 1A), was found to preserve potency for MAGL and ABHD6, while greatly reducing activity for FAAH (FIG. 1B). Replacement of the piperazine with a piperidinyl methanol scaffold afforded JZL175 (FIG. 1A), a compound that exhibited selectivity for MAGL over both FAAH and ABHD6 (FIG. 1B). Finally, an additional enhancement in selectivity was achieved by inclusion of bis(methylene-3,4-dioxyphenyl) groups on the piperidinyl methanol scaffold to provide JZL184 (FIGS. 1A and B).

Example 2

Activity of MAGL Selective Inhibitors in Brain Proteomes

Figure 2:
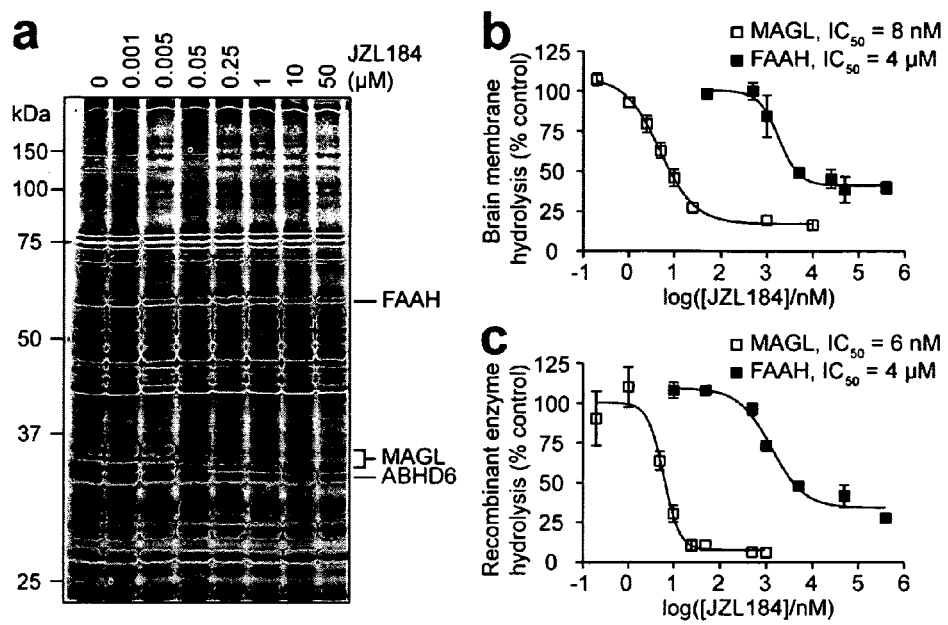
FIGS. 2A-2C show 2 in vitro characterization of JZL184. A: Concentration-dependent effects of JZL184 on mouse brain membrane serine hydrolases as determined by competitive ABPP; B: Blockade of brain membrane MAGL and FAAH activity by JZL184 as determined with substrate assays (2-AG and oleamide, respectively); C: Blockade of recombinant MAGL and FAAH activity by JZL184 as determined with substrate assays (2-AG and anandamide, respectively). Enzymes were recombinantly expressed in COS7 cells. Note that JZL184 produced a near-complete blockade of recombinant MAGL activity (>95%), but ~15% residual 2-AG hydrolysis activity was observed in brain membranes, likely reflecting the activity of other enzymes[26]. For A-C, samples were treated with JZL184 for 30 min prior to analysis. For B and C, data are presented as means±SEM for three independent experiments.
Figure 7:
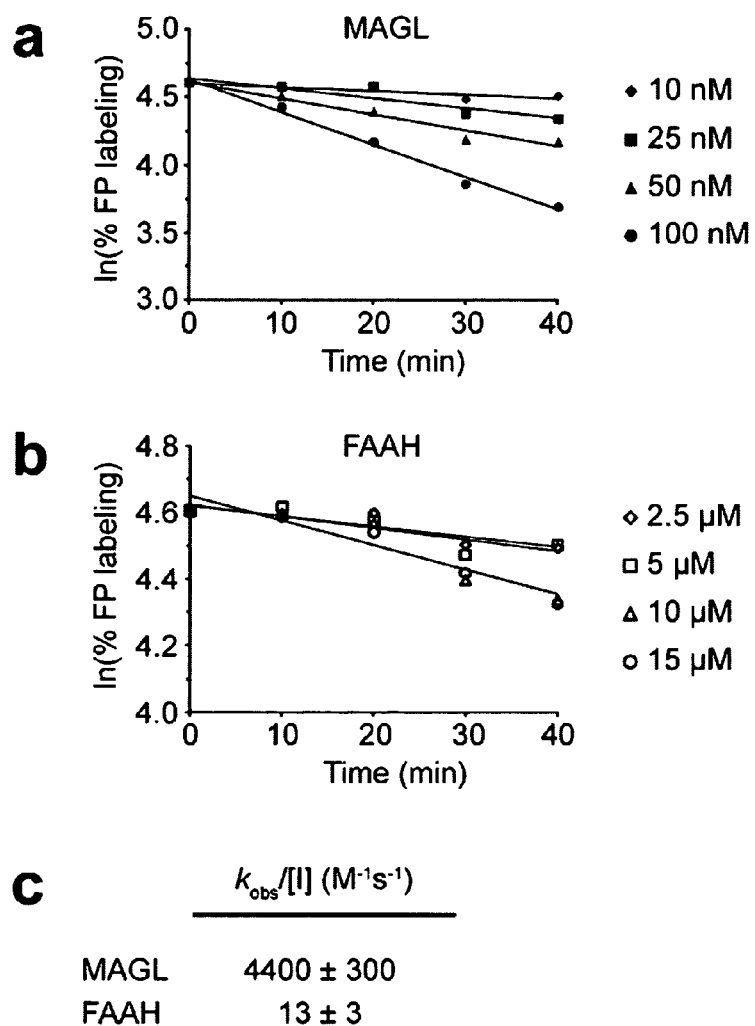
FIGS. 7A-7C show time-dependent inhibition of MAGL and FAAH by JZL184. A: JZL184 inhibition of FP-rhodamine labeling of MAGL activity in mouse brain membrane proteome; B: JZL184 inhibition of FP-rhodamine labeling of MAGL activity in mouse brain membrane proteome; C: $k_{obs}/[I]$ values calculated for inhibition of MAGL and FAAH by JZL184.
Figure 8:
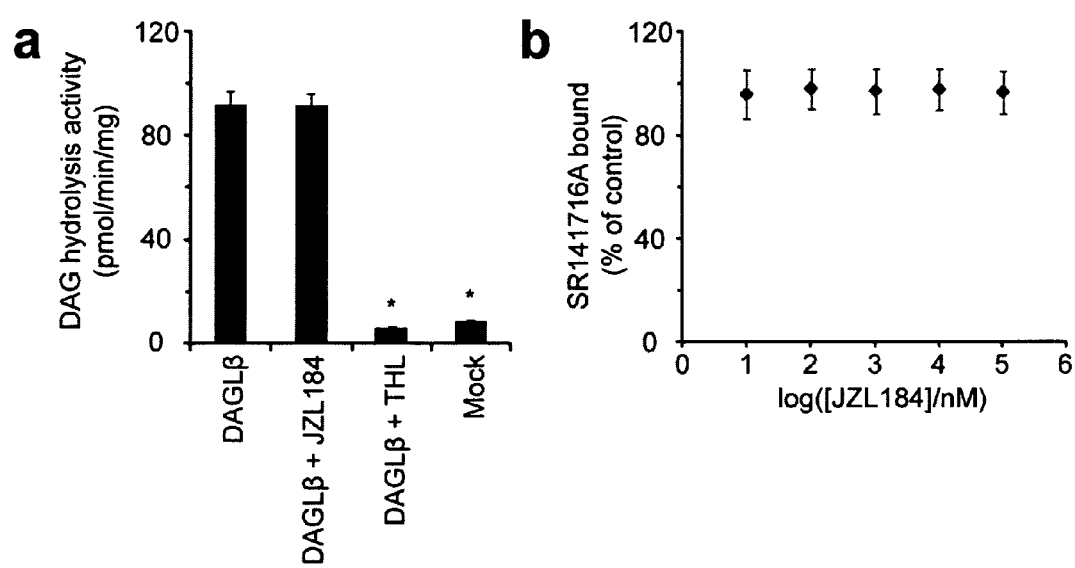
FIGS. 8A-8B show that compound JZL184 does not bind to CB1 receptors or inhibit the 2-AG biosynthetic enzyme DAGLβ. A: JZL184 did not displace binding of $^3$H-rimonabant from CB1 receptors; B: JZL184 (25 μM) did not inhibit DAGLβ recombinantly expressed in COS-7 cells. The known DAGLβ inhibitor tetrahydrolipstatin (THL, 25 μM) was used as a positive control.

Near-complete blockade of MAGL activity was observed by competitive ABPP following a 30 min preincubation of a mouse brain membrane proteome with as low as 50 nM JZL184 (FIG. 2A). In contrast, inhibition of other enzymes (FAAH, ABHD6) was not observed until much higher concentrations of JZL184 (10 µM). Substrate assays confirmed this degree of selectivity, as JZL184 displayed $IC_{50}$ values of 8 nM and 4 µM for blockade of 2-AG and oleamide (FAAH substrate) hydrolysis in brain membranes, respectively (FIG. 2B). Comparable inhibitory effects were observed with recombinant MAGL and FAAH when expressed in COS7 cells (FIG. 2C). Interestingly, brain membranes maintained a residual ~15% 2-AG hydrolysis activity even at the highest concentrations of JZL184 tested, likely reflecting the contribution of other 2-AG hydrolases that are insensitive to JZL184. JZL184 displayed time-dependent inhibition of MAGL (FIG. 7), indicative of a covalent mechanism of inactivation. We therefore also evaluated the relative activity of JZL184 for MAGL and FAAH by measuring $k_{obs}$[I] values, which confirmed >300-fold selectivity for inhibition of MAGL (4400 and 13 $M^{-1}$ $s^{-1}$, respectively). Finally, we tested JZL184 for activity on other components of the endocannabinoid system. The compound did not interact with the $CB_1$ receptor or inhibit the 2-AG biosynthetic enzyme diacylglycerol lipase-β (FIG. 8). Collectively, these data indicate that JZL184 potently and selectively inactivates MAGL in the mouse brain proteome.

Example 3

In Vivo Activity of MGCL Selective Inhibitors

Figure 3:
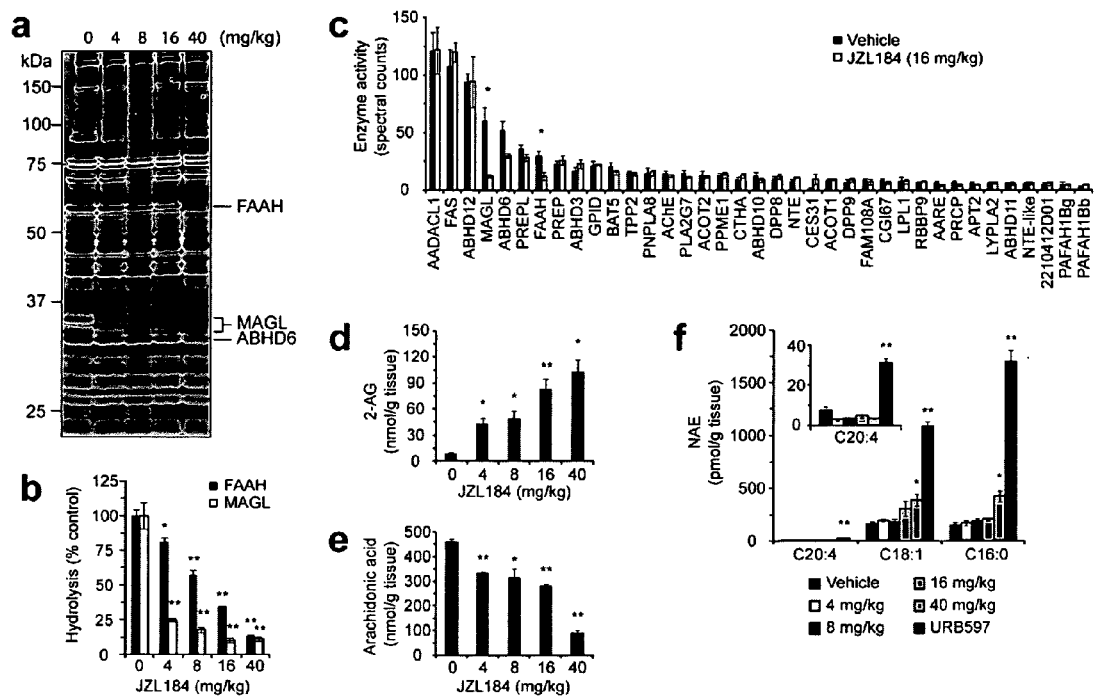
FIGS. 3A-3F show in vivo characterization of JZL184. A and B: Serine hydrolase activity profiles (A) and MAGL and FAAH activities (B) of brain membranes prepared from mice treated with JZL184 at the indicated doses (4-40 mg/kg, i.p.) for 4 hrs; C: ABPP-MudPIT analysis of serine hydrolase activities in brain membranes prepared from mice treated with JZL184 (16 mg/kg, i.p., 4 hrs). MAGL and FAAH control signals are shown in red and blue bars, respectively; D-F: Brain levels of 2-AG (D), arachidonic acid (E), and NAEs (F) from mice treated with JZL184 at the indicated doses (4-40 mg/kg, i.p.) for 4 hrs. For F, data from mice treated with URB597 (10 mg/kg, i.p.) are also shown, confirming the elevations of NAEs induced by this FAAH inhibitor. For B-F, *, $p<0.05$; **, $p<0.01$ for inhibitor-treated versus vehicle-treated animals. Data are presented as means±SEM. n=3-5 mice per group.

To assess the ability of JZL184 to block MAGL in vivo, male C57B1/6 mice were administered JZL184 (4-40 mg/kg, i.p.) and sacrificed after 4 hrs for analysis. At the lowest dose of JZL184 tested (4 mg/kg), competitive ABPP of brain membrane proteomes revealed 75% MAGL inactivation with minimal effects (<20% inhibition) on other brain serine hydrolases, including FAAH (FIG. 3A). These data were also confirmed for MAGL and FAAH by substrate assays (FIG. 3B). Residual brain 2-AG hydrolysis activity could be further reduced from 25% to 15% of control values by increasing the dose of JZL184 from 4 to 16 mg/kg (FIG. 3B), which correlated with a near-complete blockade of MAGL activity as determined by competitive ABPP (FIG. 3A). FAAH was also inhibited in a dose-dependent manner, but even at 16 mg/kg of JZL184, a substantial fraction of FAAH activity (~35%) remained intact as determined by competitive ABPP (FIG. 3A) or substrate (FIG. 3B) assays.

Although our gel-based ABPP analysis already suggested high selectivity for MAGL in vivo, the limited resolution of this method precluded a complete assessment of the functional state of brain serine hydrolases in JZL184-treated animals. We therefore examined brain proteomes using an advanced liquid chromatography-mass spectrometry (LC-MS) platform, termed ABPP-MudPIT, that displays enhanced resolution and sensitivity compared to gel-based ABPP (see, e.g., Jessani et al., Nat. Methods 2:691-7, 2005). ABPP-MudPIT has been previously used to identify unanticipated targets for inhibitors of other components of the endocannabinoid system, including transporters and biosynthetic enzymes. Briefly, brain membrane proteomes from mice treated with JZL184 or vehicle were subjected to competitive ABPP with the biotinylated FP probe, FP-biotin. FP-biotin-labeled proteins were then enriched with avidin, digested on-bead with trypsin, analyzed by multidimensional LC-MS, and identified using the SEQUEST search algorithm. ABPP-MudPIT confirmed that JZL184 (16 mg/kg, 4 hr) produced a near-complete blockade of MAGL activity and partial inhibition of FAAH (FIG. 3C). Strikingly, none of the other ~40 brain serine hydrolases profiled by ABPP-MudPIT were significantly affected by JZL184 (FIG. 3C and Table 1). These data demonstrate that, even when administered at a high dose (16 mg/kg) for an extended period of time (4 hours), JZL184 maintains exceptional selectivity for MAGL in brain.

TABLE 1

Brain membrane serine hydrolase enzymes used in ABPP-MudPIT study

| ENSEMBL Identifier | Common Name | Abbreviation | VEH | JZL184 | p-value |
| --- | --- | --- | --- | --- | --- |
| ENSMUSG00000027698 | Arylacetamide deacetylase-like 1 | AADACL1 | 121.3 ± 16.1 | 121.6 ± 20.4 | 0.990 |
| ENSMUSG00000025153 | Fatty acid synthase | FAS | 108 ± 14.8 | 120.3 ± 8.1 | 0.507 |
| ENSMUSG00000032046 | Alpha/beta hydrolase domain containing 12 | ABHD12 | 94.3 ± 7.6 | 94.3 ± 21.8 | 1.000 |
| ENSMUSG00000033174 | Monoacylglycerol lipase | MAGL | 59.6 ± 12.8 | 12.3 ± 1.2 | 0.021 |
| ENSMUSG00000025277 | Alpha/beta hydrolase domain containing 6 | ABHD6 | 52.3 ± 8.3 | 30.3 ± 1.8 | 0.062 |
| ENSMUSG00000024127 | Prolyl endopeptidase-like | PREPL | 36.6 ± 2.9 | 28.6 ± 3.1 | 0.139 |
| ENSMUSG00000034171 | Fatty acid amide hydrolase | FAAH | 30 ± 4.7 | 12.3 ± 3.2 | 0.037 |
| ENSMUSG00000019849 | Prolyl endopeptidase | PREP | 23.3 ± 2.3 | 26.3 ± 3.8 | 0.541 |
| ENSMUSG00000002475 | Alpha/beta hydrolase domain containing 3 | ABHD3 | 17.3 ± 2.9 | 23 ± 4.0 | 0.319 |
| ENSMUSG00000070889 | Glycerophosphoinositol deacylase | GPID | 22 ± 3.5 | 22.3 ± 0.3 | 0.929 |
| ENSMUSG00000007036 | HLA-B associated transcript 5 | BAT5 | 21.6 ± 2.6 | 15.6 ± 2.1 | 0.157 |
| ENSMUSG00000041763 | Tripeptidylpeptidase 2 | TPP2 | 16 ± 1.0 | 14.3 ± 1.4 | 0.398 |
| ENSMUSG00000036257 | Patain-like phospholipase domain containing 8 | PNPLA8 | 15.3 ± 4.6 | 15.6 ± 2.3 | 0.952 |
| ENSMUSG00000023328 | Acetylcholinesterase | AChE | 15.3 ± 1.6 | 13 ± 1.0 | 0.296 |
| ENSMUSG00000023913 | Phospholipase A2 group 7 | PLA2G7 | 15 ± 2.5 | 11.6 ± 0.6 | 0.270 |
| ENSMUSG00000021226 | Acyl-CoA thioesterase 2 | ACOT2 | 14.3 ± 2.6 | 12.3 ± 0.8 | 0.507 |
| ENSMUSG00000030718 | Protein phosphatase methylesterase 1 | PPME1 | 13.6 ± 1.7 | 13.6 ± 2.3 | 1.000 |
| ENSMUSG00000017760 | Cathepsin A | CTHA | 10 ± 1.5 | 13.3 ± 2.0 | 0.259 |
| ENSMUSG00000033157 | Alpha/beta hydrolase domain containing 10 | ABHD10 | 13.3 ± 2.3 | 9 ± 2.0 | 0.238 |
| ENSMUSG00000032393 | Dipeptidylpeptidase 8 | DPP8 | 10.6 ± 2.0 | 12.3 ± 2.1 | 0.606 |
| ENSMUSG00000004565 | Neuropathy target esterase | NTE | 8 ± 1.7 | 11.6 ± 0.3 | 0.106 |
| ENSMUSG00000069922 | Carboxylesterase 31 | CES31 | 1.6 ± 1.6 | 10 ± 4.3 | 0.149 |
| ENSMUSG00000072949 | Acyl-CoA thioesterase 1 | ACOT1 | 9 ± 1.1 | 10 ± 0.5 | 0.482 |
| ENSMUSG00000001229 | Dipeptidylpeptidase 9 | DPP9 | 7.6 ± 2.3 | 9.3 ± 1.7 | 0.599 |

TABLE 1-continued

Brain membrane serine hydrolase enzymes used in ABPP-MudPIT study

| ENSEMBL Identifier | Common Name | Abbreviation | VEH | JZL184 | p-value |
|---|---|---|---|---|---|
| ENSMUSG00000003346 | FAM108A1 | FAM108A1 | 9.3 ± 0.8 | 7.6 ± 2.3 | 0.541 |
| ENSMUSG00000047368 | CGI67 | CGI67 | 9 ± 1.5 | 7 ± 1.5 | 0.407 |
| ENSMUSG00000039246 | Lysophospholipase-like 1 | LPL1 | 8.3 ± 3.7 | 8 ± 2.0 | 0.942 |
| ENSMUSG00000027428 | Retinoblastoma binding protein 9 | RBBP9 | 7.6 ± 0.3 | 8 ± 0.0 | 0.374 |
| ENSMUSG00000032590 | Acylaminoacid releasing enzyme | AARE | 7.3 ± 1.3 | 4.6 ± 0.6 | 0.148 |
| ENSMUSG00000061119 | Prolylcarboxypeptidase | PRCP | 7.3 ± 1.2 | 4.6 ± 1.2 | 0.192 |
| ENSMUSG00000028670 | Acyl protein thioesterase 2 | APT2 | 6.6 ± 1.2 | 5 ± 0.0 | 0.238 |
| ENSMUSG00000031903 | 1-O-acylceramide synthase | LYPLA3 | 6.3 ± 0.8 | 6.6 ± 0.6 | 0.778 |
| ENSMUSG00000040532 | Alpha/beta hydrolase domain containing 11 | ABHD11 | 6.3 ± 0.3 | 5.6 ± 1.2 | 0.621 |
| ENSMUSG00000036833 | Neuropathy target esterase-like | NTE-like | 6 ± 1.0 | 6 ± 1.1 | 1.000 |
| ENSMUSG00000038459 | 2210412D01 | 2210412D01 | 5.3 ± 1.3 | 6 ± 1.7 | 0.776 |
| ENSMUSG00000005447 | Platelet activating factor acetylhydrolase 1B gamma | PAFAH-1Bg | 5.6 ± 1.3 | 3.6 ± 2.3 | 0.498 |
| ENSMUSG00000003131 | Platelet activating factor acetylhydrolase 1B beta | PAFAH-1Bb | 2.6 ± 1.3 | 5 ± 1.0 | 0.234 |

Figure 9:
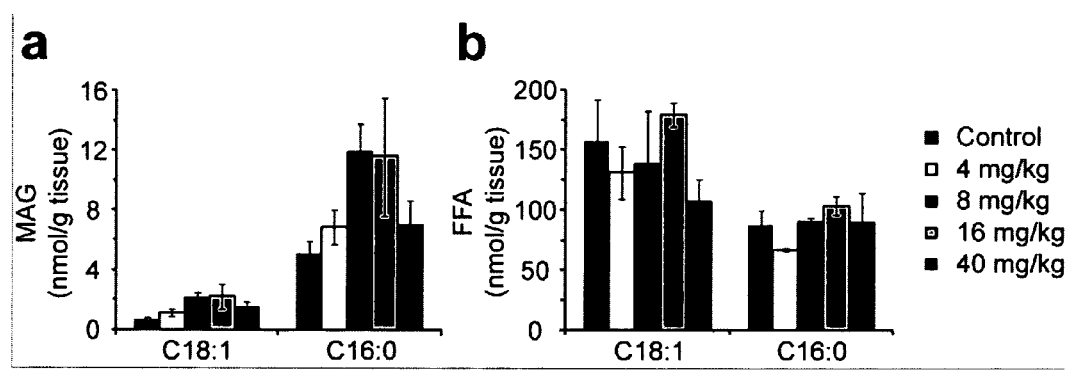
FIGS. 9A-9B show brain lipid measurements for dose-response study of JZL184. No significant changes were observed in brain levels of C18:1 or C16:0 MAGs (A) or free fatty acids (B) was observed at 4 hrs following administration of JZL184 (4-40 mg/kg, i.p.).
Figure 10:
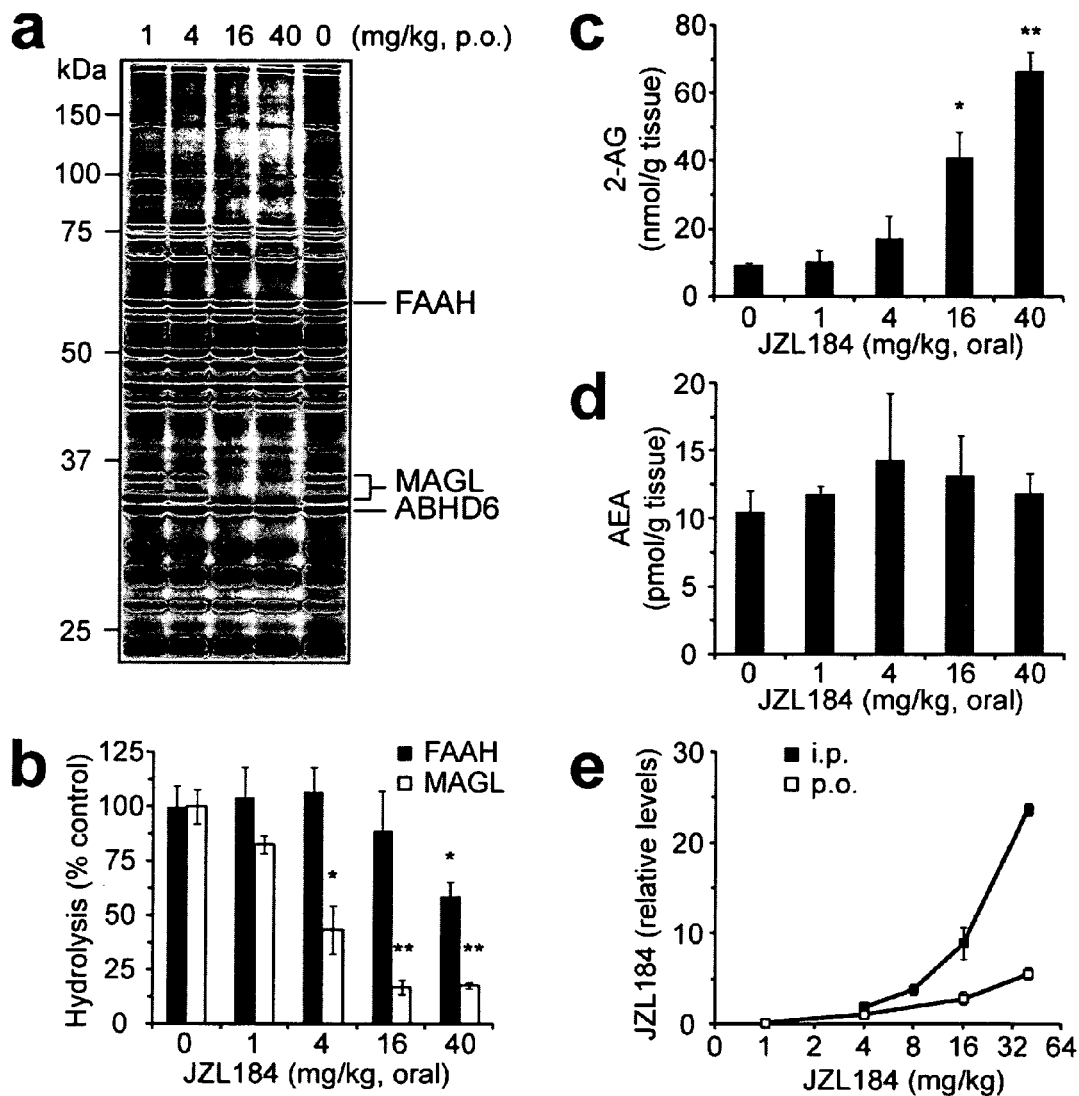
FIGS. 10A-10E show effects of oral administration of JZL184. A and B: Serine hydrolase activity profiles (A) and MAGL and FAAH activities (B) of brain membranes prepared from mice treated with JZL184 at the indicated doses (1-40 mg/kg, p.o.) for 4 hrs; C and D: Brain levels of 2-AG (C) and AEA (D) from mice treated with JZL184 (1-40 mg/kg, p.o.) for 4 hrs; E: Relative brain levels of JZL184 from mice treated either by i.p. or p.o. administration. For B-D, *, $p<0.05$; **, $p<0.01$ for inhibitor-treated versus vehicle-treated animals. Data are presented as means±SEM. n=3-5 mice per group.

Having established the selectivity profile of JZL184 in vivo, we next measured brain levels of candidate endogenous substrates and products for MAGL and FAAH. Even at the lowest dose of JZL184 tested (4 mg/kg), 2-AG levels were elevated by 5-fold at 4 hrs post-treatment and could be further elevated to 8-10-fold above baseline at higher doses of inhibitor (FIG. 3d). As expected, elevations in brain 2-AG were accompanied by significant reductions in the levels of arachidonic acid (FIG. 3E). Other MAGs, such as mono-palmitoylglycerol (PG) and mono-oleoylglycerol (OG), and their corresponding free fatty acids (palmitic and oleic acid, respectively) were not significantly altered in brains from JZL184-treated animals (FIG. 9). Importantly, brain anandamide levels were also unaffected by JZL184 at all of the doses tested (FIG. 3F). Other N-acyl ethanolamines (NAE), such as N-palmitoyl ethanolamine (PEA), and N-oleoyl ethanolamine (OEA), did not change except at the highest dose of JZL184 tested (40 mg/kg), where modest (~2-fold) elevations in these lipids were observed. The lack of impact of JZL184 on NAE levels is consistent with published studies showing that partial disruption of FAAH is insufficient to raise NAE levels in vivo. The lipid profiles of JZL184-treated mice contrasted sharply with those induced by the selective FAAH inhibitor URB597, which completely inhibited brain FAAH activity and caused significant elevations in anandamide and other NAEs without altering 2-AG or arachidonic acid levels in this tissue (FIG. 3F). Similar data were also obtained following oral administration of JZL184 (FIG. 10), indicating that this compound can be administered by multiple routes to achieve selective blockade of MAGL in vivo.

Example 4

Rapid and Persistent Inhibition of MAGL in JZL184-treated Mice

Figure 4:
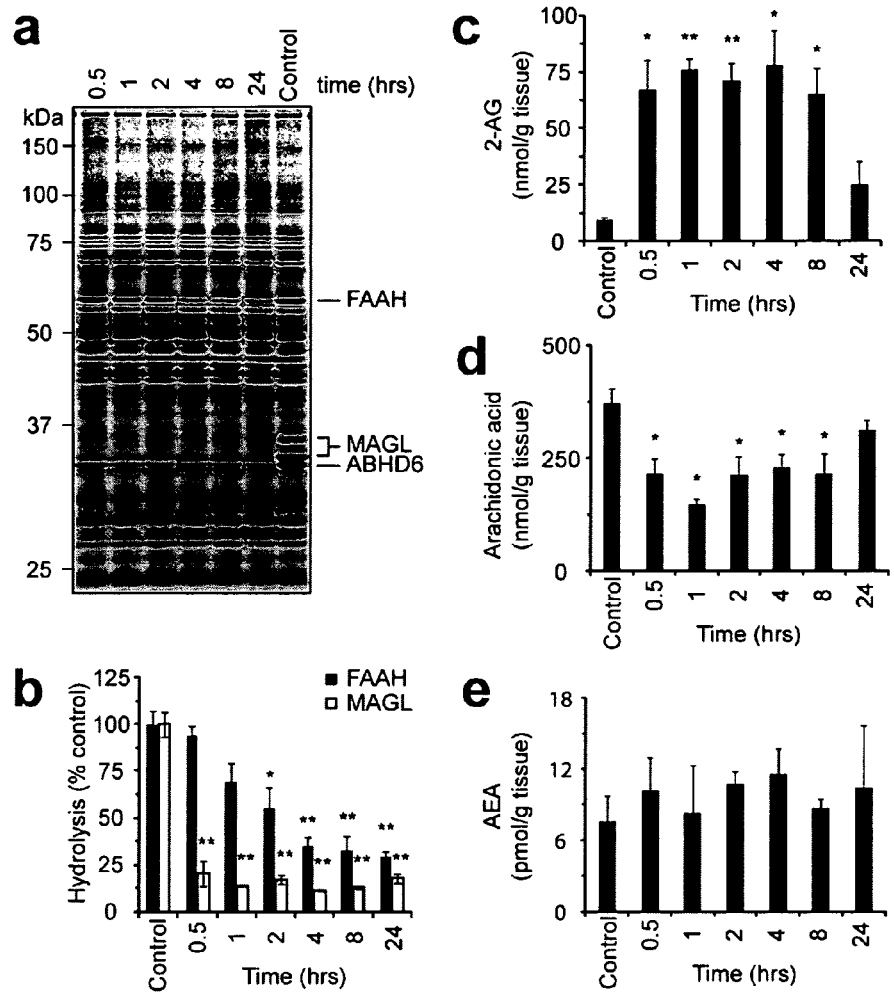
FIGS. 4A-4E show time course analysis of inhibitory activity of JZL184 in vivo. A and B: Serine hydrolase activity profiles (A) and MAGL and FAAH activities (B) of brain membranes prepared from mice treated with JZL184 (16 mg/kg, i.p.) for the indicated times; C-E: Brain levels of 2-AG (C), arachidonic acid (D), and AEA (E) from mice treated with JZL184 (16 mg/kg, i.p.) for the indicated times. For B-E, *, $p<0.05$; **, $p<0.01$ for inhibitor-treated versus vehicle-treated control animals. Data are presented as means±SEM. n=3-5 mice per group.
Figure 11:
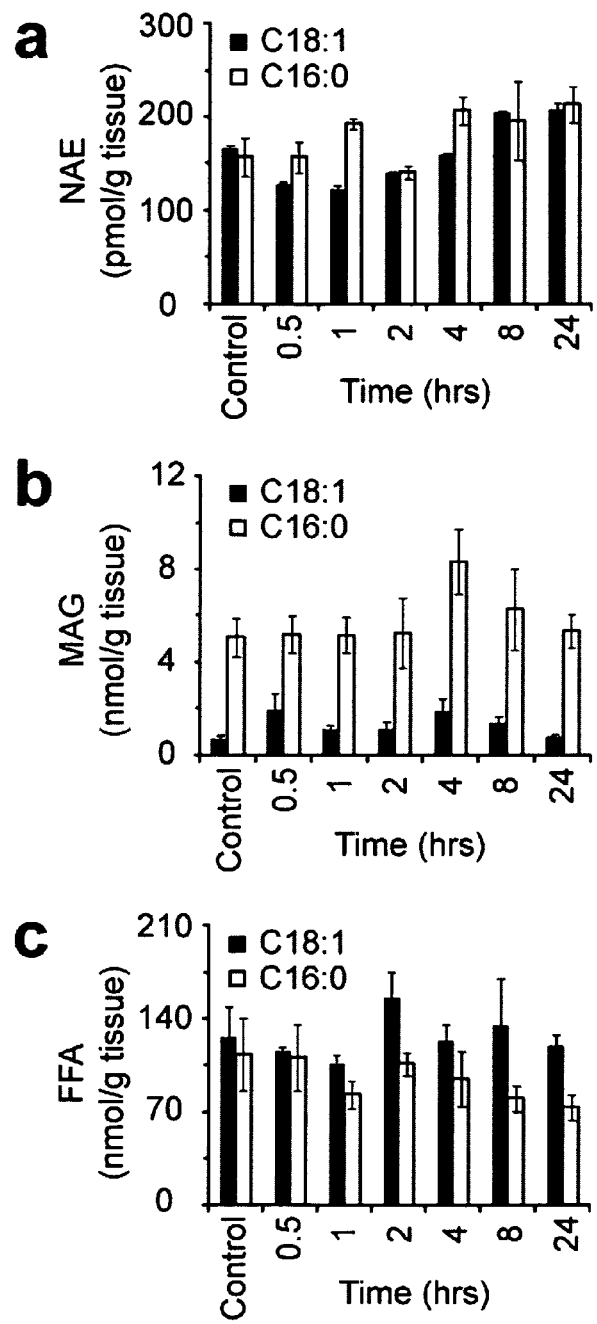
FIGS. 11A-11C show time course of brain lipid measurements following JZL184 treatment in mice. No significant changes were observed in brain levels of C18:1 or C16:0 NAEs (A), MAGs (B), or free fatty acids (C) throughout a 24 hr time course following administration of JZL184 (16 mg/kg, i.p.).
Figure 12:
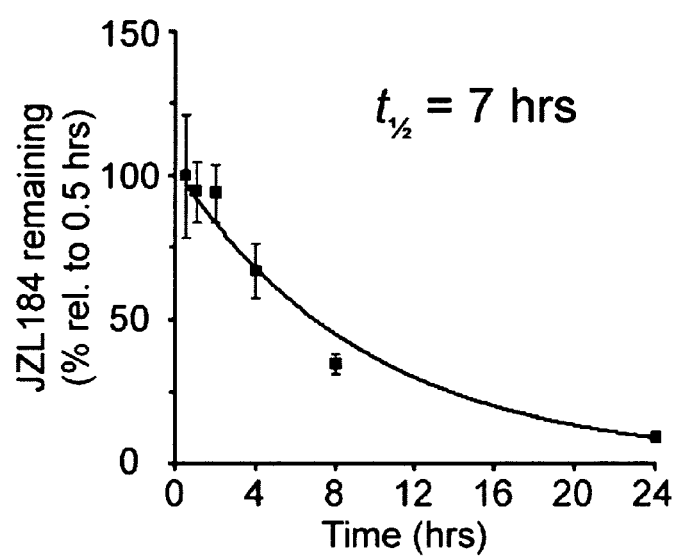
FIG. 12 shows time course analysis of JZL184 levels in mouse brain. JZL184 was administered at 16 mg/kg, i.p.

To determine the time course of JZL184 inhibition in vivo, mice were administered JZL184 (16 mg/kg, i.p.) and sacrificed at 0.5, 1, 2, 4, 8, and 24 hrs for analysis. ABPP of brain membrane proteomes (FIG. 4A) as well as 2-AG and oleamide hydrolysis assays (FIG. 4B) indicated that MAGL inhibition was rapid, with maximal inhibition achieved within 30 min post-treatment, and long-lasting, with >80% inhibition of 2-AG hydrolysis activity persisting for at least 24 hrs (FIG. 4A). In contrast, FAAH blockade occurred much more slowly and never exceeded 70% at any time point examined (FIG. 4B). Concomitant with the rapid inhibition of MAGL, JZL184 treatment caused swift accumulation of 2-AG in the brain. By 30 min, brain 2-AG levels were already elevated 7-fold and remained 7-9-fold above control levels for at least 8 hrs (FIG. 4C). Interestingly, 2-AG levels returned to near-control levels by 24 hrs, even though >80% of the activity of MAGL remained inhibited at this time point. Elevations in 2-AG were matched by a rapid and sustained decrease in arachidonic acid (FIG. 4D). NAEs, including anandamide, as well as other MAGs and free fatty acids were unchanged throughout the time course analysis of JZL184-treated mice (FIG. 4E and FIG. 11).

Example 5

Behavioral Effects Induced by MAGL Selective Inhibitor in Mice

Figure 5:
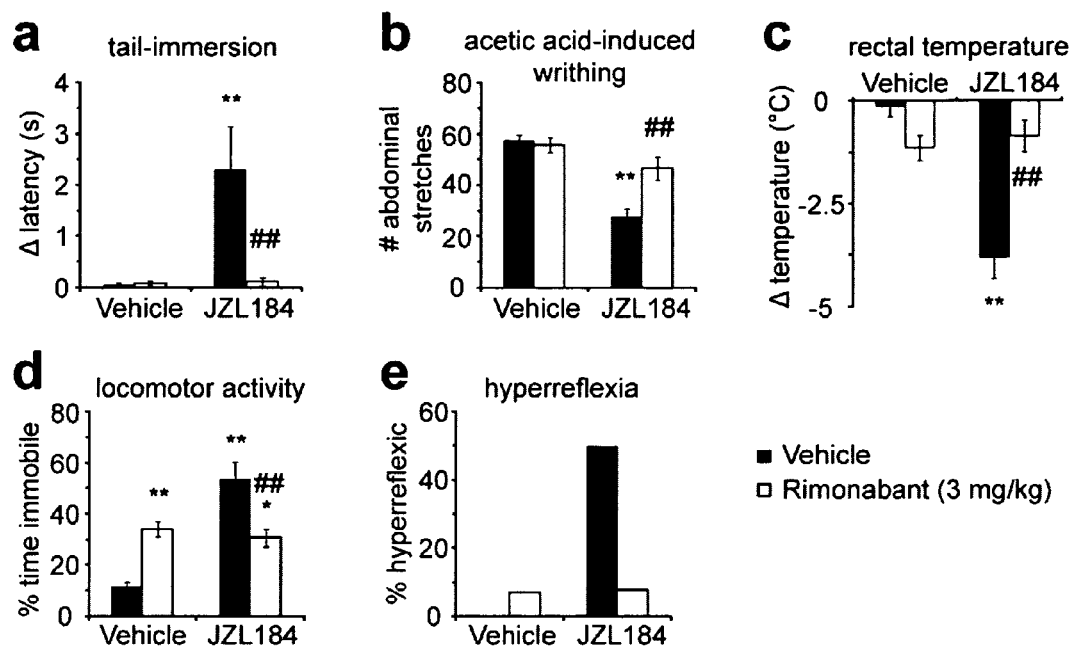
FIGS. 5A-5E show behavioral effects of JZL184. A and B: JZL184 (16 mg/kg) produced hypoalgesic effects in the tail immersion assay of thermal pain sensation (A) and acetic acid abdominal stretching assay of noxious chemical pain sensation (B). These effects were blocked by pre-treatment with the CB1 antagonist rimonabant (3 mg/kg); C-E: JZL184 produced significant hypothermia (C), hypomotility (D), and hyperreflexia (E) that were also significantly attenuated by rimonabant. The baseline tail immersion latency and rectal temperature was 0.82±0.02 s and 37.4±0.1° C., respectively. *, $p<0.05$; **, $p<0.01$ for vehicle-vehicle versus vehicle-JZL184-treated mice. #, $p<0.05$; ##, $p<0.01$ for vehicle-JZL184 versus rimonabant- JZL184-treated versus vehicle-treated. Data are presented as means±SEM. n=10-14 mice/group.

The dramatic and sustained elevations in brain 2-AG levels caused by JZL184 suggested that this inhibitor might induce endocannabinoid-mediated behavioral effects. Direct CB1 agonists are known to promote multiple behavioral effects in rodents, including analgesia, hypomotility, hypothermia, and catalepsy (collectively referred to as the tetrad test for cannabinoid activity). Interestingly, FAAH inhibitors are largely inactive in the tetrad test, causing analgesia, but not other cannabinoid behavioral phenotypes (Lichtman et al., J. Pharmacol. Exp. Ther. 311: 441-8, 2004). JZL184 (16 mg/kg, 2 hr) was also found to exhibit significant analgesic activity in multiple pain assays, including the tail-immersion test of acute thermal pain sensation (FIG. 5A) and the acetic acid writhing test of visceral pain (FIG. 5B). In both cases, the effects of JZL184 were blocked by pre-treatment with the CB1 antagonist rimonabant (3 mg/kg) (FIGS. 5A and B). In marked contrast to FAAH inhibitors, JZL184 also promoted significant hypothermia (FIG. 5C) and hypomotility (FIG. 5D). While JZL184 treatment did not induce catalepsy, 7 of 14 treated mice exhibited hyperreflexia, or "popcorn" behavior (Patel et al., J. Pharmacol. Exp. Ther. 297:629-37, 2001), when assessed in the bar test (FIG. 5E). The hypothermic and hyperreflexia effects were completely blocked by rimonabant, indicating that they are mediated by CB1 receptors. We could not unequivocally determine the contribution of CB1 receptors to the hypomotile effect of JZL184 because rimonabant was found, on its own, to induce significant reductions in movement (FIG. 5D). However, a partial blockade of JZL184-induced immobility was observed with rimonabant (FIG. 5D), suggesting a contribution of CB1 receptors to this phenotype.

Collectively, these data indicate that JZL184 induces a broad array of cannabinoid behavioral effects in rodents that qualitatively mimic the pharmacological profile of direct CB1 agonists. In addition, some of these phenotypes (e.g., hypothermia and hyperreflexia) could be pharmacologically uncoupled from more beneficial effects (e.g., analgesia) by titrating the magnitude of MAGL inhibition in vivo. Indeed, we observed significant increases in 2-AG levels across the entire dose-range of JZL184 tested in this study (4-40 mg/kg), even though the lower doses resulted in less blockade of MAGL activity. These data thus indicate that even partial inhibition of MAGL may be sufficient to augment 2-AG-mediated endocannabinoid signaling in vivo.

Example 6

Synthesis of MAGL Inhibitors

General synthetic methods. All reagents were purchased from commercial vendors and used without further purification, except where noted. Dry solvents were obtained by passing commercially available pre-dried, oxygen-free formulations through activated alumina columns. All reactions were carried out under a nitrogen atmosphere using oven-dried glassware unless otherwise noted. Flash chromatography was performed using 230-400 mesh silica gel. NMR spectra were recorded in $CDCl_3$ on a Varian Inova-400 or a Bruker DMX-600 spectrometer and were referenced to trimethylsilane (TMS) or the residual solvent peak. Chemical shifts are reported in ppm relative to TMS and J values are reported in Hz. High resolution mass spectrometry (HRMS) experiments were performed at The Scripps Research Institute Mass Spectrometry Core on an Agilent mass spectrometer using electrospray ionization-time of flight (ESI-TOF).

Synthesis of JZL184. To a stirring solution of 4-bromo-1,2-methylenedioxybenzene (2.01 g, 10 mmol) in anhydrous THF (30 ml) was added n-BuLi (3.8 ml, 2.6 M in toluene, 9.9 mmol) dropwise at −78° C. After stirring 1.5 hrs at-the same temperature, a solution of ethyl N-Cbz-isonipecotate (1.02 g, 3.5 mmol) in anhydrous THF (10 ml) was added dropwise and an additional portion of THF (3 ml) was used to quantitate the transfer. After the reagent addition was complete, the cooling bath was removed and the suspension gradually turned into a clear solution. After 3 hrs, the reaction was quenched with water and diluted with EtOAc. The layers were separated and the organic layer was washed twice with water, once with brine, dried over $Na_2SO_4$, and concentrated in vacuo. Purification of the crude oil via flash chromatography (Hex:EtOAc=6:1 then 4:1) gave the intermediate alcohol as a white solid (0.81 g, 47% yield): $^1$H NMR ($CDCl_3$, 400 MHz) δ 1.29 (qd, J=4, 12 Hz, 2H), 1.51 (bs, 2H), 2.38 (tt, J=2.8, 12 Hz, 1H), 2.58 (s, 1H), 2.75 (t, J=12 Hz, 2H), 4.19 (bs, 2H), 5.03 (d, J=5 Hz, 2H), 5.85 (s, 4H), 6.70 (d, J=8 Hz, 2H), 6.88-6.92 (m, 4H), 7.24-7.33 (m, 5H); $^{13}$C NMR ($CDCl_3$, 100 MHz) δ 26.6, 44.4, 44.6, 67.1, 79.4, 101.1, 106.9, 107.9, 118.9, 127.9, 128.0, 128.5, 136.9, 140.1, 146.2, 147.7, 155.2; HRMS calculated for $C_{28}H_{27}NNaO_7$ $[M+Na]^+$ 512.1680, found 512.1670. A portion of this intermediate (0.72 g, 1.5 mmol) was dissolved in $CH_2Cl_2$/EtOH (1:1 v/v, 40 ml) and Pd/C (10%, 0.20 g) was added in one portion. The reaction was stirred under $H_2$ (1 atm) overnight. After complete consumption of the starting material (12-24 hrs), the reaction was filtered and concentrated in vacuo. The resulting crude solid was dissolved in $CH_2Cl_2$ (30 mL) and to it was sequentially added $Et_3N$ (2 ml, 15 mmol) and 4-nitrophenyl chloroformate (460 mg, 2.3 mmol). The reaction was stirred overnight. The next morning, the reaction was quenched with water and diluted with EtOAc. The layers were separated and the organic layer was washed thrice with 2N NaOH, once with brine, dried over $Na_2SO_4$, and concentrated in vacuo. Purification of the crude oil via flash chromatography (Hex:EtOAc=6:1 then 4:1) gave JZL184 as a pale yellow oil that turned into a yellow solid upon standing under vacuum (550 mg, 71% yield for two steps).

Synthesis of JZL175. To a stirring solution of ethyl N-Cbz-isonipecotate (0.84 g, 2.9 mmol) in anhydrous THF (10 ml) was added 4-anisylemagnesium bromide (15 ml, 0.5 M in THF) dropwise at room temperature. After the reagent addition was complete, the reaction was heated to reflux overnight. The next morning, the reaction was quenched with water and diluted with EtOAc. The layers were separated and the organic layer was washed twice with water, once with brine, dried over $Na_2SO_4$, and concentrated in vacuo. Purification of the crude oil via flash chromatography (Hex:EtOAc=6:1 then 2:1) gave the intermediate alcohol as a pale yellow solid (0.90 g, 69% yield): $^1$H NMR ($CDCl_3$, 400 MHz) δ 1.24-1.33 (m, 2H), 1.54 (bs, 2H), 2.14-2.18 (m, 1H), 2.46 (t, J=12 Hz, 1H), 2.77 (t, J=11 Hz, 2H), 3.75 (s, 6H), 4.21 (bs, 2H), 5.06 (s, 2H), 6.81 (d, J=9 Hz, 4H), 7.27-7.34 (m, 9H). This material was used without further characterization. A portion of this intermediate (55 mg, 0.18 mmol) was treated in a two step procedure with Pd/C and 4-nitrophenyl chloroformate in a manner analogous to the synthesis of JZL184. Purification of the crude oil via flash chromatography (Hex:EtOAc=6:1 then 2:1) gave JZL175 as a pale yellow oil that turned into a yellow solid upon standing under vacuum (55 mg, 62% yield for two steps): $^1$H NMR ($CDCl_3$, 400 MHz) δ 1.40 (m, 2H), 1.65 (t, J=11 Hz, 2H), 2.26 (bs, 1H), 2.55 (t, J=12 Hz, 1H), 2.87 (t, J=12 Hz, 1H), 3.00 (t, J=13 Hz, 1H), 3.76 (s, 6H), 4.27 (t, J=13 Hz, 2H), 6.84 (d, J=9 Hz, 4H), 7.24 (d, J=9 Hz, 2H), 7.34 (d, J=9 Hz, 4H), 8.19 (d, J=9 Hz, 2H); $^{13}$C NMR ($CDCl_3$, 100 MHz) δ 26.6, 26.9, 44.4, 45.2, 55.4, 79.2, 113.6, 113.7, 122.4, 125.1, 127.3, 137.8, 137.9, 144.8, 152.2, 156.5, 158.4; HRMS calculated for $C_{27}H_{27}N_2O_6$ $[M−H_2O+H]^+$ 475.1864, found 475.1864.

Synthesis of WWL152. To a stirring solution of N-Boc piperazine (100 mg, 0.54 mmol) in $CH_2Cl_2$ (5 ml) was sequentially added 4-nitrophenyl chloroformate (109 mg, 0.54 mmol) and $Et_3N$ (75 µl, 0.54 mmol) at room temperature. After 3 hrs, the reaction was concentrated in vacuo. Purification of the crude mixture via flash chromatography (Hex:EtOAc=3:1) gave the Boc-protected intermediate as a white solid (100 mg, 52% yield): $^1$H NMR ($CDCl_3$, 400 MHz) δ 8.24 (d, J=9 Hz, 2H), 7.31 (d, J=9 Hz, 2H), 3.67 (bs, 2H), 3.54 (bs, 6H), 1.50 (s, 9H). To the intermediate (100 mg, 0.28 mmol) was added 1:1 v/v TFA:$CH_2Cl_2$ (2 ml) at room temperature. After 2 hrs, the reaction was concentrated in vacuo. The crude was used without further purification. To a stirring solution of 4-methoxy benzophenone (100 mg, 0.5 mmol) in EtOH (5 ml) was added $NaBH_4$ (38 mg, 1 mmol) at room temperature. The next morning, the reaction was poured onto water (10 ml), stirred for 1 hr, and then the product was filtered off and dried. To the crude alcohol in $CH_2Cl_2$ (5 ml) was added oxalyl chloride (40 µL, 0.46 mmol) dropwise at room temperature. After 2 hrs, the reaction was concentrated in vacuo. The crude was redissolved in $CH_3CN$ (2 ml) and to it was sequentially added 4-nitrophenyl piperazine-1-carboxylate (58 mg, 0.23 mmol) and $Et_3N$ (32 µl, 0.23 mmol). After the reagent addition was complete, the reaction was heated to reflux overnight. The next morning, the reaction was concentrated in vacuo. Purification of the crude mixture via flash chromatography (Hex:EtOAc=1:1) gave WWL152 as a white solid (201 mg, 84% yield over 3 steps): $^1$H NMR ($CDCl_3$, 600 MHz) δ 8.24 (d, J=9 Hz, 2H), 7.32 (d, J=8 Hz, 4H), 7.27 (d, J=9 Hz, 2H), 6.84 (d, J=8 Hz, 4H), 4.22 (s, 1H), 3.76 (s, 6H), 3.66 (s, 2H), 3.57 (s, 2H), 2.45 (s, 4H); HRMS calculated for $C_{26}H_{27}N_3O_6$ [M+H]$^+$ 478.1973, found 478.1977.

Synthesis of WWL162. To 1-(bis(4-fluorophenyl)methyl) piperazine (29 mg, 0.1 mmol) in $CH_2Cl_2$ (2 mL) was sequentially added 4-nitrophenyl chloroformate (20 mg, 0.1 mmol) and $Et_3N$ 14 µl, 0.1 mmol) at room temperature. After 3 hrs, the reaction was concentrated in vacuo. Purification of the crude mixture via flash chromatography (Hex:EtOAc=3:1) gave WWL162 as a white solid (42 mg, 92% yield): $^1$H NMR (CDCl$_3$, 600 MHz) δ 8.24 (d, J=9 Hz, 2H), 7.36 (m, 4H), 7.28 (d, J=9 Hz, 2H), 7.00 (m, 4H), 4.29 (s, 1H), 3.68 (s, 2H), 3.59 (s, 2H), 2.44 (s, 4H); HRMS calcd for $C_{24}H_{21}F_2N_3O_4$ [M+H]$^+$ 454.1573, found 454.1578.

Example 7

Other Methods and Materials

Materials. 2-AG, pentadecanoic acid (PDA), AEA, and URB597 were purchased from Cayman Chemicals (Ann Arbor, Mich.). Tetrahydrolipstatin (THL) was purchased from Sigma (St. Louis, Mo.). FP-rhodamine and FP-biotin were synthesized as described previously (Liu et al., Proc. Natl. Acad. Sci. U.S.A. 96:14694-9, 1999; and Patricelli et al., Proteomics 1:1067-71, 2001). Rimbonabant was obtained from NIDA (Rockville, Md.) and dissolved in a vehicle of 18:1:1 v/v/v saline, ethanol, and alkamuls-620 (Rhone-Poulenc, Princeton, N.J.). $^{13}$C-oleamide ($^{13}C_{18}H_{35}NO$) was synthesized from $^{13}$C-oleic acid (Spectra Stable Isotopes, Columbia, Md.) according to the methods described in Cravatt et al., Science 268:1506-9, 1995.

Preparation of mouse tissue proteomes. Mouse brains were Dounce-homogenized in PBS, pH 7.5, followed by a low-speed spin (1,400×g, 5 min) to remove debris. The supernatant was then subjected to centrifugation (64,000×g, 45 min) to provide the cytosolic fraction in the supernatant and the membrane fraction as a pellet. The pellet was washed and resuspended in PBS buffer by sonication. Total protein concentration in each fraction was determined using a protein assay kit (Bio-Rad). Samples were stored at −80° C. until use.

Recombinant expression in COS7 or HEK293 cells. Briefly, full-length cDNAs encoding mouse serine hydrolases were purchased from OpenBioSystems (Huntsville, Ala.). cDNAs were either transfected directly (if available in a eukaryotic expression vector) or subcloned into pcDNA3 (Invitrogen). COS7 cells were grown to ~70% confluence in 10 cm dishes in complete medium (DMEM with L-glutamine, nonessential amino acids, sodium pyruvate, and FCS) at 37° C. and 5% $CO_2$. The cells were transiently transfected by using the appropriate cDNA or empty vector control ("mock") and the FUGENE 6 (Roche Applied Science) transfection reagents following the manufacturers' protocols. After 48 hrs, the cells were washed twice with phosphate-buffered saline (PBS), collected by scraping, resuspended in 0.25 ml PBS, and lysed by sonication. The lysates were used in assays as whole-cell homogenates.

Enzyme activity assays. Briefly, 2-AG (100 µM) was incubated with mouse brain membrane (20 µg) or recombinant MAGL in COS7 cells (0.1 µg) in PBS (200 µl) at room temperature for 10 min. The reactions were quenched by the addition of 500 µL 2:1 v/v CHCl$_3$:MeOH, doped with 0.5 nmol PDA, vortexed, then centrifuged (1,400×g, 3 min) to separate the phases. 30 ul of the resultant organic phase was injected onto an Agilent 1100 series LC-MSD SL instrument. LC separation was achieved with a Gemini reverse-phase C18 column (5 µm, 4.6 mm×50 mm, Phenomonex) together with a pre-column (C18, 3.5 µm, 2 mm×20 mm). Mobile phase A was composed of 95:5 v/v H$_2$O:MeOH, and mobile phase B was composed of 60:35:5 v/v/v i-PrOH:MeOH:H$_2$O. 0.1% ammonium hydroxide was included to assist in ion formation in negative ionization mode. The flow rate was 0.5 ml/min and the gradient consisted of 1.5 min 0% B, a linear increase to 100% B over 5 min, followed by an isocratic gradient of 100% B for 3.5 min before equilibrating for 2 min at 0% B. MS analysis was performed with an electrospray ionization (ESI) source. The capillary voltage was set to 3.0 kV and the fragmentor voltage was set to 100 V. The drying gas temperature was 350° C., the drying gas flow rate was 10 l/min, and the nebulizer pressure was 35 psi. Hydrolysis products were quantified by measuring the area under the peak in comparison to the PDA standard. $^{13}$C-oleamide or AEA hydrolysis activity was determined using mouse brain membrane (50 µg) or recombinant FAAH in COST cells (5 µg), respectively, in PBS (100 µl). The reactions were performed in a manner similar to that described for 2-AG hydrolysis, except the incubation time was 20 min at 37° C. and 300 µl 2:1 v/v CHCl$_3$:MeOH was used to quench the reaction. DAGLβ hydrolysis activity was determined using recombinant DAGLβ in HEK293 cells (50 µg) in PBS (100 µl). The reactions were performed in a manner similar to that described for oleamide hydrolysis, except the incubation time was 30 min at 37° C.

JZL184 displacement of [$^3$H]-rimonabant Binding. Membranes were prepared as described above. Membrane proteins (8 µg) were incubated with 0.2-3 nM [$^3$H]-rimonabant in 50 mM Tris-HCl, 3 mM MgCl$_2$, 0.2 mM EGTA, 100 mM NaCl, 1.25 g/l BSA, pH 7.4 in the presence or absence of 5 µM unlabeled rimonabant (to determine non-specific binding) for 90 min at 30° C. A second set of samples was prepared using the same protocol but with varying concentrations of JZL184 (0.001-10 µM). The reaction was terminated by vacuum filtration though Whatman GF/B glass fiber filter that was pre-soaked in Tris buffer containing 5 g/l BSA (Tris-BSA), followed by three washes with 4° C. Tris-BSA. Bound radioactivity was determined by liquid scintillation spectrophotometry at 45% efficiency after extraction in ScinitSafe Econo 1 scintillation fluid.

Measurement of brain lipids. One half brain was weighed and subsequently Dounce homogenized in 2:1:1 v/v/v CHCl$_3$:MeOH:Tris pH 8.0 (8 ml) containing standards for N-acylethanolamine (NAE), monoacylglycerol (MAG), or free fatty acid (FFA) measurements (200 pmol d$_4$-OEA, 20 pmol d$_4$-AEA, 400 pmol C15:0-MAG, and 4 nmol PDA). The mixture was vortexed and then centrifuged (1,400×g, 10 min). The organic layer was removed, CHCl$_3$ was added until the final volume was again 8 ml, and the extraction was repeated. The combined organic extracts were dried under a stream of N$_2$ and resolubilized in 2:1 v/v CHCl$_3$:MeOH (120 µl). 30 uL and 15 uL of resolubilized lipid were injected for positive mode (MAG and NAE) and negative mode (free fatty acid) measurements, respectively. Lipid measurements were performed by LC-MS using the same instrument and solvents as described above. Solvent modifiers such as 0.1% formic acid or 0.1% ammonium hydroxide were included to assist in ion formation in positive and negative ionization mode, respectively. For positive mode measurements, the flow rate for each run started at 0.1 ml/min for 5 min. The gradient started at 0% B and increased linearly to 100% B over 40 min with a flow rate of 0.4 ml/min, followed by an isocratic gradient of 100% B for 7 min before equilibrating for 8 min at 0% B with a flow rate of 0.5 ml/min. For negative mode measurements, the flow rate for each run started at 0.1 ml/min for 3 min. The gradient started at 0% B and increased linearly to 100% B over 17 min with a flow rate of 0.4 ml/min, followed by an isocratic gradient of 100% B for 7 min before equilibrating for 3 min at 0% B with a flow rate of 0.5 ml/min. MAGs, NAEs, and FFAs were quantified by measuring the area under the peak in comparison to the C15:0 or deuterated standards. Targeted LC-MS measurements were performed using selected ion monitoring (SIM).

ABPP-MudPIT analysis of SH targeted by JZL184 in vivo. A portion of the brain membrane proteomes (1 ml, 1 mg/ml in PBS) from the mice treated with JZL184 or vehicle as described above was labeled with 5 µM FP-biotin for 1 h at room temperature and prepared for ABPP-MudPIT analysis as described in the art, except that the Lys-C digestion step was omitted (Greenbaum et al., Mol. Cell. Proteomics 1:60-68, 2002; and Alexander et al., J. Am. Chem. Soc. 128:9699-704, 2006). MudPIT analysis of eluted peptides was carried out as previously described on a coupled Agilent 1100 LC-ThermoFinnigan LTQ-MS instrument. All data sets were searched against the mouse IPI database using the SEQUEST search algorithm and the results were filtered and grouped with DTASELECT. Peptides with cross-correlation scores greater than 1.8 (+1), 2.5 (+2), 3.5 (+3) and delta CN scores greater than 0.08 were included in the spectral counting analysis. Only proteins for which 5 or more spectral counts were identified on average in the control samples were considered for comparative analysis. Specifically, probe-labeled proteins were further identified by their presence in FP-treated samples with a spectral number at least 5-fold or greater than that observed in "no probe" control runs (experiments performed as described above, but without inclusion of biotinylated FP). Spectral counts are reported as the average of three samples with the standard error of the mean (SEM).

Behavioral Studies. The pharmacological effects of JZL184 versus rimonabant were evaluated using the following indices: locomotor activity, nociception in the hotplate and tail immersion tests, catalepsy in the bar test, and for hypothermia. A total of four groups of mice were used, with a sample size of 14 mice/group. Before injections, the mice were evaluated for baseline responses in the tail immersion test, as well for rectal temperatures. Subjects were given an intraperitoneal injection of rimonabant or vehicle, followed by an intraperitoneal injection of JZL184 or its respective vehicle 10 min later. Locomotor activity was assessed 120 min after administration of JZL184 or vehicle, tail withdrawal latencies were evaluated 135 min after the second injection, and Catalepsy and rectal temperature were assessed at 145 min post-injection. For determining hypomotility each mouse was placed in a clear Plexiglas box (42.7×21.0×20.4 cm) for a 10 min assessment period and Anymaze (Stoelting, Wood Dale, Ill.) software was used to determine the percentage of time spent immobile. Subjects were assessed for nociception in the tail immersion assay. Each mouse was placed head first into a small bag fabricated from absorbent under pads (VWR Scientific Products; 4 cm diameter, 11 cm length) with the tail out of the bag. The experimenter gently held the mouse and immersed approximately 1 cm of the tip of the tail into a water bath maintained at 56.0° C. The latency for the animal to withdraw its tail from the water within a 10 s cutoff time was scored. Catalepsy was evaluated using the bar test, in which the front paws of each subject were placed on a rod (0.75 cm diameter) that was elevated 4.5 cm above the surface. Mice that remained motionless with their paws on the bar for 10 s (with the exception of respiratory movements) were scored as cataleptic. Although no mice were found to be cataleptic in the present study, half of the mice treated with JZL184 alone displayed a hyperreflexia when the front paws were placed on rod, which was exemplified by jumping or "popcorn" behavior. Rectal temperature was determined by inserting a thermocouple probe 2.0 cm into the rectum and temperature was obtained from a telethermometer.

A second group of naïve subjects (n=10-11 mice/group) were evaluated in the acetic acid stretching assay. Subjects were given a subcutaneous injection of rimonabant or its vehicle, followed by a subcutaneous injection of JZL184 or vehicle 10 min later. Acetic acid (0.6%) was injected intraperitoneally in a volume of 10 µl/g body weight 120 min after the second injection. The number of stretches (constriction of abdomen, turning of trunk (twist) and extension of the body and hind limbs) per mouse was counted during a 20-min period after the administration of acetic acid.

Competitive activity-based protein profiling (ABPP) experiments. In vitro inhibitor selectivity was examined using a competitive ABPP method as described in the art (e.g., Li et al., J. Am. Chem. Soc. 129:9594-5, 2007; and Leung et al., Nat. Biotech. 21:687-91, 2003). Briefly, mouse brain membrane proteomes, prepared as described herein, were diluted to 1 mg/ml in PBS and pre-incubated with varying concentrations of inhibitors (1 nM to 10 µM) for 30 min at 37° C. prior to the addition of a FP-rhodamine at a final concentration of 2 µM in a 50 µl of total reaction volume. After 30 min at room temperature, the reactions were quenched with 4×SDS-PAGE loading buffer, boiled for 5 min at 90° C., subjected to SDS-PAGE, and visualized in-gel using a flatbed fluorescence scanner.

In vitro studies with JZL184. Standard assays were performed by pre-incubating protein samples with JZL184 for 30 min at 37° C. prior to the addition of substrate or ABPP probe. Concentration-dependence inhibition curves were obtained from substrate assays and were fit using Prism software (GraphPad) to obtain $EC_{50}$ values with 95% confidence intervals. For measurement of $k_{obs}/[I]$ values, brain membrane proteomes (1 mg/ml, 300 µl total) were incubated with JZL184 (0.01-15 µM, 10-40 min, 37° C). Every 10 min, 50 ul of the reaction was removed and treated with FP-rhodamine (2 µM) for 2 min, quenched with 4×SDS-PAGE loading buffer, and boiled for 5 min at 90° C. The combined reactions were subjected to SDS-PAGE and visualized in-gel using a flatbed fluorescence scanner. The percentage activity remaining was determined by measuring the integrated optical density corresponding to the MAGL or FAAH bands and the results were fit to an exponential curve to determine the pseudo-first order rate constants.

In vivo studies with JZL184. JZL184 (neat) was dissolved by vortexing, sonicating, and gentle heating directly into 4:1 v/v PEG300:Tween80 (10, 4, 2, or 1 mg/ml). Male C57B1/6J mice (6-8 weeks old, 20-26 g) were intraperitoneally (i.p.) administered JZL184 or a 4:1 v/v PEG300:Tween80 vehicle without JZL184 at a volume of 4 ul/g weight (40, 16, 8, or 4 mg/kg by the dilutions above). After the indicated amount of time, mice were anesthetized with isofluorane and sacrificed by decapitation. Brains were removed, hemisected along the midsagittal plane, and each half was then flash frozen in liquid $N_2$. One half of the brain was prepared as described above for protein analysis and the other half was used for metabolite analysis. The selective inhibition of FAAH by URB597 was achieved in a similar manner as described above, except URB597 was dissolved by sonication into 18:1:1 v/v/v saline:emulphor:ethanol (1 mg/ml) and administered i.p. at a volume of 10 µ/g weight (10 mg/kg final dose).

Example 8

Identification of Elevated MAG Activity in Cancer Pathogenesis

To identify enzyme activities that contribute to cancer pathogenesis, we conducted a functional proteomic analysis of a panel of aggressive and non-aggressive human cancer cell lines from multiple tumors of origin, including melanoma [aggressive (C8161, MUM2B), non-aggressive (MUM2C)], ovarian [aggressive (SKOV3), non-aggressive (OVCAR3)], and breast [aggressive (231MFP), non-aggressive (MCF7)] cancer. Aggressive cancer lines were confirmed to display much greater in vitro migration and in vivo tumor-growth rates compared to their non-aggressive counterparts. Proteomes from these cancer lines were screened by activity-based protein profiling (ABPP) using serine hydrolase-directed fluorophosphonate (FP) activity-based probes. The goal of this study was to identify hydrolytic enzyme activities that were consistently altered in aggressive versus non-aggressive cancer lines, working under the hypothesis that these conserved enzymatic changes would have a high probability of contributing to the pathogenic state of cancer cells.

Figure 13:
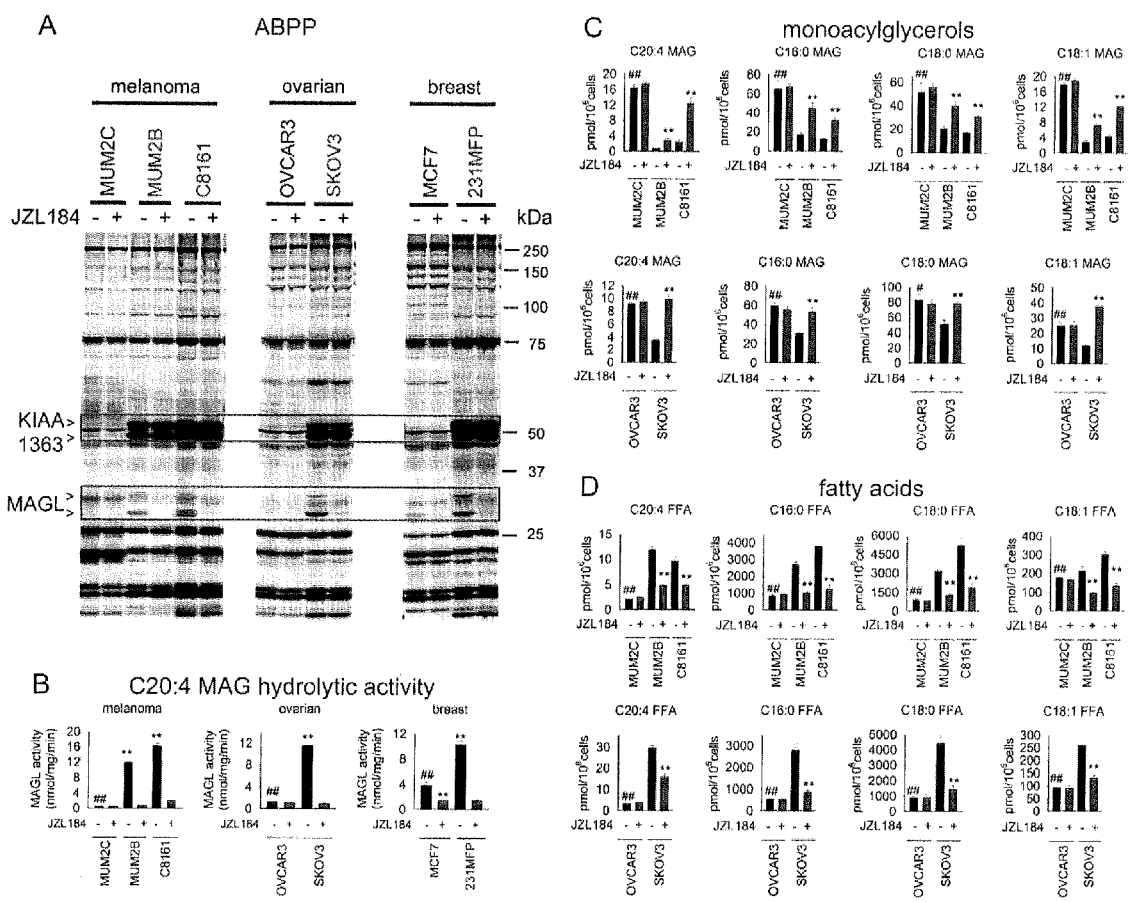
FIGS. 13A-13D show that MAGL is elevated in aggressive cancer cells, where the enzyme regulates monoacylglycerol (MAG) and free fatty acid (FFA) levels. (A) ABPP of serine hydrolase activities in non-aggressive (blue) and aggressive (red) human cancer cell lines. Serine hydrolase activities were labeled in whole cell proteomes with the activity-based probe FP-rhodamine and detected by SDS-PAGE and in-gel fluorescence scanning (fluorescent gel shown in grayscale). Highlighted in red boxes are two enzymes, MAGL and KIAA1363 that are consistently elevated in aggressive versus nonaggressive cancer cells. Proteomes were also prepared from cancer cells pretreated with DMSO or the selective MAGL inhibitor JZL184 (1 μM, 4 h) to confirm that the 33 and 35 kDa FP-rhodamine-labeled bands represented MAGL. (B) C20:4 MAG hydrolytic activity of cancer cells in the presence (red bars) or absence (black bars) of JZL184 (1 μM, 4 hr). (C, D) Inhibition of MAGL (JZL184 1 μM, 4 h) raises MAG (C) and lowers FFA (D) levels in aggressive, but not nonaggressive cells. Note that aggressive cancer cells possess basally higher levels of FFAs (and lower levels of MAGs) compared to non-aggressive cancer cells, reflecting their respective MAGL activities. * $p<0.05$, ** $p<0.01$ for JZL184-treated versus DMSO-treated control groups. # $p<0.05$, ## $p<0.01$ for aggressive versus non-aggressive cancer cells. Data are presented as means±SEM; n=4-5/group.
Figure 20:
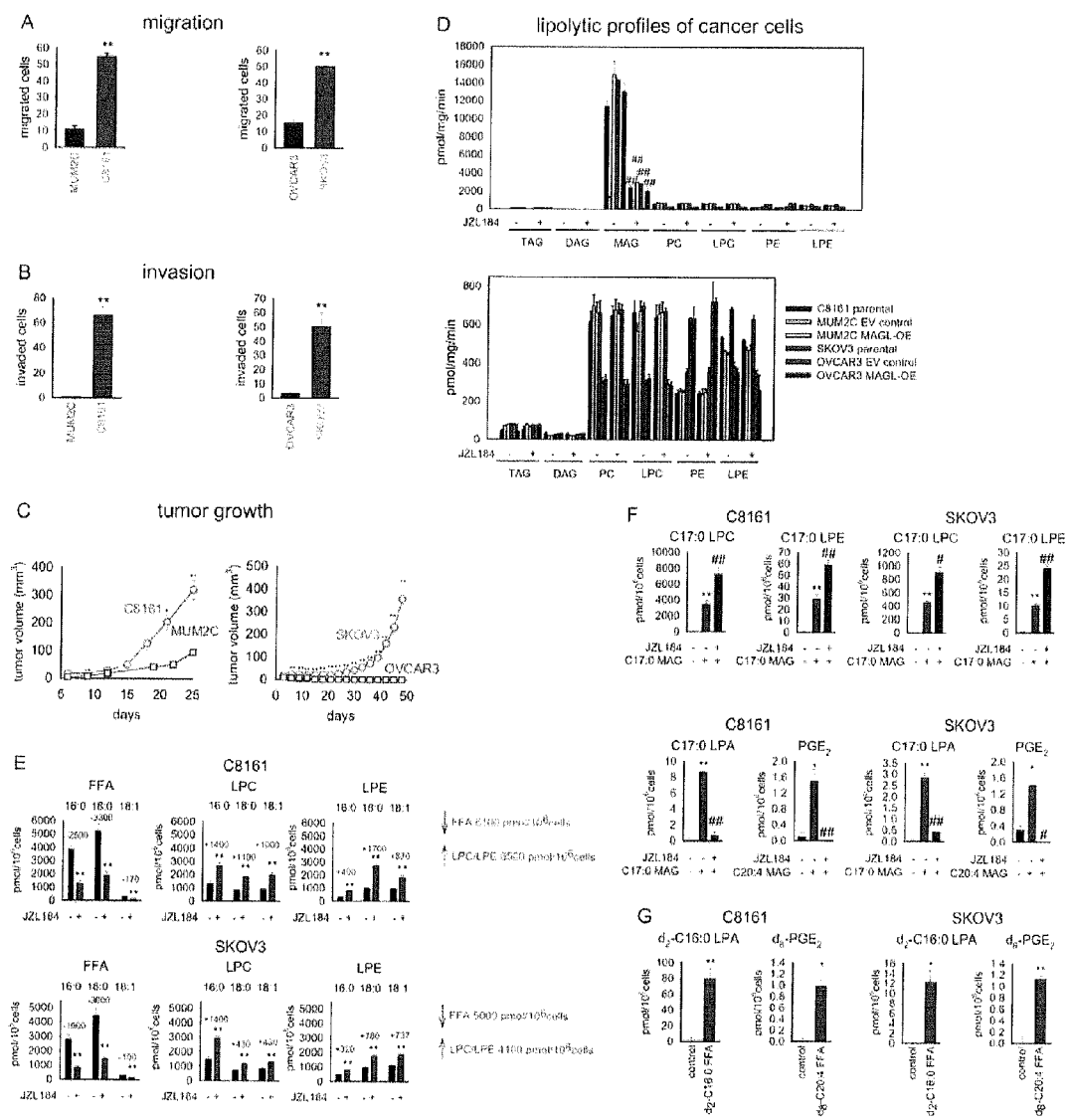
FIGS. 20A-20G show MAGL, KIAA1363 and lipolytic profiles across the panel of aggressive versus nonaggressive melanoma and ovarian cancer cell lines. There is a mass balance discrepancy between elevated MAGs and reduced FFAs caused by treatment of cancer cells with the MAGL inhibitor JZL184. (A-C) Aggressive melanoma (C8161) and ovarian (SKOV3) cells show greater migration (A) and invasion (B) and faster tumor growth rates (C) compared to their nonaggressive counterparts (MUM2C and OVCAR3 cells, respectively). (D) Lipolytic profiles of cancer cell lines shows robust hydrolytic activity of MAGs in aggressive cancer cells compared to other lipolytic activities. In vitro free fatty acid (FFA) release from various lipid substrates was assayed. Cells were treated with DMSO or JZL184 in situ for 4 hr in serum-free media. Cell lysates (20 μg) were incubated with 100 μM lipid substrate for 1 hr at room temperature. Upper and lower panels show the same data with different y-axis scales (with and without MAG hydrolytic activity) for ease of comparison and visualization. Abbreviation for lipid substrates are as follows: TAG, triacylglycerol; DAG, diacylglycerol; MAG, monoacylglycerol; PC, phosphatidylcholine; LPC, lysophosphatidylcholine; PE phosphatidyl ethanolamine; LPE, lysophosphatidyl ethanolamine. $*p<0.05$, $**p<0.01$ for aggressive versus non-aggressive cancer line groups and $\#\#p<0.01$ for DMSO versus JZL184. Data are presented as means±SEM; n=3-15/group. Elevations in lysophospholipids account for the mass balance discrepancy between elevated MAGs and reduced FFAs caused by treatment of cancer cells with the MAGL inhibitor JZL184. (E) JZL184 (1 μM, 4 hr) causes a 5500-6100 pmol/$10^6$ decrease in FFA levels in C8161 and SKOV3 cells. This reduction in FFA levels is similar in magnitude to the net increase in lysophosphatidylcholine (LPC) and lysophosphatidylethanolamine (LPE) levels observed in JZL184-treated cancer cells (4100-6500 pmol/$10^6$ cells). (F) C17:0 MAG (20 μM, 1 hr) is converted to C17:0 LPC and C17:0 LPE by cancer cells, and this conversion is further enhanced by preincubation of cancer cells with JZL184 (1 μM, 4 hr). C17:0 MAG is also converted to C17:0 LPA, but, in this case, the conversion is blocked by JZL184. These data indicate that C17:0 MAG is directly converted to C17:0 LPC and C17:0 LPE in cancer cells, while conversion of C17:0 MAG to C17:0 LPA requires MAGL-dependent hydrolysis of C17:0 MAG to C17:0 FFA. C20:4 MAG (20 μM, 1 hr) is converted to prostaglandin $E_2$ (PGE2), and this conversion is blocked by JZL184. (G) C16:0 and C20:4 FFAs are converted to LPA and PGE2, respectively, by aggressive cancer cells. C8161 and SKOV3 cells were treated with $d_2$-C16:0 FFA or $d_8$-C20:4 FFA (10 μM, 4 hr) in serum-free media. $d_2$-C16:0 FFA was converted to $d_2$-C16:0 LPA and $d_8$-C20:4 FFA was converted to $d_8$-$PGE_2$. $*p<0.05$, $**p<0.01$ for comparison of control cells versus treated cells, $\#p<0.05$, $\#\#p<0.01$ for comparison of JZL184/MAG treated cells versus MAG-treated cells alone. Data are presented as means±SEM; n=3-4/group.

Among the more than 50 serine hydrolases detected in this analysis, two enzymes, KIAA1363 and MAGL, were found to be consistently elevated in aggressive cancer cells relative to their non-aggressive counterparts, as judged by spectral counting. We confirmed elevations in KIAA1363 and MAGL in aggressive cancer cells by gel-based ABPP, where proteomes are treated with a rhodamine-tagged FP probe and resolved by 1D-SDS-PAGE and in-gel fluorescence scanning (FIG. 13A). In both cases, two forms of each enzyme were detected (FIG. 13A), due to differential glycoslyation for KIAA1363, and possibly alternative splicing for MAGL (Karlsson et al., Gene 272, 11-18, 2001). The heightened activity of MAGL in aggressive cancer cells was confirmed using the substrate C20:4 MAG (FIG. 13B). Since several enzymes have been shown to display MAG hydrolytic activity (Blankman et al., Chem Biol 14, 1347-1356, 2007), we confirmed the contribution that MAGL makes to this process in cancer cells using the potent and selective MAGL inhibitor JZL184. JZL184 (1 µM, 4 hr) dramatically reduced the MAG hydrolytic activity of cancer cells (FIG. 13B) and selectively blocked the FP-rhodamine signals for both the 33 and 35 kDa forms of MAGL (FIG. 13A). In contrast, we found that JZL184 treatment did not alter the hydrolytic activity displayed by cancer cells for several additional classes of lipids, including diacylglycerols, triacylglycerols, lysophospholipids, and phospholipids (FIG. 20). These data demonstrate that aggressive cancer cells display highly elevated MAG activity and most, if not all, of this activity originates from the MAGL enzyme.

Further studies reveal that MAGL regulates free fatty acid (FFA) levels in aggressive cancer cells. Consistent with the known function of MAGL, we observed that blockade of MAGL by JZL184 (1 µM, 4 hr) produced significant elevations in the levels of several monoacylglycerols (MAGs), including 2-AG, in each of the aggressive cancer cell lines (FIG. 13C). Interestingly, however, MAGL inhibition also caused significant reductions in the levels of FFAs in aggressive cancer cells (FIG. 13D). This surprising finding contrasts with the function of MAGL in normal tissues. It was known that this enzyme does not, in general, control the levels of FFAs (Nomura et al., Nat Chem Biol 4, 373-378, 2008). We also noted that, with the exception of C20:4 FFA and MAG, the magnitude of reduction of FFAs greatly exceeded the corresponding elevation in MAGs (~5000-6100 pmol and 41-75 pmol, respectively, for C16:0, C18:0, and C18:1 lipids). It is possible that this apparent discrepancy in mass balance might be accounted for by the conversion of elevated MAGs to alternative metabolites in JZL184-treated cancer cells. Consistent with this premise, we found that lipidomic analyses revealed significant increases in two major classes of lysophospholipids—lysophosphatidyl choline (LPC) and lysophosphatidyl ethanolamine (LPE)—in JZL184-treated cancer cells. The cumulative magnitude of elevation of these lysophospholipids (4100-6500 pmol), matched closely the reduction in FFAs observed in JZL184-treated cells. Notably, we did not detect C20:4 lysophospholipids in cancer cells, providing a likely explanation for why JZL184 caused similar magnitudes of elevation and reduction in C20:4 MAG and FFA, respectively. Metabolic labeling studies using the non-natural C17:0-MAG confirmed that MAGs are converted to LPC and LPE by aggressive cancer cells, and that this metabolic transformation is significantly enhanced by treatment with JZL184. Finally, we found that JZL184 treatment did not affect the levels of MAGs and FFAs in non-aggressive cancer lines (FIG. 13C, 13D), consistent with the negligible expression of MAGL in these cells (FIG. 13A, 13B).

Figure 14:
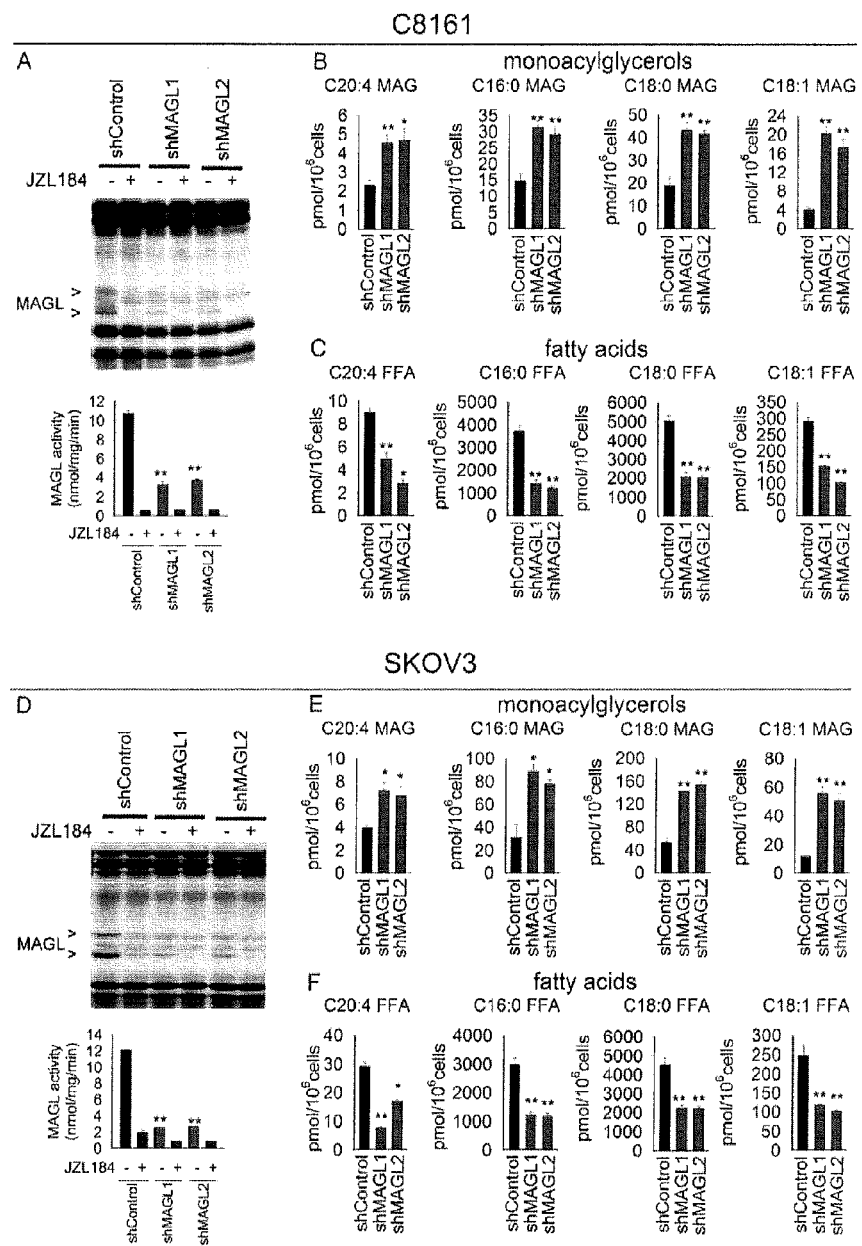
FIGS. 14A-14F show that stable shRNA-mediated knock-down of MAGL lowers FFA levels in aggressive cancer cells. (A, D) MAGL was stably knocked down using two independent short hairpin RNA (shRNA) oligonucleotides (shMAGL1, shMAGL2), resulting in >70% reductions in MAGL activity in C8161 and SKOV3 cells compared to shControl cells expressing an shRNA that targets a distinct serine hydrolase (DPPIV). (B, C, E, F) shMAGL cells show elevations in MAG (B, E) and reductions in FFA (C, F) levels. * p<0.05, ** p<0.01 for shMAGL- versus shControl groups. # p<0.05, ## p<0.01 for aggressive versus non-aggressive cancer cells. The MAGL activity and MAG and FFA levels of shControl cells did not differ significantly from those of parental cancer lines. Data are presented as means±SEM; n=4-5/group.
Figure 15:
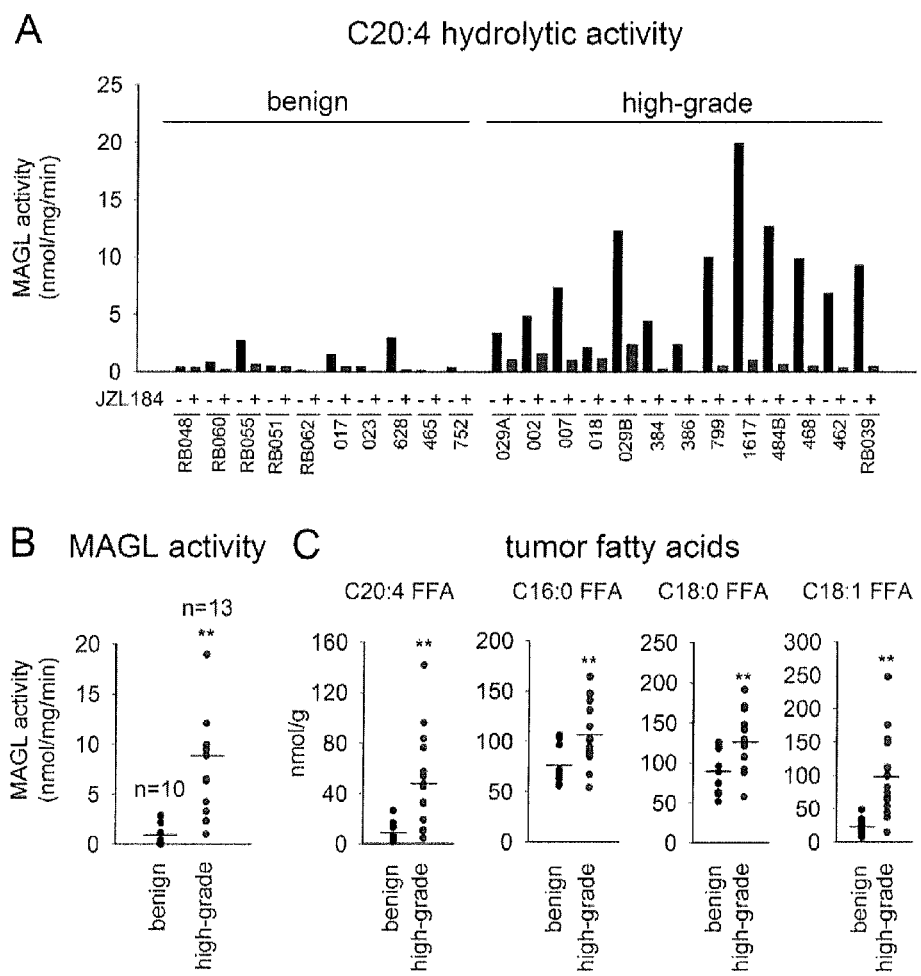
FIGS. 15A-15C show that high-grade primary human ovarian tumors possess elevated MAGL activity and FFAs compared to benign tumors. (A) C20:4 MAG hydrolytic activity measurements for individual tumor specimens. Pre-treatment with JZL184 (1 µM, 30 min) confirmed that the majority of the observed hydrolytic activity is due to MAGL. (B) Summary graph of MAGL activity in benign versus high-grade tumors, where each value is expressed as the JZL184-sensitive portion of total C20:4 MAG hydrolytic activity shown in part (A). (C) Levels of FFAs in benign versus high-grade tumors. ** p<0.01 for high-grade versus benign tumor groups. Data are presented as means ±SEM; n=10-13/group.
Figure 21:
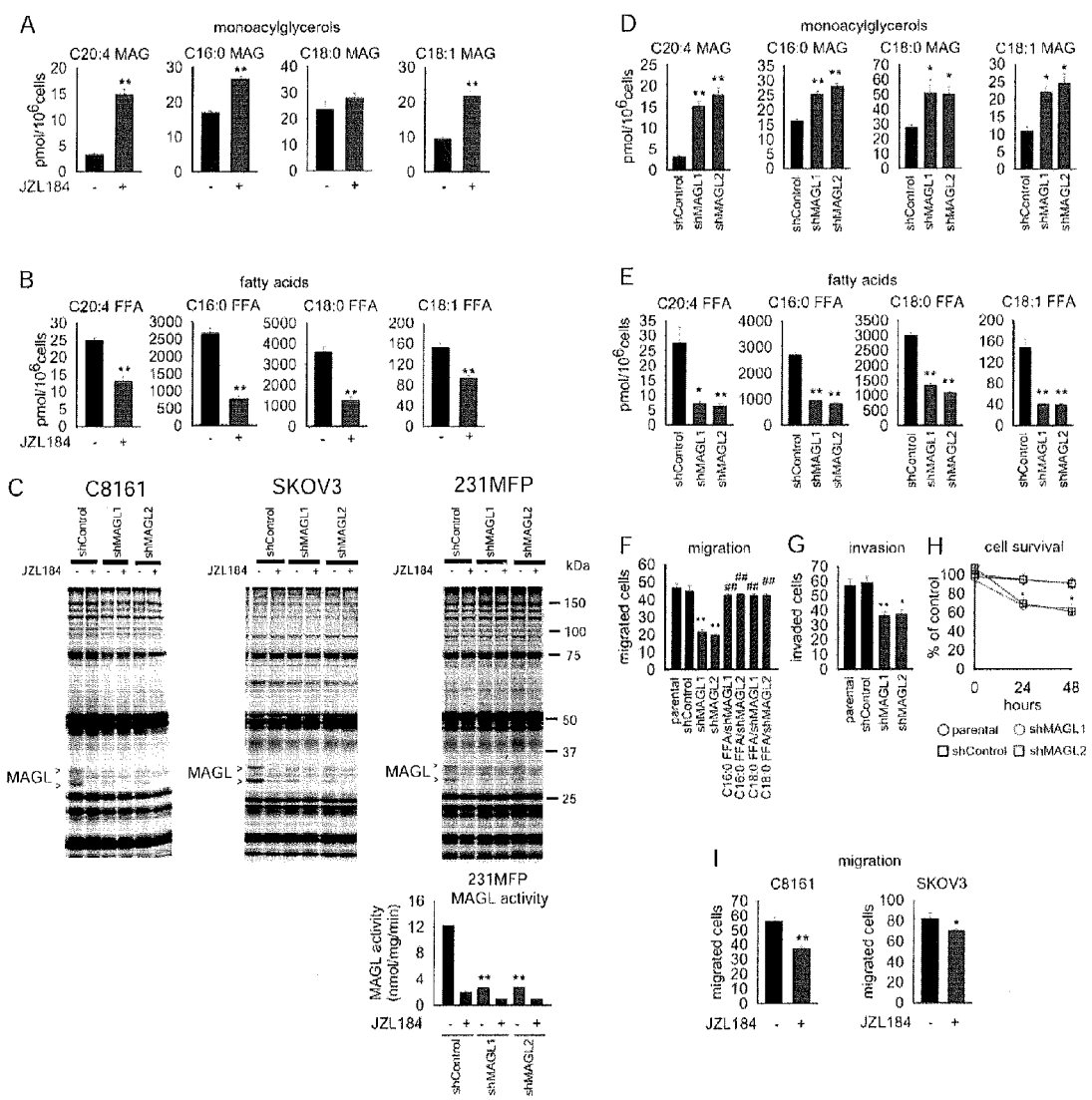
FIGS. 21A-21I show that MAGL regulates MAG, FFA and cancer cell pathogenicity in aggressive cancer cell lines. (A, B) JZL184 treatment (1 μM, 4 hr) increases MAG (A) and reduces FFA levels (B) in 231MFP cells. (C) shMAGL probes selectively reduce the activity of MAGL compared to other serine hydrolases in aggressive cancer cells C8161, SKOV3, and 231MFP as judged by activity-based protein profiling (ABPP). Serine hydrolase activities were labeled in whole cell proteomes with the activity-based probe FP-rhodamine and detected by SDS-PAGE and in-gel fluorescence scanning (fluorescent gel shown in grayscale). MAGL activity was reduced by >75% with both shMAGL probes (shMAGL1, shMAGL2), as assessed by ABPP (for C8161, SKOV3, and 231MFP) and C20:4 MAG substrate assays (for 231MFP). (D, E) shMAGL cells show increased levels of MAGs (D) and decreased levels of FFAs (E) compared to shControl or parental 231MFP cells. (F-H) shMAGL cells show decreased migration (F), invasion (G), and cell survival (H) compared to shControl or parental 231MFP cells. The migratory defect was rescued by treatment with C16:0 FFA or C18:0 FFA (20 μM, 4 hr). (I) Acute blockade of MAGL by JZL184 (1 μM, 4 hr) impairs cancer cell migration. $**p<0.01$ for JZL184-treated or shMAGL cells versus their respective control groups. $\#\#$ $p<0.01$ for C16:0 or C18:0 FFA-treated versus DMSO-treated shMAGL groups. Data are presented as means±SEM; n=4-6/group.
Figure 22:
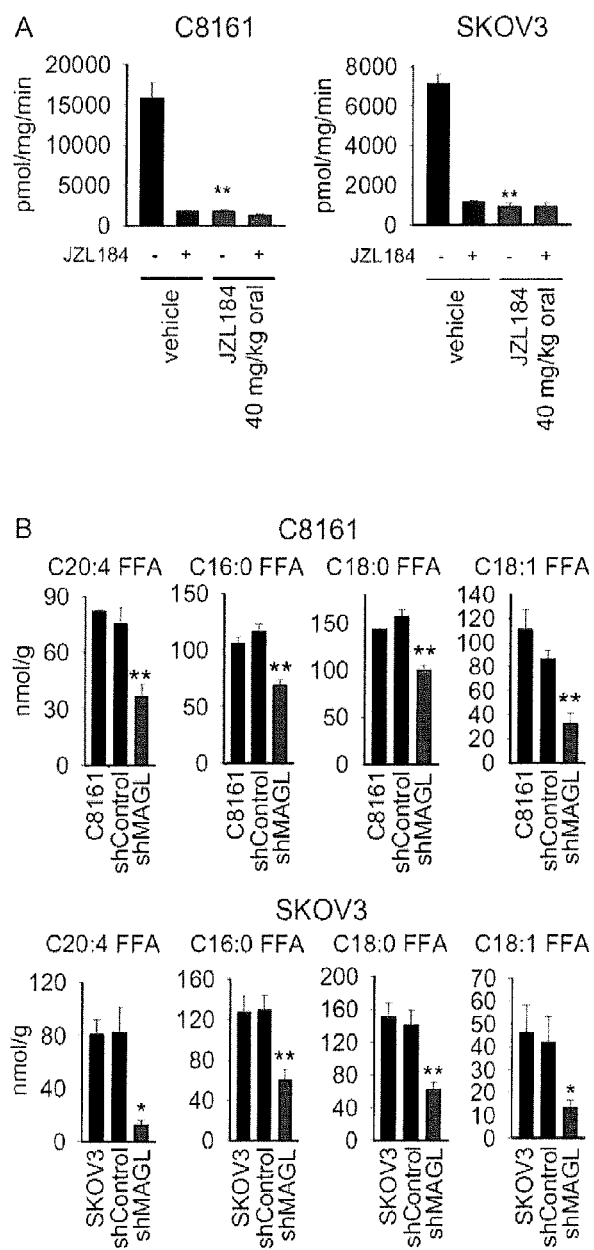
FIGS. 22A-22B show that in vivo treatment with JZL184 (40 mg/kg oral gavage, administered once daily for 30 days in 4 μL/g polyethylene glycol) inhibits tumor xenograft MAGL activity (A) and shMAGL tumors contained lower FFA levels compared to shControl cells (B). Vehicle or JZL184-treated SCID mouse tumor homogenates were incubated with DMSO or JZL184 (1 μM, 30 min) in vitro before addition of 100 μM C20:4 MAG for 30 min. $*p<0.05$, $**p<0.01$ for JZL184-treated or shMAGL tumors versus vehicle or shControl tumors, respectively. Data are presented as means±SEM; n=4/group.
Figure 23:
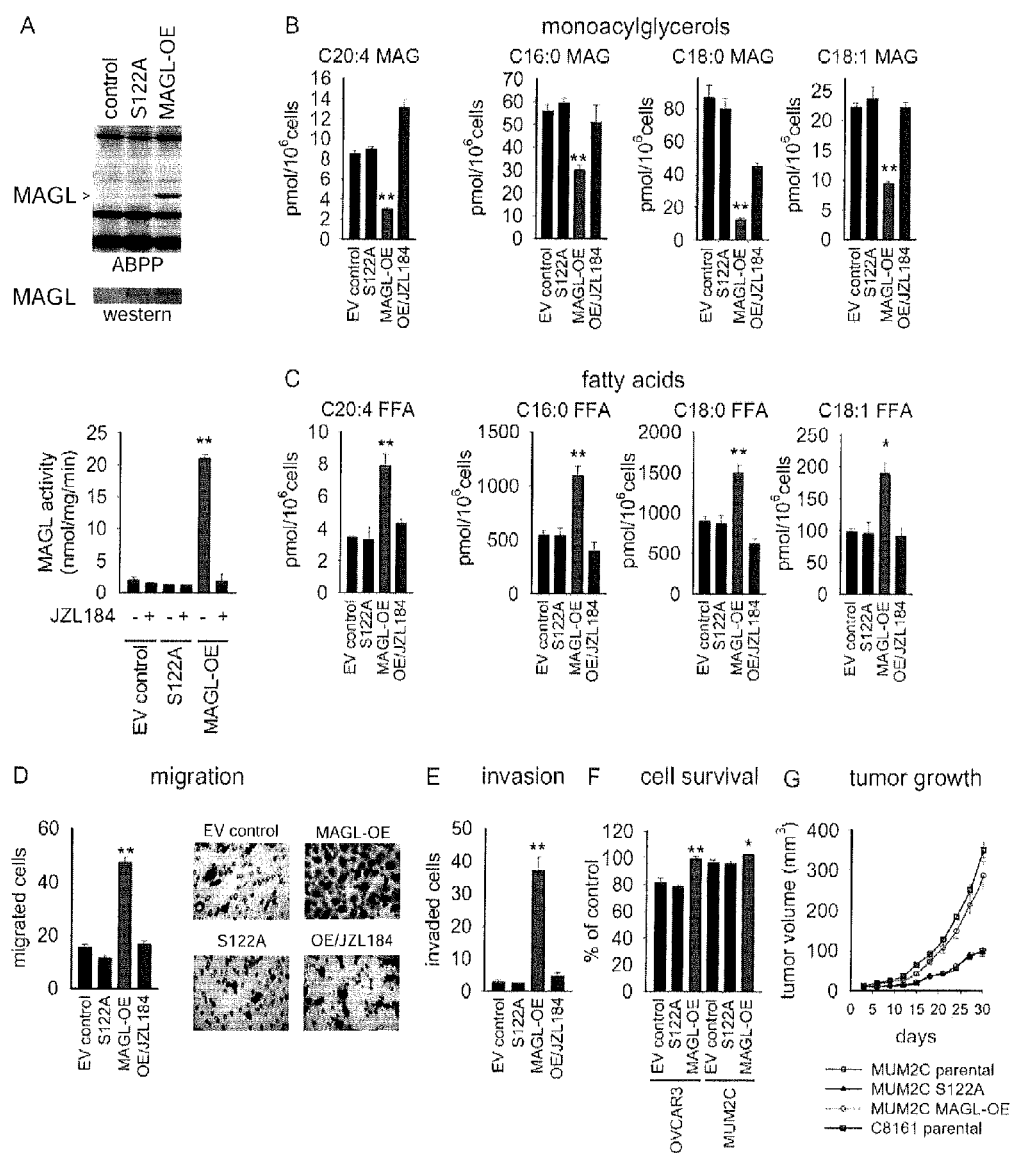
FIGS. 23A-23G show that ectopic expression of MAGL elevates FFA levels and enhances the in vitro and in vivo pathogenicity of OVCAR3 and MUM2C ovarian and melanoma cancer cells. (A) MAGL overexpression (MAGL-OE, red bars) in OVCAR3 cells confirmed by ABPP (top panel), western blot (middle panel) and C20:4 MAG hydrolytic activity (bottom panel). Control and S122A cells (black bars) correspond to cancer cells infected with empty vector (EV) or a catalytically inactive MAGL mutant (S122A). Western analysis confirmed the overexpression of the S122A-MAGL mutant, which did not show any activity as judged by ABPP and C20:4 MAG hydrolysis assays. (B, C) MAGL-OE cells contain lower MAG (B) and higher FFA (C) levels compared to EV control and S122A cells. These metabolic effects were reversed by in situ treatment with JZL184 (1 μM, 4 hr, maroon bars). (D, E) MAGL-OE OVCAR3 cells show increased migration (D) and invasion (E) compared to EV and S122A control cells. This enhanced migration and invasion was reversed by JZL184 (1 μM, 4 hr). Representative migration panels are shown (D). (F) MAGL-OE MUM2C and OVCAR3 cells show significantly enhanced cell survival (24 h after serum starvation) compared to EV control cells. (G) The enhanced tumor growth rate of MAGL-OE MUM2C cells is similar to the tumor growth rate of aggressive C8161 melanoma cells. The C8161 and MUM2C data are derived from FIG. 16E and FIG. 17F, respectively (note that these experiments were performed concurrently to permit a direct comparison of the tumor growth rates). $*$ $p<0.05$, $**$ $p<0.01$ for MAGL-OE- versus control groups. Data are presented as means±SEM; n=4-6/group.
Figure 24:
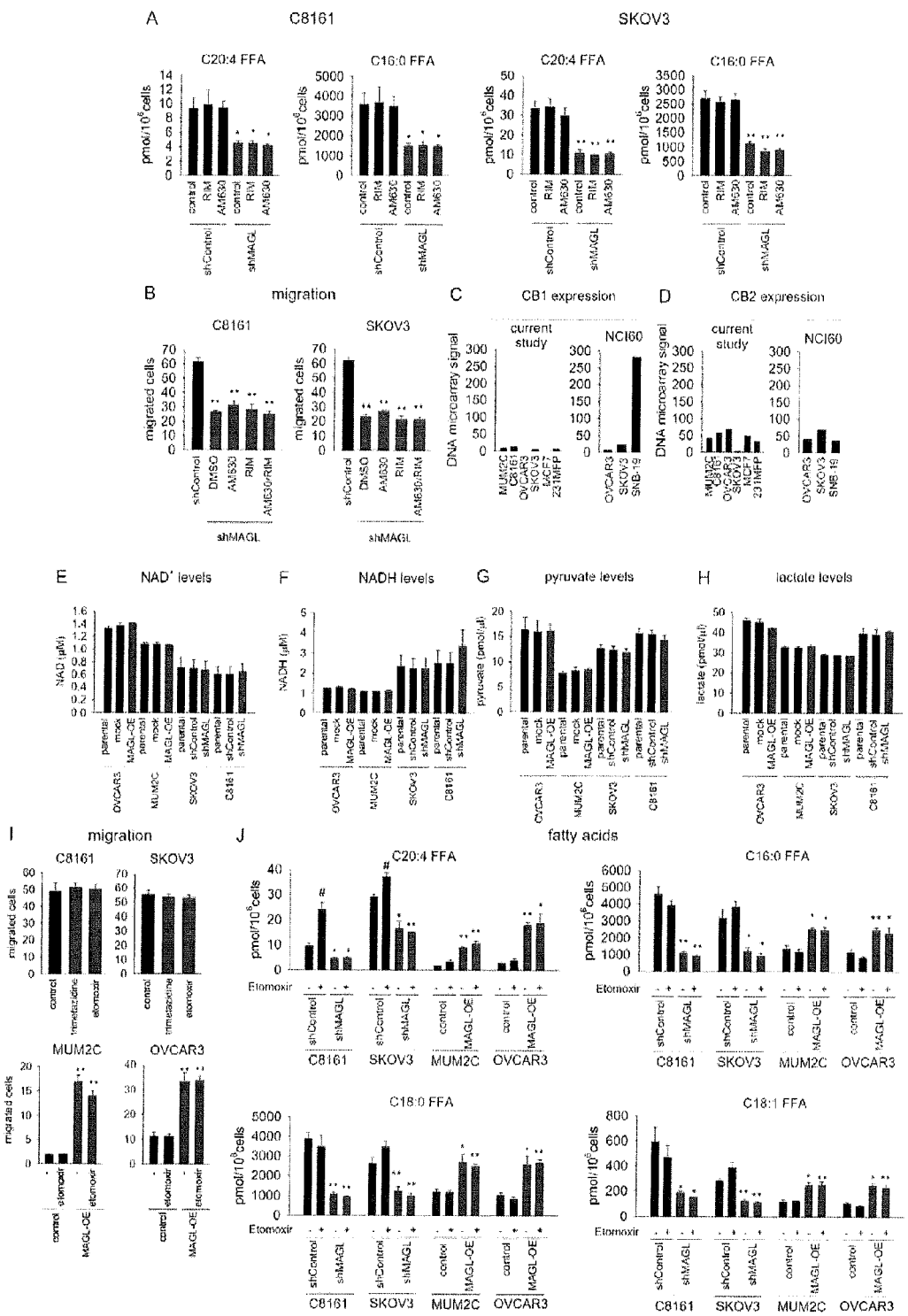
FIGS. 24A-24J show assessment of cannabinoid signaling, energetics, fatty acid beta oxidation or fatty acid synthesis in cancer aggressiveness. (A) FFA levels in shControl and shMAGL cancer cells were unchanged with CB1 (rimonabant, 1 μM, 4 hr) or CB2 (AM630, 1 μM, 4 hr) antagonist treatment. Data shown for C16:0 and C20:4 FFA. Similar results were observed for other FFAs (C18:0, C18:1). (B) The migratory defect in shMAGL cancer cells was not rescued by treatment with either the CB1 antagonist rimonabant or CB2 antagonist AM630 (1 μM, 4 hr), or co-treatment with both antagonists. $p<0.01$ for each shMAGL group versus shControl cells. Data are presented as means±SEM; n=6/group. (C, D) Levels of CB1 (C) and CB2 (D) receptor mRNA as determined by DNA microarray analysis. Left bar graph corresponds to data extracted from an analysis of the NCI60 panel of human cancer cell lines performed with a HU133APlus 2.0 Affymetrix array (Ross et al., 2000). Right bar graph corresponds to data extracted from an analysis of aggressive and non-aggressive cancer lines used in the current study performed with a HU133APlus 2.0 Affymetrix array. The SNB-19 cancer line, which contains high levels of CB1 receptor, is shown for comparison. (E-H) Increased (MAGL-OE) or decreased (shMAGL) expression of MAGL does not alter NAD$^+$ (E), NADH (F), pyruvate (G), or lactate (H) levels in cancer cells. Data are presented as means±SEM; n=6/group. (I) Fatty acid β-oxidation inhibitors trimetazidine (3-ketoacyl coenzyme A thiolase inhibitor, 100 µM, 4 hr preincubation and coincubation with migration) or etomoxir (CPT1 inhibitor, 100 µM, 4 hr preincubation and coincubation with migration) did not affect migration of cancer cells. p<0.01 for MAGL-OE versus control groups. Data are presented as means±SEM, n=3/group. (J) Etoxomir treatment (100 µM, 4 hr) did not alter FFA levels in cancer cells with the exception of C20:4 FFA, which was elevated in C8161 and SKOV3 cells. * p<0.05, ** p<0.01 for shMAGL or MAGL-OE cells versus their respective control groups. # p<0.05 for etoxomir-treated versus DMSO-treated control groups. Data are presented as means±SEM; n=3-4/group.
Figure 25:
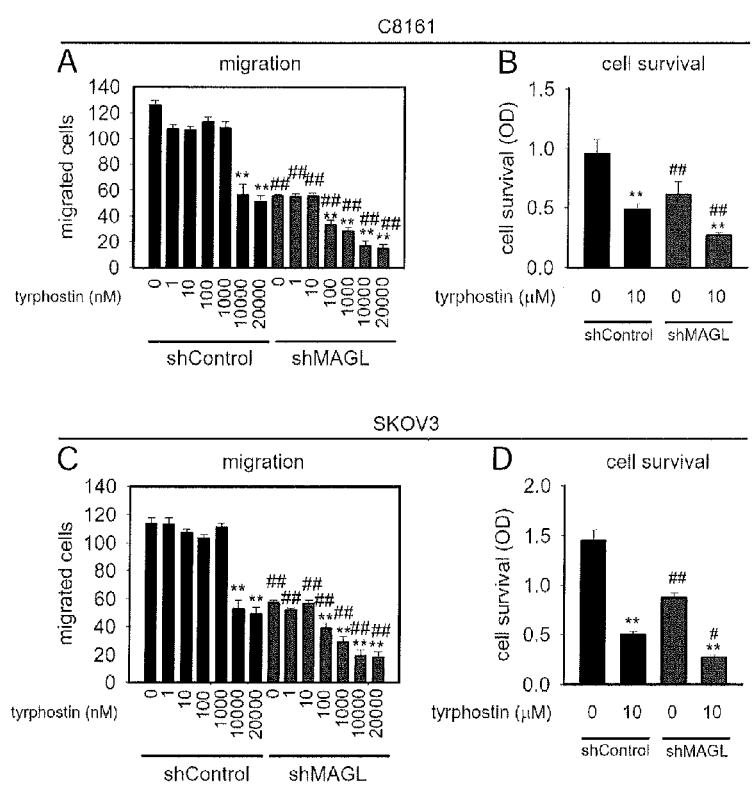
FIGS. 25A-25D show the effect of the EGFR kinase inhibitor tyrphostin on cancer cells. Tyrphostin decreased migration and cell survival (48 h, serum free) in C8161 (A, B) and SKOV3 (C, D) cells to a similar level as the migration and cell survival defects observed in shMAGL cancer cells. C8161 and SKOV3 shMAGL cells show enhanced sensitivity to tyrphostin-induced impairments in cell migration and survival (A, B). *p<0.05, **p<0.01 between tyrphostin- versus vehicle-treated shControl or shMAGL cancer cells; #p<0.05, ##p<0.01 between shControl and shMAGL cancer cells of the same treatment group. Data are presented as means±SEM, n=4/group.

We next stably knocked down MAGL expression by RNA interference technology using two independent shRNA probes (shMAGL1, shMAGL2), both of which reduced MAGL activity by 70-80% in aggressive cancer lines (FIG. 14A, FIG. 14 and FIG. 21). Other serine hydrolase activities were unaffected by shMAGL probes (FIG. 14A, FIG. 14 and FIG. 21), confirming the specificity of these reagents. Both shMAGL probes caused significant elevations in MAGs and corresponding reductions in FFAs in aggressive melanoma (FIG. 14B, 14C), ovarian (FIG. 14E, 14F), and breast cancer cells (FIG. 21). Together, these data demonstrate that both acute (pharmacological) and stable (shRNA) blockade of MAGL cause elevations in MAGs and reductions in FFAs in aggressive cancer cells. It is furthermore noteworthy that aggressive cancer cells were found to express higher basal levels of FFAs (and conversely lower levels of MAGs) than non-aggressive cancer cells (FIG. 13C, 13D), and this altered metabolic profile was largely eradicated by MAGL inhibition. These intriguing findings indicate that MAGL is the principal regulator of FFA levels in aggressive cancer cells. Finally, we confirmed that MAGL activity (FIG. 15A, 15B) and FFA levels (FIG. 15C) are also elevated in high-grade primary human ovarian tumors compared to benign or low-grade tumors. Thus, heightened expression of the MAGL-FFA pathway is a prominent feature of both aggressive human cancer cell lines and primary tumors.

Example 9

Control Cancer Pathogenicity by Modulating MAGL

Figure 16:
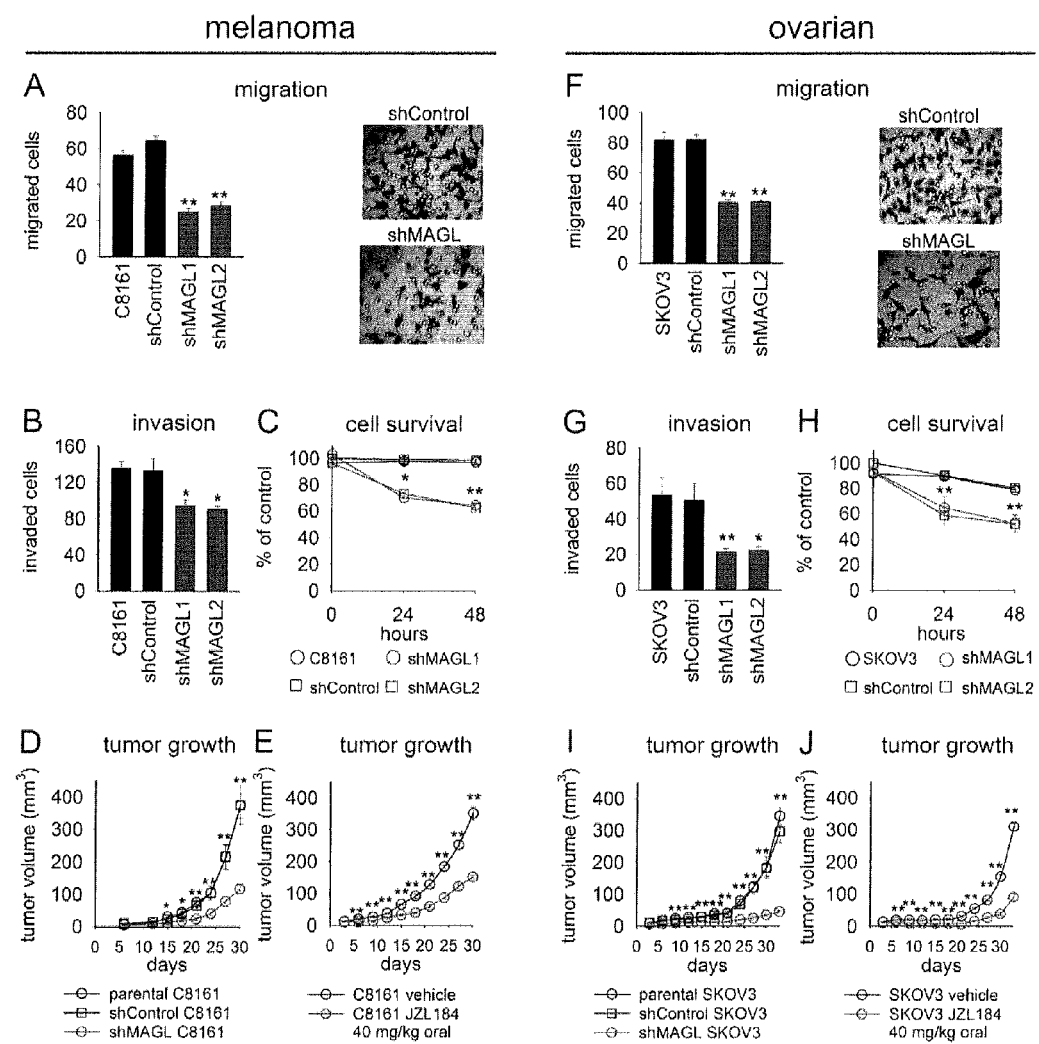
FIGS. 16A-16J show that shRNA-mediated knockdown and pharmacological inhibition of MAGL impair cancer aggressiveness. (A-C, F-G) shMAGL cells show decreased migration (A, F), invasion (B, G), and cell survival (C,H) compared to shControl and uninfected parental cells. Migration and invasion assays were performed by transferring cancer cells to serum-free media for 4 hours prior to seeding 50,000 cells into inserts with 8 µm-pore size containing membranes coated with collagen (10 µg/ml) or BioCoat™ Matrigel™, respectively. C8161 and SKOV3 migration times were 5 h and 20 h, respectively. Migrated or invaded cells refer to average numbers±sem per four fields counted at 400× magnification. Cell survival assays were performed by seeding 20,000 cells into 96 well plates in serum-free media. Survival was assessed using the WST-1 proliferation assay. Representative migration plates (at 400×magnification) are shown for shControl versus shMAGL cells (A, F). (D, I) shMAGL cells show impaired tumor growth in SCID mice compared to shControl and uninfected parental cells. $2 \times 10^6$ C8161 or SKOV3 cells/100 µl were injected subcutaneously into the flank and tumor growth was measured using calipers. (E, J) JZL184 treatment (40 mg/kg daily oral administration in 4 µl/g polyethylene glycerol 300 vehicle) significantly decreases tumor xenograft growth rates in SCID mice compared to vehicle treatment. * p<0.05, ** p<0.01 for shMAGL- versus shControl or JZL184- versus vehicle-treatment groups. shControl and parental cancer cells did not differ significantly in their migration, cell survival, invasion, or in vivo tumor growth. Data are presented as means±SEM; n=5-8/group.

We first determined effect of disruption of MAGL expression and activity on cancer pathogenicity. shMAGL cancer lines were examined for alterations in pathogenicity using a set of in vitro and in vivo assays. shMAGL-melanoma (C8161), ovarian (SKOV3), and breast (231MFP) cancer cells exhibited significantly reduced in vitro migration (FIG. 16A, FIG. 16F and FIG. 21), invasion (FIG. 16B, FIG. 16G and FIG. 21), and cell survival under serum-starvation conditions (FIG. 16C, FIG. 16H and FIG. 21). Acute pharmacological blockade of MAGL by JZL184 also decreased cancer cell migration (FIG. 21), but not survival, possibly indicating that maximal impairments in cancer aggressiveness require sustained inhibition of MAGL.

shMAGL-C8161 and SKOV3 cancer cells also exhibited markedly reduced tumor growth rates in subcutaneous xenograft transplantation studies performed in immune-deficient mice (FIG. 16D, 16I). Similar impairments in tumor growth rates were observed in C8161 and SKOV3 xenograft-transplanted mice administered JZL184 once per day (40 mg/kg, p.o.) (FIG. 16E, 16J), a treatment regime that was confirmed to block MAGL activity in tumors (data not shown). Notably, MAGL-disrupted tumors possessed lower FFA levels, indicating that MAGL maintains its control over fatty acid metabolism in cancer cells grown in vivo. Collectively, these in vitro and in vivo studies demonstrate that MAGL activity supports several of the aggressive properties exhibited by malignant cancer cells.

Figure 17:
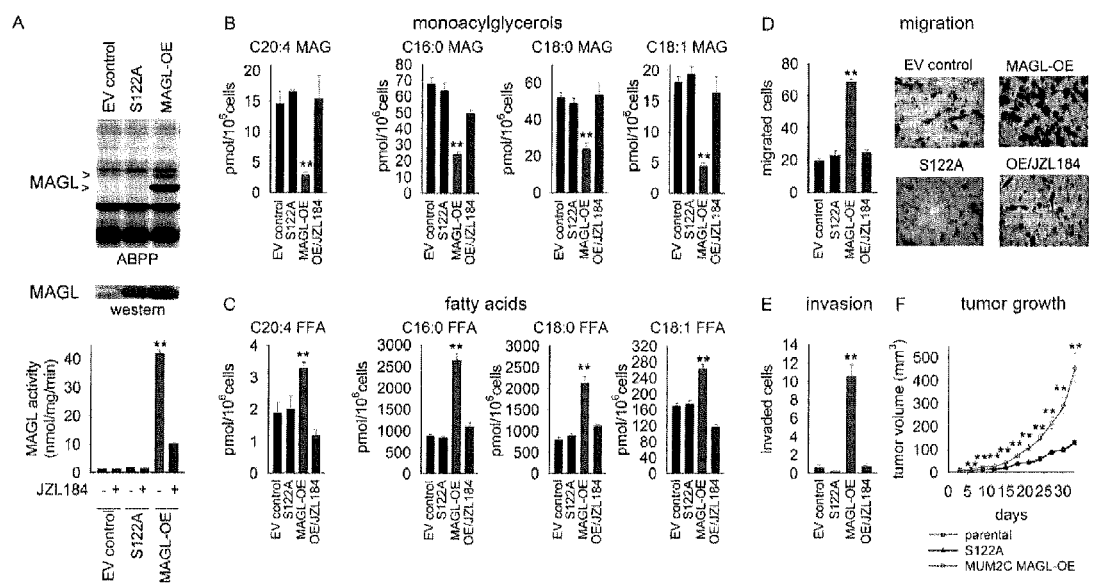
FIGS. 17A-17F show that ectopic expression of MAGL elevates FFA levels and enhances the in vitro and in vivo pathogenicity of MUM2C melanoma cells. (A) MAGL overexpression (MAGL-OE, red bars) in MUM2C cells confirmed by ABPP (top panel), western blot (middle panel) and C20:4 MAG hydrolytic activity (bottom panel). Control and S122A cells (black bars) correspond to cancer cells infected with empty vector (EV) or a catalytically inactive MAGL mutant (S122A), respectively. Western analysis confirmed the overexpression of the S122A-MAGL mutant, which did not show any activity as judged by ABPP and C20:4 MAG hydrolysis assays. (B, C) MAGL-OE cells contain lower MAG (B) and higher FFA (C) levels compared to EV control and S122A cells. These metabolic effects were reversed by in situ treatment with JZL184 (1 µM, 4 h, maroon bars). (D, E) MAGL-OE MUM2C cells show increased migration (D) and invasion (E) compared to EV and S122A control cells. This enhanced migration and invasion was reversed by JZL184 (1 µM, 4 h). Representative migration panels are shown (D). (F) MAGL-OE MUM2C cells show a significantly enhanced tumor growth rate compared to EV or S122A control cells in SCID mice (orthotopically implanted with $2 \times 10^6$ cells). * p<0.05, ** p<0.01 for MAGL-OE- versus control groups. Data are presented as means±SEM; n=4-6/group.

We next asked whether expressing MAGL in non-aggressive cancer cells might alter their lipid metabolic profiles and pathogenicity. Stable MAGL-overexpressing (MAGL-OE) and control [expressing an empty vector or a catalytically inactive version of MAGL, where the serine nucleophile was mutated to alanine (S122A)] variants of MUM2C and OVCAR3 cells were generated by retroviral infection and evaluated for their respective MAGL activities by ABPP and C20:4 MAG substrate assays. Both assays confirmed that MAGL-OE cells possess greater than 10-fold elevations in MAGL activity compared to control cells (FIG. 17A). MAGL-OE cells also showed significant reductions in MAGs (FIG. 17B) and elevated FFAs (FIG. 17C). This altered metabolic profile was accompanied by increased migration (FIG. 17D), invasion (FIG. 17E), and survival (data not shown) in MAGL-OE cells. None of these effects were observed in cancer cells expressing the S122A MAGL mutant, indicating that they require MAGL activity. Also consistent with this premise, both the metabolic and pathogenic effects observed in MAGL-OE cells were reversed by a single treatment with JZL184 (1 μM, 4 h) (FIG. 17). Finally, MAGL-OE MUM2C cells also showed enhanced tumor growth in vivo compared to control cells (FIG. 17F). Notably, the increased tumor growth rate of MAGL-OE MUM2C cells nearly matched that of aggressive C8161 cells (data not shown), indicating that MAGL is sufficient to induce a highly tumorigenic phenotype in melanoma cells. Collectively, these data indicate that the ectopic expression of MAGL in non-aggressive cancer cells is sufficient to elevate their FFA levels and promote pathogenicity both in vitro and in vivo.

Example 10

Metabolic Rescue of Impaired Pathogenicity in MAGL$^{31}$ cancer Cells

MAGL could support the aggressiveness of cancer cells by either reducing the levels of its MAG substrates, elevating the levels of its FFA products, or both. Among MAGs, the principal signaling molecule is the endocannabinoid 2-AG, which activates the CB1 and CB2 receptors. We therefore tested whether enhanced endocannabinoid signaling (resulting from elevated levels of 2-AG) might mediate the anti-migratory effects observed in MAGL-disrupted cancer cells. However, we found neither a CB1 nor CB2 antagonist rescued the migratory defects of shMAGL cancer cells. CB1 and CB2 antagonists also did not affect the levels of MAGs or FFAs in cancer cells (data not shown). These findings, combined with the low expression levels of CB1 and CB2 receptors in aggressive cancer cells (data not shown), argue that MAGL's effects on cancer aggressiveness were not mediated by endocannabinoid signaling.

Figure 18:
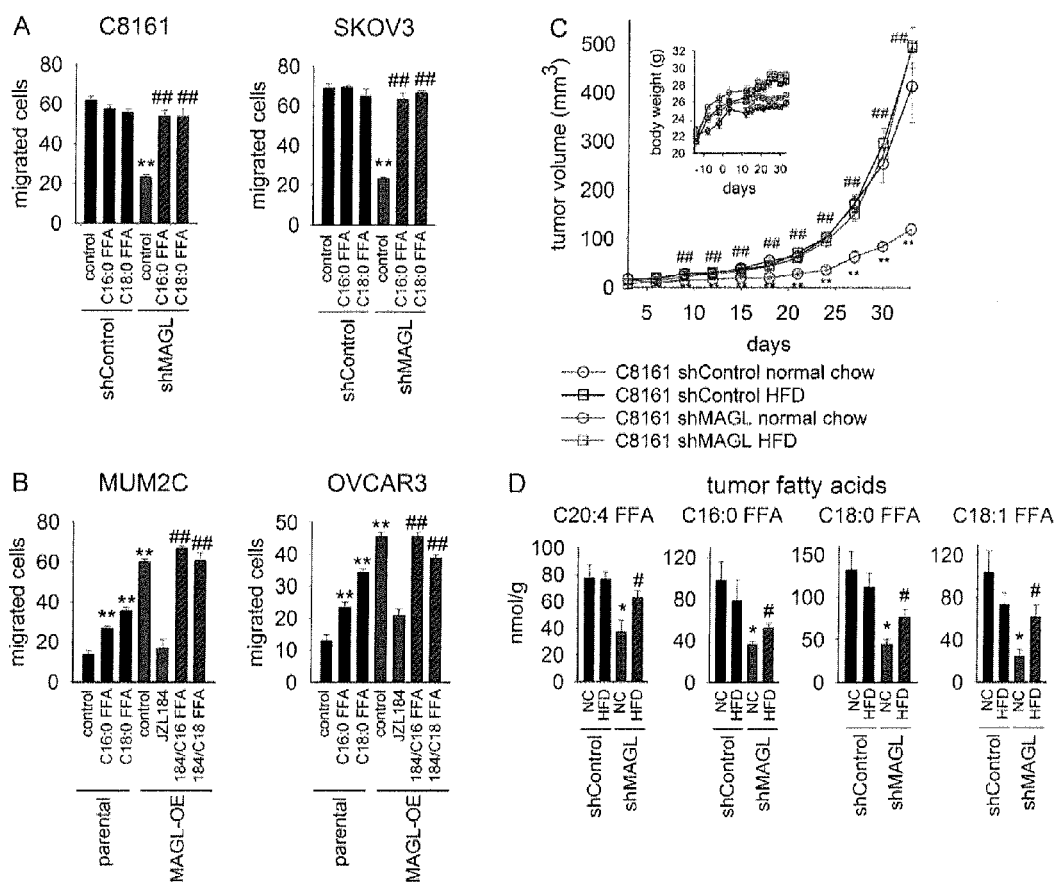
FIGS. 18A-18D show recovery of the pathogenic properties of shMAGL cancer cells by treatment with exogenous fatty acids. (A) The reduced migration of shMAGL cells is reversed by treatment with palmitic or stearic acid (20 µM, 4 h, hatched red bars). (B) Addition of palmitic or stearic acid (20 µM, 4 h) increases the migration of MUM2C and OVCAR3 cells and rescues the reduced migration in JZL184-treated MAGL-OE cells. (C) The reduced tumor growth of shMAGL-C8161 cells is reversed by treatment with a high-fat diet (HFD) (60 kcal % fat). Mice were placed on normal chow (NC) or HFD two weeks prior to flank injection of cancer cells and maintained on these diets throughout the tumor growth time course. Inset, body weights for animals throughout time course. (D) Explanted shMAGL tumors from the HFD-group (hatched red bars) contain elevated FFA levels compared to shMAGL tumors from the NC-group (red bars). * p<0.05, ** p<0.01 shMAGL versus shControl groups. ## p<0.01 for palmitic or stearic acid- or HFD-treated shMAGL groups versus shMAGL control groups (DMSO- and NC-treated groups, respectively). Data are presented as means±SEM; For (A), n=4-5/group; for (B, C), n=7-8/group.

Turning our attention to the products of MAGL-catalyzed reactions, we reasoned that, if the pro-tumorigenic effects of MAGL were mediated by FFAs (or their secondary metabolites), then the impaired pathogenicity of shMAGL cancer cells might be rescued by treatment with exogenous sources of fatty acids. In support of this premise, addition of palmitic or stearic acid (C16:0 and C18:0 FFAs, respectively; 20 μM, 4 h), two principal FFAs regulated by MAGL in aggressive cancer cells, to shMAGL or JZL184-treated MAGL-OE cancer cells fully restored their migratory activity (FIG. 18A, 18B). C16:0 and C18:0 FFAs were also found to stimulate the migratory activity of the non-aggressive cancer cells MUM2C and OVCAR3 (FIG. 18B). We then determined whether increased FFA delivery could rectify the tumor growth defect observed for shMAGL cells in vivo. Immune-deficient mice were fed either a normal chow or high-fat diet throughout the duration of a xenograft tumor growth experiment. Notably, the impaired tumor growth rate of shMAGL-C8161 cells was completely rescued in mice fed a high-fat diet. In contrast, shControl-C8161 cells showed equivalent tumor growth rates on a normal versus high-fat diet. The recovery in tumor growth for shMAGL-C8161 cells in the high-fat diet group correlated with significantly increases levels of FFAs in excised tumors (FIG. 18D).

Collectively, these results indicate that MAGL supports the pathogenic properties of cancer cells by maintaining tonically elevated levels of FFAs. We next asked whether this metabolic profile might impact the larger lipid networks of aggressive cancer cells.

Example 11

MAGL Regulates a Fatty Acid Network Enriched in Pro-tumorigenic Signals

We first considered whether the MAGL-FFA pathway might serve as a means to regenerate NAD+ (via continual fatty acyl glyceride/FFA recycling) to fuel glycolysis, which has been hypothesized to explain a need for elevated neutral lipid hydrolase activity in cancers (Przybytkowski et al., Biochem. Cell Biol. 85:301-310, 2007). Arguing against this model, we found that the NAD+/NADH ratios and pyruvate and lactate levels were unaltered in shMAGL and MAGL-OE cells relative to control cells. Another possible reason for increased lipolysis could be to generate FFA substrates for β-oxidation, which may serve as an important energy source for cancer cells. However, we also found that inhibitors of carnitine palmitoyltransferase 1 (CPT1), which catalyzes the rate-limiting step in β-oxidation, did not affect the migratory activity of cancer cells (shControl, shMAGL, or MAGL-OE). CPT1 blockade also failed to alter FFA levels in cancer cells, with the exception of C20:4 FFA, which was elevated only in shControl cells. Additional studies revealed reduced expression of CPT1 in aggressive cancer cells, providing further evidence against a role for β-oxidation as a downstream mediator of the pathogenic effects of the MAGL-fatty acid pathway.

Figure 19:
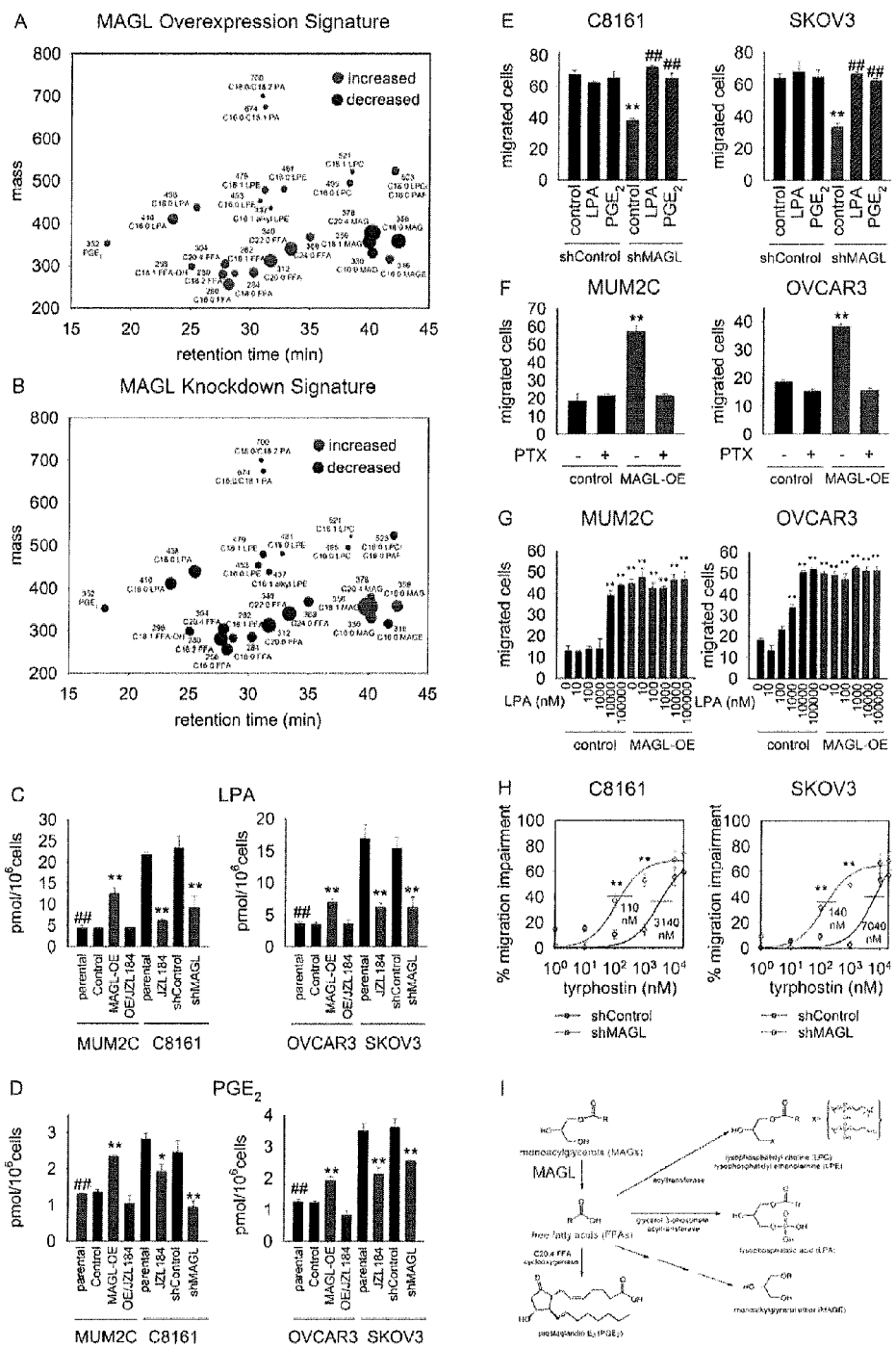
FIGS. 19A-19I show that MAGL regulates a lipid network enriched in pro-tumorigenic signaling molecules. (A, B) Lipidomic analyses of cancer cell models with altered MAGL activity comparing MAGL-OE versus EV control (A) and shMAGL versus shControl (B) cells. The metabolites shown are those that were increased (red) or decreased (blue) in MAGL-OE (both MUM2C and OVCAR3) versus EV control cells (A) and showed the opposite profile in shMAGL (both C8161 and SKOV3) versus shControl cells (B). Parent masses of metabolites are provided, and the size of circles indicates the relative magnitude of change. (C, D) Quantitation of C16:0 LPA and $PGE_2$ levels in cancer cell models. (E) Treatment of shMAGL cancer cells with C16:0 LPA (100 nM, 4 h) or $PGE_2$ (100 nM, 4 h) rescues their defective migration compared to shControl cells. (F) Pertussis toxin (PTX) (100 ng/ml, 4 h) reverses the increased migration of MAGL-OE cancer cells. (G) Concentration-dependent stimulation of migration by LPA in EV control versus MAGL-OE cells. Note that the maximal stimulation of migration induced by LPA In EV control cells matches the basally enhanced migration observe din MAGL-OE cells, and LPA does not further increase the migration of MAGL-OE cells. (H). Sensitivity of shControl versus shMAGL cancer cells to the EGFR inhibitor tyrphostin AG-1478, expressed as percentage of migration impairment. $IC_{50}$ values for the anti-migratory effects of tyrphostin are provided in the panels. (I) Scheme showing a possible metabolic network connecting the MAGL-FFA pathway to other pro-tumorigenic lipids. For (A) and (B), data are presented as mean relative changes between comparison groups; n=4-5/group. For (C-G), * p<0.05, ** p<0.01 for MAGL-OE or shMAGL versus respective control cell groups (C-G), JZL184-treated versus DMSO-treated control cells (C, D). ##, p<0.01 for parental non-aggressive (MUM2C, OVCAR3) versus aggressive (C8161, SKOV3) cells (C, D), or LPA/$PGE_2$-treated shMAGL versus shControl cells (E). Data are presented as means±SEM; n=3-5/group.

Considering that FFAs are fundamental building blocks for the production and remodeling of membrane structures and signaling molecules, perturbations in MAGL might be expected to affect several lipid-dependent biochemical networks important for malignancy. To test this hypothesis, we performed lipidomic analyses of cancer cell models with altered MAGL activity, including comparisons of: 1) MAGL-OE versus control cancer cells (OVCAR3, MUM2C), and 2) shMAGL versus shControl cancer cells (SKOV3, C8161). Organic extracts of cancer cells were analyzed using an untargeted liquid chromatography-mass spectrometry (LC-MS) platform that profiles several major lipid families, and metabolites with significantly altered levels between the comparison groups were identified using the XCMS software. Complementing these global profiles, we also conducted targeted measurements of specific bioactive lipids (e.g., prostaglandins) that are too low in abundance for detection by standard lipidomic methods. The resulting data sets were then mined to identify a common signature of lipid metabolites regulated by MAGL, which we defined as metabolites that were significantly increased or reduced in MAGL-OE cells and showed the opposite change in shMAGL cells relative to their respective control groups (FIG. 19A, 19B).

Most of the lipids in the MAGL-fatty acid network, including several lysophospholipids (LPC, LPA, LPE), ether lipids (MAGE, alkyl LPE), phosphatidic acid (PA), and prostaglandin E2 ($PGE_2$), displayed similar profiles to FFAs, being consistently elevated and reduced in MAGL-OE and shMAGL cells, respectively. Only MAGs were found to show the opposite profile (elevated and reduced in shMAGL and MAGL-OE cells, respectively). Interestingly, virtually this entire lipidomic signature was also observed in aggressive cancer cells when compared to their non-aggressive counterparts (e.g., C8161 versus MUM2C and SKOV3 versus OVCAR3, respectively). These findings demonstrate that MAGL regulates a lipid network in aggressive cancer cells that consists of not only FFAs and MAGs, but also a host of secondary lipid metabolites. We were further intrigued to find that acute inhibition of MAGL by JZL184 produced a distinct secondary lipidomic signature. As was observed in shMAGL cells, JZL184 treatment caused reductions in LPA and $PGE_2$ in each of the cancer lines expressing high levels of MAGL (FIG. 19C, 19D). In contrast, and as noted earlier, increases (rather than decreases) in LPCs and LPEs were observed in JZL184-treated cells (FIG. 20). These data indicate that acute and chronic blockade of MAGL generate distinct metabolomic effects in cancer cells, likely reflecting the differential outcomes of short- versus long-term depletion of FFAs. Finally, several additional classes of lipids, including phosphatidylcholines, phosphatidylethanolamines, ceramides, sphinogine-1-phosphate, cholesterol, diacylglycerols, and triacylglycerols, were not affected by reductions or elevations in MAGL activity, thus underscoring the restricted composition of the fatty acid network regulated by this enzyme.

Within the MAGL-fatty acid network are several pro-tumorigenic lipid messengers, including LPA and $PGE_2$, that have been reported to promote the aggressiveness of cancer cells. Metabolic labeling studies confirmed that aggressive cancer cells can convert both MAGs and FFAs to LPA and PGE2 and, for MAGs, this conversion was blocked by JZL184 (data not shown). Interestingly, treatment with either LPA or $PGE_2$(100 nM, 4 hr) rescued the impaired migration of shMAGL cancer cells at, concentrations that did not affect the migration of shControl cells (FIG. 19E). Conversely, the enhanced migratory activity of MAGL-OE cancer cells was completely blocked by the $G_i/G_o$ inhibitor pertussis toxin (FIG. 19F). Finally, the degree of stimulated migration observed in MAGL-OE cells equaled the maximal effect produced by exogenous addition of LPA (FIG. 19G). Taken together, these data suggest that MAGL contributes to cancer pathogenicity, at least in part, by elevating the production of bioactive lipids that act on G-protein-coupled receptors to promote high migratory activity. To assess whether the MAGL-fatty acid network interacts with other pro-tumorigenic signaling systems, we treated shMAGL and shControl cells with an inhibitor of the epidermal growth factor receptor (EGFR). shMAGL cells show significantly heightened sensitivity to the anti-migratory (FIG. 19H) and anti-survival (data not shown) effects of EGFR blockade. These data are consistent with previous findings indicating substantial crosstalk between LPA and EGFR signaling pathways in cancer cells.

Example 12

Materials and Methods for Studying MAGL in Tumor Pathogenesis

Materials. All cell lines, with the exception of C8161, MUM-2B, MUM-2C, and 231 MFP, are part of the NCI60 panel of cancer cell lines and were obtained from the National Cancer Institute's Developmental Therapeutics Program. The C8161, MUM-2B, and MUM-2C lines were provided by Mary Hendrix. The 231 MFP cells were generated from explanted xenograft tumors of MDA-MB-231 cells, as described previously (Jessani et al., 2004; supra). C15:0, C16:0, C18:0 and C18:1 FFAs, C18:1 FFA-OH and C16:0, C18:0, C18:1, and C20:4 MAGs were purchased from Sigma. C12:0 MAGE and C15:0 MAG were purchased from Alexis Biochemicals and Nu-check Prep, respectively. C20:4 FFA and $PGE_2$ were from Cayman Chemicals. Other representative lipid standards of various classes of lipids were purchased from Sigma, Cayman Chemicals, Nu-check Prep, or Avanti Lipids. FP-rhodamine and FP-biotin was synthesized by following previously described procedures. JZL184 was synthesized as previously detailed. The human MAGL antibody (against N terminal amino acids 1-121) was purchased from Novus Biologicals.

Pharmacological inhibition of MAGL in cancer cells. Pharmacological inhibition studies were conducted as described previously (Chiang et al., Chem. Biol. 13:1041-1050, 2006). Cancer cells were maintained in RPMI medium 1640 with 10% (v/v) fetal calf serum at 37° C. in a humidified atmosphere of 5% $CO_2$/95% air. At 80% confluency, cells were trypsinized and counted using a hemocytometer, and $1\times10^6$ cells were plated in 6 cm dishes (subconfluent). A total of 20 hr after plating, cells were washed twice with PBS and inhibitors were incubated in serum-free RPMI media with JZL184 (1 µM) or vehicle (DMSO) at 0.1%. After incubation for 4 hr, the cells were harvested and analyzed by ABPP or LC-MS.

Identification and comparative quantitation of serine hydrolase activities from cancer cell proteomes by ABPP-MudPIT. The soluble and unsoluble proteome fractions from each of the human cancer cell lines were generated as previously described (Jessani et al., 2002; supra) and analyzed by ABPP-MudPIT (Jessani et al., 2005; supra). Standard conditions for FP-Biotin proteome labeling reactions were as follows: proteomes were adjusted to a final protein concentration of 1.0 µg/~1 and 1000 µg of proteome were labeled with 5 µM of FP-biotin for 2 hours at room temperature (RT). After incubation, the unsoluble proteome was solubilized with 1% Triton-X, rotated at 4° C. for 1 hour. Enrichment of FP-labeled proteins from the soluble and unsoluble proteome fractions was achieved as previously described (Kidd et al., Biochemistry 40:4005-15, 2001). The avidin enriched proteome was washed 2 times for 8 minutes with 1) 1% SDS, 2) 6M Urea, 3) 50 mM Tris pH 8.0 and finally resuspended in 200 µl 8M Urea 50 mM Tris pH 8.0. Samples were then prepared for on-bead digestion by reduction with 10 mM TCEP for 30 minutes at room temperature and alkylated with 12 mM of iodoacetamide for 30 minutes at room temperature in the dark. Digestions were performed for 12 hours at 37° C. with Trypsin (3 µLs of 0.5 µgs/µl in the presence of 2 mM $CaCl_2$ after samples were diluted to 2M Urea with 50 mM Tris pH 8.0. Lastly peptide samples were acidified to a final concentration of 5% formic acid.

Digested peptide mixtures were loaded on to a biphasic (strong cation exchange/reverse phase) capillary column and analyzed by two-dimensional liquid chromatography (2D-LC) separation in combination with tandem mass spectrometry. Peptides were eluted in a 5-step MudPIT experiment (using 0, 10, 25, 80 and 100% salt bumps) and data was collected in an ion trap mass spectrometer, LTQ (Thermo Scientific) set in a data-dependent acquisition mode with dynamic exclusion turned on (60 s). Specifically, one full MS survey ($ms^1$) scan was followed by 7 $ms^2$scans. The $ms^2$ spectra data were extracted from the raw file using RAW Xtractor (version 1.9.1). ms$^2$ spectra data were searched using the SEQUEST algorithm (Version 3.0) against a custom made database containing the longest entry from v3.26 of the human IPI database associated with each Ensembl gene identifier resulting in a total of 22935 unique entries. Additionally, each of these entries was reversed and appended to the database for assessment of false-discovery rates. SEQUEST searches allowed for oxidation of methionine residues (16 Da), static modification of cysteine residues (57 Da-due to alkylation), no enzyme specificity and a mass tolerance set to ±1.5 Da for precursor mass and ±0.5 Da for product ion masses. The resulting ms$^2$ spectra matches were assembled and filtered using DTASelect (version 2.0.27). A quadratic discriminant analysis was used to achieve a maximum peptide false positive rate of 1%.

The total proteomic data obtained were initially filtered for serine hydrolases using a manually assembled list of InterPro domain identifiers (IPR000120, IPR000379, IPR001031, IPR001087, IPR001466, IPR002641, IPR002642, IPR002921, IPR004177, IPR005181, IPR007751, IPR008262, IPR010662) that correspond to known members of this family. The resulting set of serine hydrolases were then filtered for enzymes that displayed >10-fold higher spectral counts in FP-rhodamine-treated proteomes compared to "no-probe" control proteomes for at least one of the cancer cell lines examined. For these calculations, spectral count values from the membrane and soluble proteomes were combined for each serine hydrolase from each cancer line. This analysis resulted in a list of ~50 serine hydrolase activities. Previous studies have shown that comparative quantitation is best restricted to proteins that show an average of ≥10 spectral counts in at least one of the two groups under comparison (Jessani et al., 2005; supra). Using this filter (where comparison groups were defined as aggressive cancer lines compared to their non-aggressive counterparts), we identified ~35 serine hydrolase activities for comparative quantitation. Among these serine hydrolases, KIAA1363 and MAGL met the following criteria defined for aggressiveness-associated hydrolase activities: 1) average spectral counts >2-fold in all three aggressive cancer lines relative to their non-aggressive counterparts, and 2) a p-value of <0.01 for differences between each aggressive and non-aggressive cancer cell line pair.

ABPP and hydrolytic activity assays of cancer cell proteomes. Identification and comparative quantitation of serine hydrolase activities from cancer cell proteomes by ABPP-MudPIT or gel-based ABPP was conducted as previously described using FP-biotin (5 µM) and FP-rhodamine (2 µM), respectively (Jessani et al., Proc. Natl. Acad. Sci. U.S.A 99:10335-10340, 2002; and Jessani et al., Nat. Methods 2:691-697, 2005). C20:4 MAG hydrolytic activity assays were performed as described previously (Blankman et al., Chem. Biol. 14:1347-1356, 2007). For ABPP experiments, cell lysate proteomes were treated with 2 µM FP-rhodamine for 30 min at room temperature (50 µl total reaction volume). Reactions were quenched with one volume of standard 4×SDS/PAGE loading buffer (reducing), separated by SDS/PAGE (10% acrylamide), and visualized in-gel with a Hitachi FMBio IIe flatbed fluorescence scanner (MiraiBio). Integrated band intensities were calculated for the labeled proteins and averaged from three independent cell samples to determine the level of each enzyme activity. IC50 values were determined from dose-response curves from three trials at each inhibitor concentration by using SigmaPlot 10.0. MAGL expression was also assessed by western blotting using standard procedures.

For hydrolytic activity assays, cells were treated in situ with JZL184 (1 µM) for 4 h in serum-free RPMI media before harvesting cells by scraping. Cell lysates (20 µg) in Tris buffer were then incubated with lipid (100 µM, e.g. C20:4 MAG for MAGL activity) at room temperature for 30 min in a volume of 200 µl. Reactions were quenched with 600 µl 2:1 chloroform:methanol and 10 nmol of C15:0 FFA or C12:0 MAGE internal standard was added. The products were extracted into the organic layer which was extracted and directly injected into LC-MS. LC-MS settings were as previously described (Blankman et al., 2007; supra). Product levels (e.g. C20:4 FFA for MAGL activity) were quantified in relation to internal standard levels and standard curves generated between varying lipid concentration versus constant internal standard levels. Specific activity was determined during the linear phase of enzymatic reactions (i.e., less than 20% substrate utilized).

Human primary ovarian tumors. Patients were diagnosed and treated for ovarian tumors at Brigham and Women's Hospital and Dana-Farber Cancer Center, Boston, Mass. All patient-derived biologic specimens were collected and archived under protocols approved by the Human Subjects Committee of the Brigham and Women's Hospital. The histopathologic diagnosis was determined by the gynecological pathologists at Brigham and Women's Hospital. The tumors were classified and graded according to the International Federation of Gynecology and Obstetrics (FIGO) system. For this work, 10 benign and 13 high-grade malignant ovarian tumor samples were used for the MAGL activity and metabolite measurements. The benign cases included benign cysts, ovarian fibromas and benign serous cystadenomas, whereas the malignant cases were all high-grade papillary serous carcinomas. Fresh tumor tissues were cut with scalpels into 2-5 mm pieces, individually wrapped in aluminum foil, snap-frozen in liquid nitrogen and kept at −80° C. freezer. MAGL activity and FFA levels were measured as described above.

RNA interference studies in human cancer cell lines. RNA interference studies were conducted as described previously (Chiang et al., 2006). Briefly, short-hairpin RNA constructs were subcloned into the pLP-RetroQ acceptor system, and retrovirus was generated by using the AmphoPack-293 Cell Line (Clontech). Hairpin oligonucleotides utilized for RNA interference studies were: for MAGL (shMAGL1), 5'-CAACTTTCAAGGTCCTTGC-3' (SEQ ID NO:1) and (shMAGL2), 5'-AGACTACCCTGGGCTTCCT-3' (SEQ ID NO:2); for the shControl (shDPPIV), 5'-GATTCTTCTGG-GACTGCTG-3' (SEQ ID NO:3). The shControl construct was designed to target a distinct serine hydrolase that was not consistently altered between aggressive and non-aggressive cancer cells (DPPIV). Using an shControl construct that targets an endogenous protein (rather than a non-functional scrambled construct) controls for non-specific effects due to general activation of the RNA interference machinery. Virus containing supernatant from 1-6 d was collected, concentrated by ultracentrifugation, and, in the presence of 10 µg/ml polybrene, used to stably infect cells for 48 hr. Infection was followed by 3 days of selection in medium containing puromycin (1 µg/ml for C8161, MUM2C, SKOV3, and 231MFP and 0.3 µg/ml for OVCAR3), as the retroviral vector contained this selection marker. Infected cells were expanded and tested for the loss of enzyme activity by ABPP and C20:4 MAG hydrolytic activity.

Overexpression studies in human cancer cell lines. Stable MAGL overexpression was achieved by subcloning the MAGL gene into the pMSCVpuro vector (Clontech), generating retrovirus using the AmphoPack-293 Cell Line, as described above with the RNA interference studies. The human MAGL construct was generated by PCR with primers 5'-GCTCTCGAGGCCGCCATGCCAGAGGAAAGTTCC-3' (SEQ ID NO:4) and 5'-AGCTGAATTCTCAGGGTGGG-GACGCAGTTCCTG-3' (SEQ ID NO:5). PCR products were subcloned into the pMSCVpuro (Clontech) by using XhoI and EcoRI restriction sites.

Cell migration, cell survival, and invasion studies. Migration assays were performed in Transwell chambers (Corning) with 8 µm pore-sized membranes coated with 10 µg/ml collagen for 4 h at 37° C. A total of 24 hr before the start of the migration assay, cancer cell lines were plated at a concentration of $1 \times 10^6$ cells per 6 cm dish. At the start of the migration assay, cells were harvested by washing two times with PBS and were then serum starved in serum-free media for 4 hr. Inhibitor, lipid or vehicle (0.1% DMSO) were preincubated with the cells during this 4 h time. Serum-starved cells were trypsinized, spun at 1400×g for 3 min, resuspended, and counted. 50,000 cells were seeded in the upper chamber of the transwells in 200 µl serum-free media (containing inhibitor, lipid or vehicle). Inhibitor, lipid or vehicle was also added to the lower chamber, and cells were allowed to migrate for 5 h (for C8161 and 231MFP cells) or 20 hr (SKOV3, MUM2C and OVCAR3 cells). The filters were then fixed and stained with Diff-Quik (Dade Behring). Cells that had not migrated through the chamber were removed with a cotton ball. The cells that migrated were counted at a magnification of 400×, and 4 fields were independently counted from each migration chamber. An average of cells in 4 fields for one migration chamber represents n=1.

Cell survival assays were performed using the Cell Proliferation Reagent WST-1 (Roche) as previously described (Roca et al., J. Biol. Chem. 283, 25057-73, 2008; and Siddiqui et al., Breast Cancer Res 7, R645-654, 2005). Cells were washed twice in PBS, harvested by trypsinization, washed twice in PBS, centrifuged at 1400×g and resuspended in serum-free media. 20,000 cells were plated in 200 µl in 96-well plates in serum-free media 0, 24 or 48 h prior to addition of WST-1 (20 µl) for 4 h at 37° C./5% $CO_2$. Absorbance was measured at 450 nm using a spectrophotometer. Invasion assays were conducted using the BD Matrigel Invasion Chambers per the manufacturer's protocol.

Tumor xenograft studies. Human cancer xenografts were established by transplanting cancer cell lines ectopically into the flank of C.B17 SCID mice (Taconic Farms). Briefly, cells were washed two times with PBS, trypsinized, and harvested in serum-containing medium. Next, the harvested cells were washed two times with serum-free medium and resuspended at a concentration of $2.0 \times 10^4$ cells/µl and 100 µl was injected. Growth of the tumors was measured every 3 days with calipers. For HFD studies, mice were placed on a 60 kcal % fat diet (Research Diets), two weeks prior to cancer cell injections. Mice were weighed every 3-6 days. For chronic JZL184 treatment studies, mice were treated with JZL184 or vehicle once daily (at approximately the same time everyday) by oral gavage in polyethylene glycol 300 (4 µL/g). The treatments were initiated immediately after ectopic injection of cancer cells.

Lipid measurements in cancer cells. Lipid measurements were conducted similarly to protocols described previously (Chiang et al., 2006; supra). Cancer cells were grown in serum-free media for 4 hrs to minimize the contribution of serum-derived lipids to the cellular profiles. The cells ($1 \times 10^6$ cells/6 cm dish, 80% confluency) were washed with twice with phosphate buffer saline (PBS), isolated by centrifugation at 1,400×g, and dounce-homogenized in 4 ml of a 2:1:1 mixture of chloroform:methanol:Tris buffer. Samples were homogenized in the presence of the following synthetic standards: C12:0 MAGE (10 nmol), C15:0 FFA (10 nmol). Organic and aqueous layers were separated by centrifugation at 2000×g for 5 min and the organic layer was collected. The aqueous layer was acidified (for metabolites such as LPA) by adding 5% formic acid, followed by the addition of 2 ml chloroform. The mixture was vortexed, and the organic layers were combined, dried down under $N_2$ and dissolved in 100 µl chloroform, of which 30 µl was analyzed by LC-MS.

LC-MS analysis was performed by using an Agilent 1100 LC-MSD SL instrument. LC separation was achieved with a Gemini reverse-phase C18 column (50 mm×4.6 mm with 5 µm diameter particles) from Phenomonex together with a precolumn (C18, 3.5 mm, 2 mm×20 mm). Mobile phase A was composed of a 95:5 ratio of water:methanol, and mobile phase B consisted of 2-propanol, methanol, and water in a 60:35:5 ratio. Solvent modifiers such as 0.1% formic acid and 0.1% ammonium hydroxide were used to assist ion formation as well as to improve the LC resolution in both positive and negative ionization modes, respectively. The flow rate for each run started at 0.1 ml/min for 5 min, to alleviate backpressure associated with injecting chloroform. The gradient started at 0% B and increased linearly to 100% B over the course of 45 min with a flow rate of 0.4 ml/min, followed by an isocratic gradient of 100% B for 17 min at 0.5 ml/min before equilibrating for 8 min at 0% B with a flow rate of 0.5 ml/min. MS analysis was performed with an electrospray ionization (ESI) source. The capillary voltage was set to 3.0 kV, and the fragmentor voltage was set to 100 V. The drying gas temperature was 350° C., the drying gas flow rate was 10 L/min, and the nebulizer pressure was 35 psi.

Lipidomic analysis was performed in both targeted and untargeted mode by LC-MS analysis. Standard lipid classes were quantitated by targeting using selected ion monitoring (SIM) (except for very high-abundance metabolites which were quantitated by untargeted analysis) and identities of metabolites were confirmed by coelution of metabolites with their respective standards and mass accuracy to within 10 ppm as determined with an accurate mass Agilent 6520 Accurate Mass QTOF-MS-MS. Lipidomic analysis was performed in both targeted and untargeted mode by LC-MS analysis. Standard lipid classes were quantitated by targeting using selected ion monitoring (SIM) (except for very high-abundance metabolites which were quantitated by untargeted analysis) and identities of metabolites were confirmed by coelution of metabolites with their respective standards and mass accuracy to within 10 ppm as determined with an accurate mass Agilent 6520 Accurate Mass QTOF-MS-MS. These lipids were quantified by measuring the area under the peak and were normalized to an internal standard (C12:0 MAGE in positive mode or C15:0 FFA in negative mode). Absolute quantitation of each lipid species in pmoles/$1 \times 10^6$ cells was based on generation of a standard curve of a representative lipid from each class analyzed against 10 nmoles of C12:0 MAGE and/or C15:0 FFA, where the relative extraction efficiencies of lipids and standards were also taken into account. MAGs were also quantified based on a C15:0 MAG (instead of C12:0 MAGE) internal standard and identical results were obtained. There was less than 5% degradation of MAG to fatty acid acyl anion species at the MS interface. Since we quantified MAG levels against an unnatural C15:0 MAG species (which also had the same degradation pattern as endogenous MAG species), the minimal levels of MAG degradation at the interface did not interfere with absolute MAG quantitation. The dynamic linear ranges for MAG and FFA quantitation were 0.6-10,000 pmoles and 1-10,000 pmoles, respectively. Untargeted data were collected on an Agilent 1100 LC-MSD SL instrument using a mass range of 200-1200 Da and were exported as common data format (.CDF)

files for computational analysis. Differentially expressed metabolites between sample pairs were identified by using the XCMS analyte profiling software, which aligns and quantifies the relative signal intensities of mass peaks from multiple LC-MS traces. Significant inhibitor, shMAGL or MAGL-OE-sensitive peak changes were confirmed by manual quantification by using the area under the peak normalized to the internal standards (C12 MAGE for positive mode and C15:0 FFA for negative mode).

\* \* \*

It is understood that the examples and embodiments described herein are for illustrative purposes only and that various modifications or changes in light thereof will be suggested to persons skilled in the art and are to be included within the spirit and purview of this application and scope of the appended claims. Although any methods and materials similar or equivalent to those described herein can be used in the practice or testing of the present invention, the preferred methods and materials are described.

All publications, GenBank sequences, ATCC deposits, patents and patent applications cited herein are hereby expressly incorporated by reference in their entirety and for all purposes as if each is individually so denoted.

We claim:

1. A compound of formula I shown below:

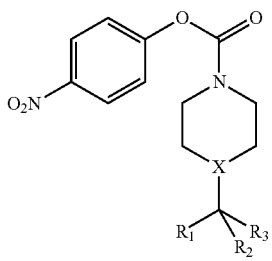

wherein X is CH, R₁ is H or OH, and R₂ and R₃ each have the structure

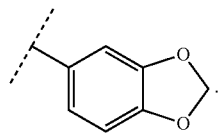

2. The compound of claim 1, wherein X is CH, R₁ is OH, and R₂ and R₃ each have the structure shown below

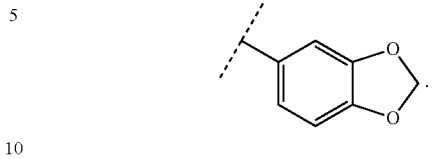

3. A method for inhibiting growth of an aggressive tumor cell, comprising contacting the cell with a therapeutically effective amount of a compound of claim 1, thereby inhibiting growth of the tumor cell.

4. The method of claim 3, wherein X is CH, R₁ is OH, and R₂ and R₃ each have the structure shown below

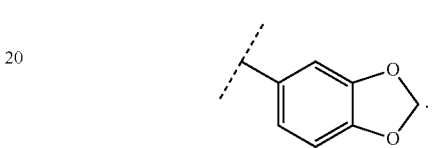

* * * * *